(12) United States Patent
Wang et al.

(10) Patent No.: US 11,161,800 B2
(45) Date of Patent: Nov. 2, 2021

(54) AMANTADINE NITRATE COMPOUNDS FOR USE AS MEDICAMENTS FOR THE TREATMENT OF DISEASES

(71) Applicant: GUANGZHOU MAGPIE PHARMACEUTICALS CO., LTD., Guangzhou (CN)

(72) Inventors: Yuqiang Wang, Guangzhou (CN); Zheng Liu, Guangzhou (CN); Pei Yu, Guangzhou (CN); Yewei Sun, Guangzhou (CN); Zaijun Zhang, Guangzhou (CN); Gaoxiao Zhang, Guangzhou (CN); Luchen Shan, Guangzhou (CN); Peng Yi, Guangzhou (CN); James Larrick, Woodside, CA (US)

( * ) Notice: Subject to any disclaimer, the term of this patent is extended or adjusted under 35 U.S.C. 154(b) by 543 days.

(21) Appl. No.: 16/350,687

(22) Filed: Dec. 20, 2018

(65) Prior Publication Data
US 2019/0202772 A1    Jul. 4, 2019

Related U.S. Application Data

(63) Continuation-in-part of application No. 15/530,054, filed on Nov. 28, 2016, now Pat. No. 10,214,478.

(51) Int. Cl.
*C07C 211/38* (2006.01)
*A61P 25/00* (2006.01)

(52) U.S. Cl.
CPC ............ *C07C 211/38* (2013.01); *A61P 25/00* (2018.01); *C07C 2603/74* (2017.05)

(58) Field of Classification Search
CPC ..... C07C 211/38; C07C 2603/74; A61P 25/00
USPC ........................................................ 514/662
See application file for complete search history.

(56) References Cited

U.S. PATENT DOCUMENTS 7,326,730 B2 * 2/2008 Wang .................. C07C 219/24
514/511

* cited by examiner

*Primary Examiner* — Kristin A Vajda
(74) *Attorney, Agent, or Firm* — Panterrain IP Law; Charles Liu

(57) ABSTRACT

The present invention relates to amantadine nitrate compounds having neural protective effect, and preparation method and medical use thereof. The compounds have the structure of the general formula (II).

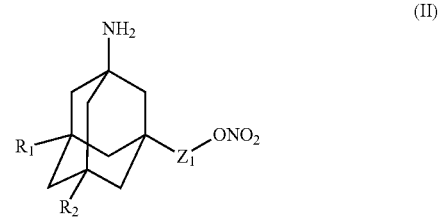

(II)

The compounds have multifunctional mechanisms, including inhibiting NMDA receptors, releasing NO, inhibiting calcium influxes, and having protective effects on cells particularly neurocytes. The compounds can be used in the preparation of medicaments having a cellular protective effect, for prevention or treatment of the diseases related to such as NMDA receptors and elevation of calcium anions in cells, including the diseases related to neurodegeneration such as Alzheimer's disease, Parkinson's disease, cerebral paralysis and glaucoma, and the diseases related to cardio-cerebral-vascular system such as Parkinson's syndrome combined with cerebral arteriosclerosis, as well as respiratory tract infections caused by influenza virus.

4 Claims, 26 Drawing Sheets

Reagents and conditions: (a) fuming HNO₃, Ac₂O, CH₂Cl₂; (b) HCl, ether.

Reagents and conditions: (a) HCOOH, n-Hexane, H₂SO₄; (b) CH₃CN, H₂SO₄; (c) ClCOOC₂H₅, TEA, NaBH₄; (d) NaOH, diethylene glycol, 170 °C, 15 h; (e) (Boc)₂O, Et₃N, CH₂Cl₂, 5 h; (f) Ac₂O, fuming HNO₃; (g) HCl, ether.

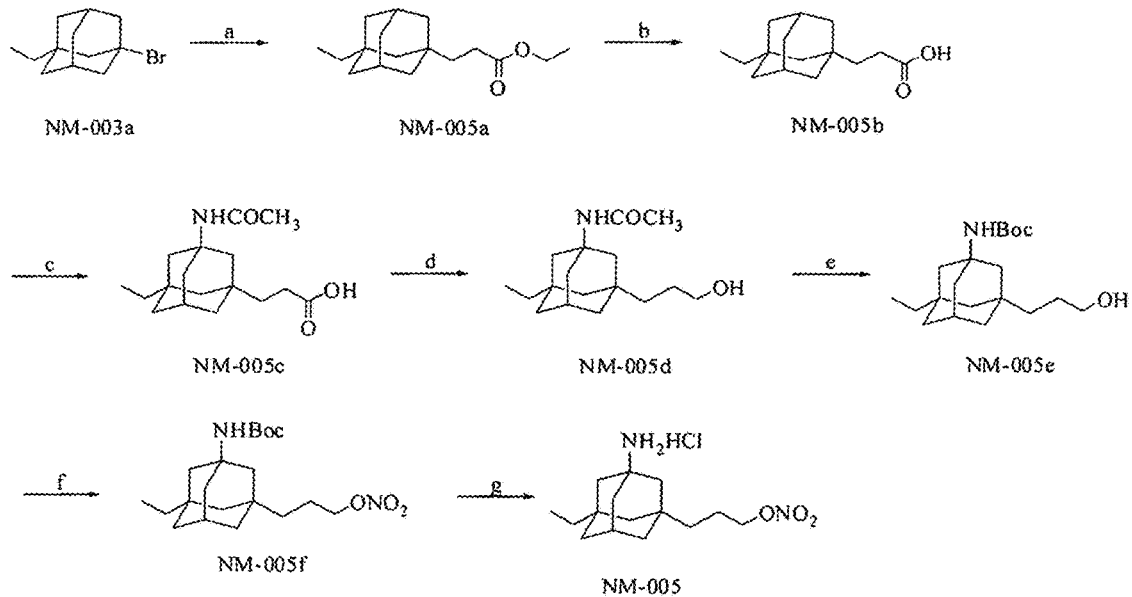

Reagents and conditions: (a) Ethyl acrylate, AIBN, n-Bu$_3$SnH, Toluene, 110 °C, 2 h; (b) KOH, MeOH/H$_2$O, rt, overnight; (c) CH$_3$CN, HNO$_3$,H$_2$SO$_4$; (d) ClCOOC$_2$H$_5$, Et3N, THF, NaBH$_4$; (e) NaOH, Diethylene glycol, 170 °C, 15 h; (f) (Boc)$_2$O, Et$_3$N, CH$_2$Cl$_2$, 5 h; (g) fuming HNO$_3$, Ac$_2$O, CH$_2$Cl$_2$; (g) HCl, ethyl.

FIG.3

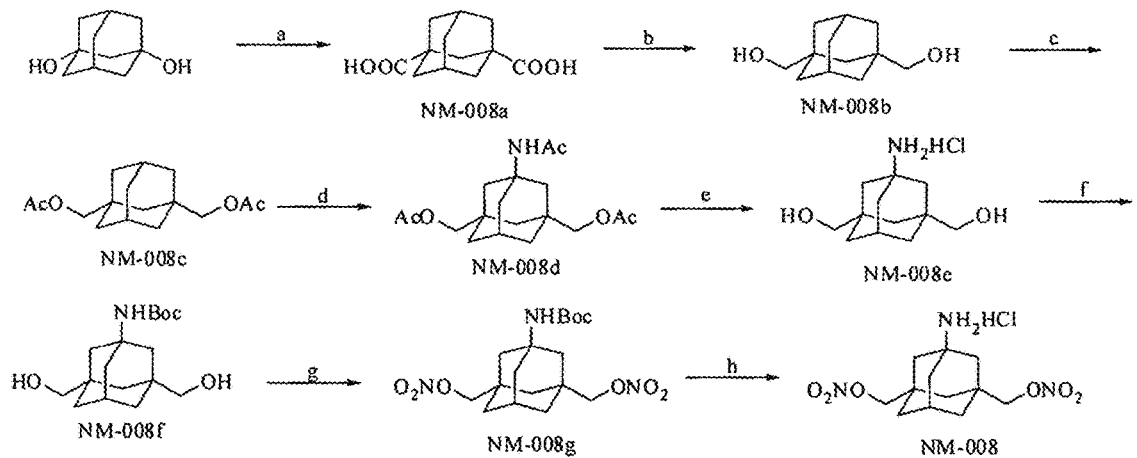

Reagents and conditions: (a) HCOOH, H$_2$SO$_4$, 3 h; (b) ClCOOC$_2$H$_5$, TEA, NaBH$_4$; (c) Ac$_2$O, HClO$_4$; (d) CH$_3$CN, H$_2$SO$_4$; (e) 18% HCl, 48 h; (f) DMF, (BOC)$_2$O, TEA, DMAP, 5 h; (g) Ac$_2$O, fuming HNO$_3$, CH$_2$Cl$_2$; (h) HCl, ether.

FIG.4

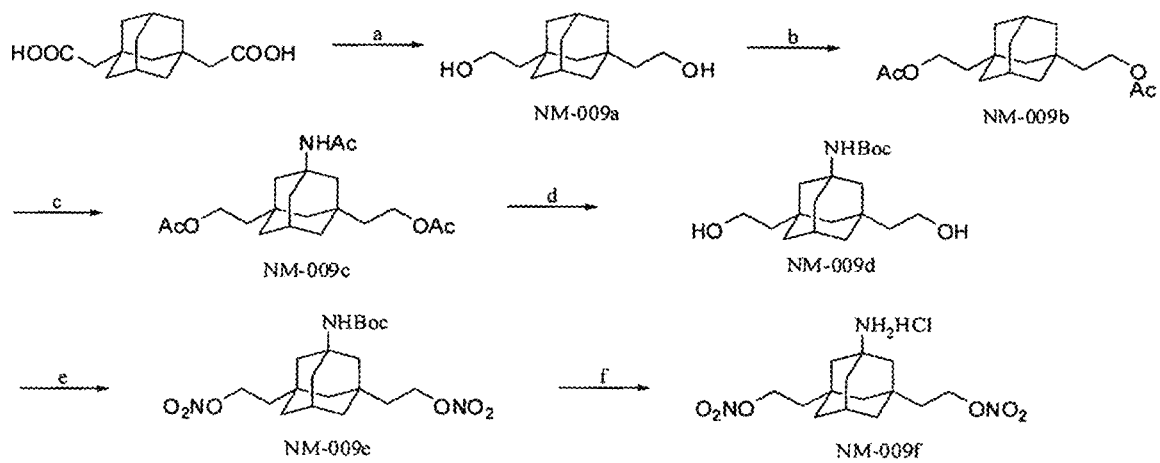

Reagents and conditions: (a) ClCOOC$_2$H$_5$, TEA, NaBH$_4$; (b) Ac$_2$O, HClO$_4$; (c) CH$_3$CN, H$_2$SO$_4$; (d) NaOH, Diethylene glycol, 170 °C, 15 h; (e) (BOC)$_2$O, TEA, THF, 5 h; (f) Ac$_2$O, fuming HNO$_3$,CH$_2$Cl$_2$; (g) HCl, ether.

FIG.5

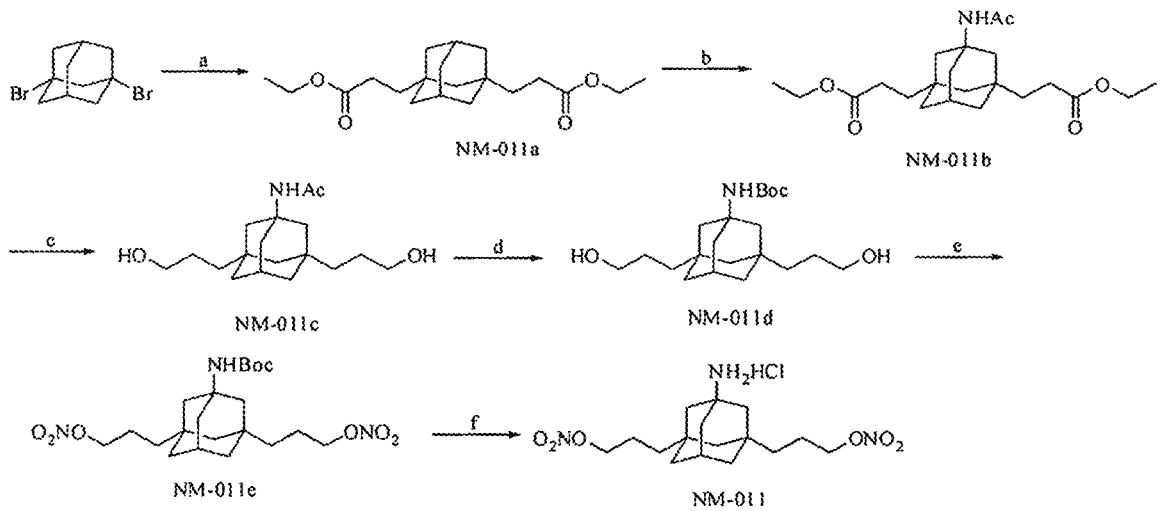

Reagents and conditions: (a) Ethyl acrylate, AIBN, n-Bu$_3$SnH, Toluene, 110 °C, 2 h; (b) CH$_3$CN, HNO$_3$,H$_2$SO$_4$; (c) NaBH$_4$, AlCl$_3$, THF; (d) (1)NaOH, Diethylene glycol, 170 °C, 15 h; (2) (Boc)$_2$O, Et$_3$N, CH$_2$Cl$_2$, 5 h; (e) fuming HNO$_3$, Ac$_2$O, CH$_2$Cl$_2$; (g)HCl, ethyl.

FIG.6

Reagents and conditions: (a) Ethyl methacrylate, AIBN, n-Bu$_3$SnH, Toluene, 110 °C, 2 h; (b) CH$_3$CN, HNO$_3$,H$_2$SO$_4$; (c) NaBH$_4$, AlCl$_3$, THF; (d) (1)NaOH, Diethylene glycol, 170 °C, 15 h; (2) (Boc)$_2$O, Et$_3$N, CH$_2$Cl$_2$, 5 h; (e) fuming HNO$_3$, Ac$_2$O, CH$_2$Cl$_2$; (g)HCl, ethyl.

A

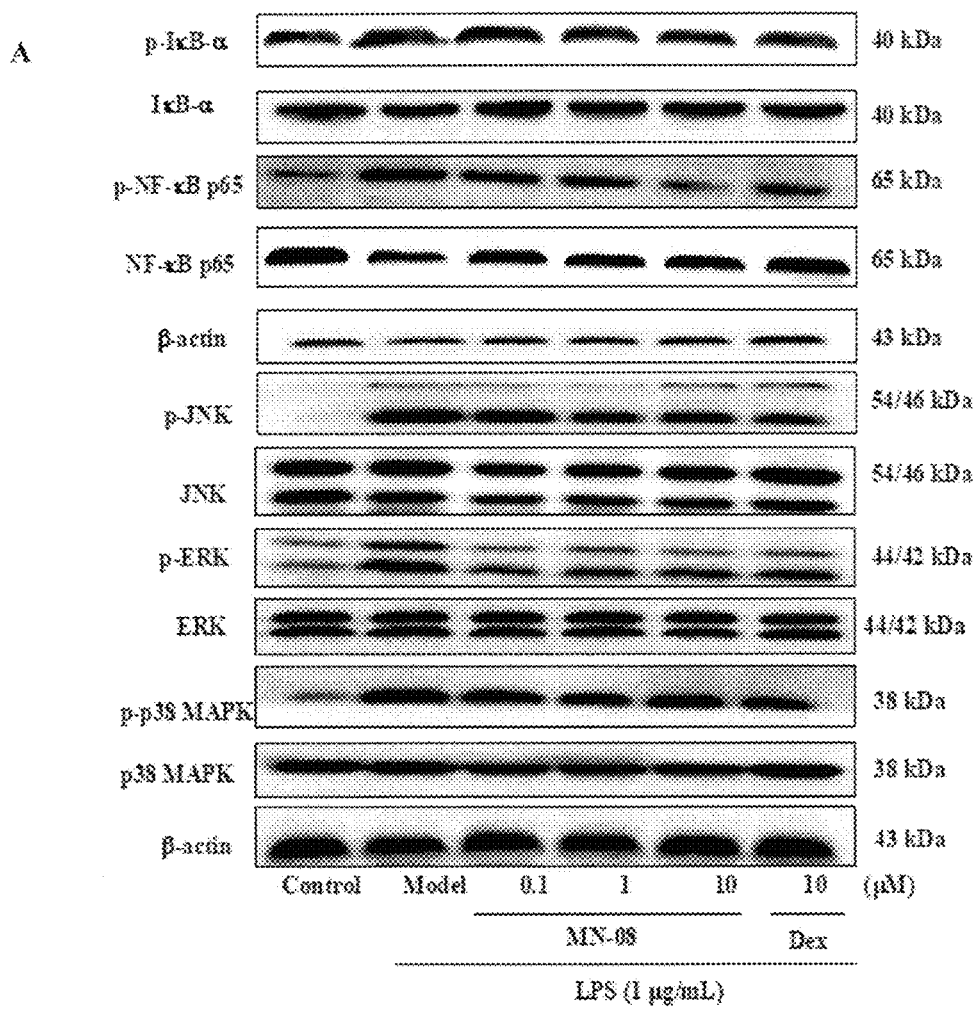
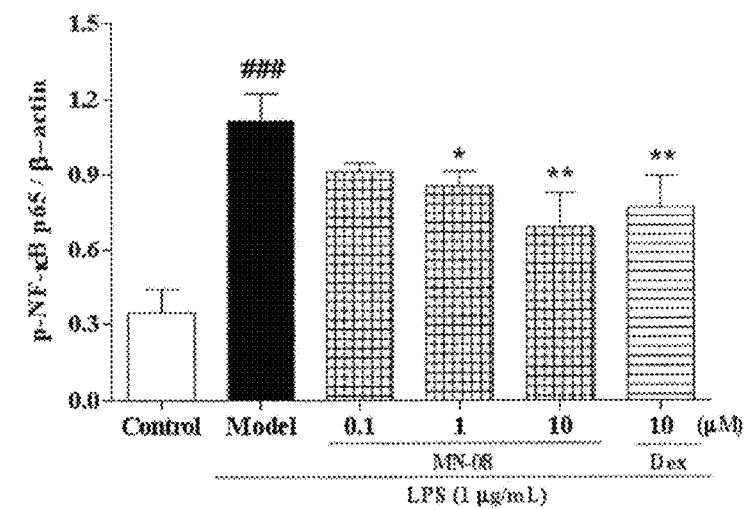
FIG. 19A-1
FIG. 19A-2

| Compound | Structure | Neuroprotection EC$_{50}$ (μM) |
|---|---|---|
| MN-04 | 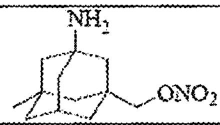 | 25.20 |
| MN-05 | 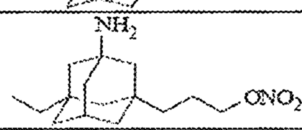 | 35.42 |
| MN-06 | 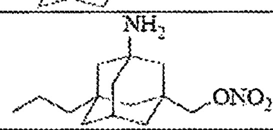 | 38.06 |
| MN-07 | 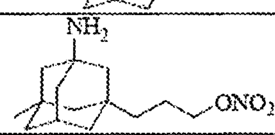 | 39.86 |
| MN-08 | 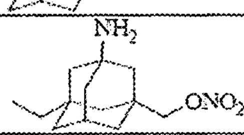 | 9.17 |
| MN-09 | 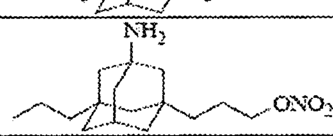 | 57.55 |
| Memantine | 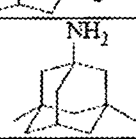 | 2.48 |

| Compound | Structure | NMDA receptor inhibition IC$_{50}$ (μM) |
|---|---|---|
| MN-08 | (structure) | 9.5 |
| MN-12 | (structure) | >100 |
| MN-13 | (structure) | >100 |
| Memantine | (structure) | 7.1 |

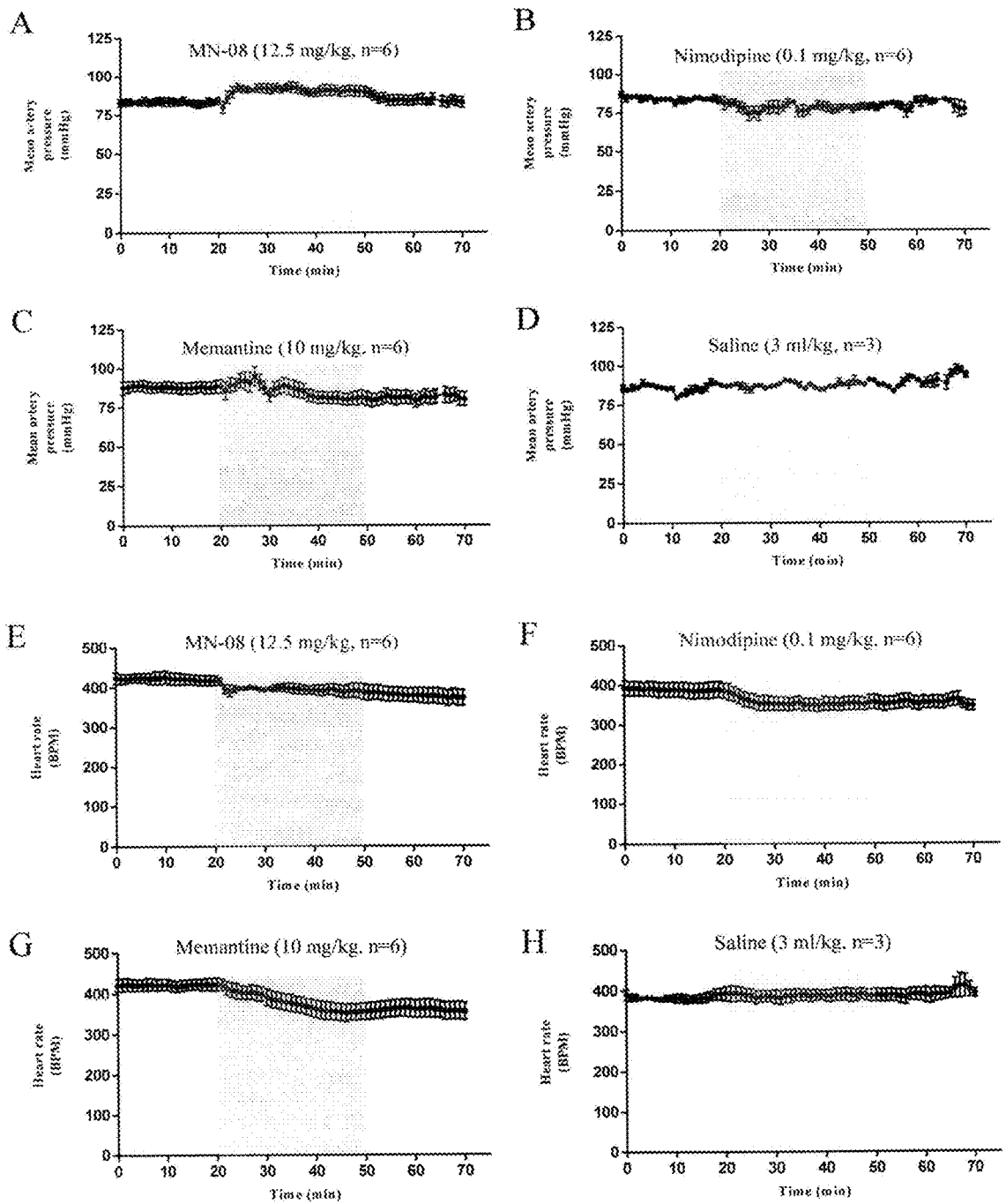
FIG. 25A-H

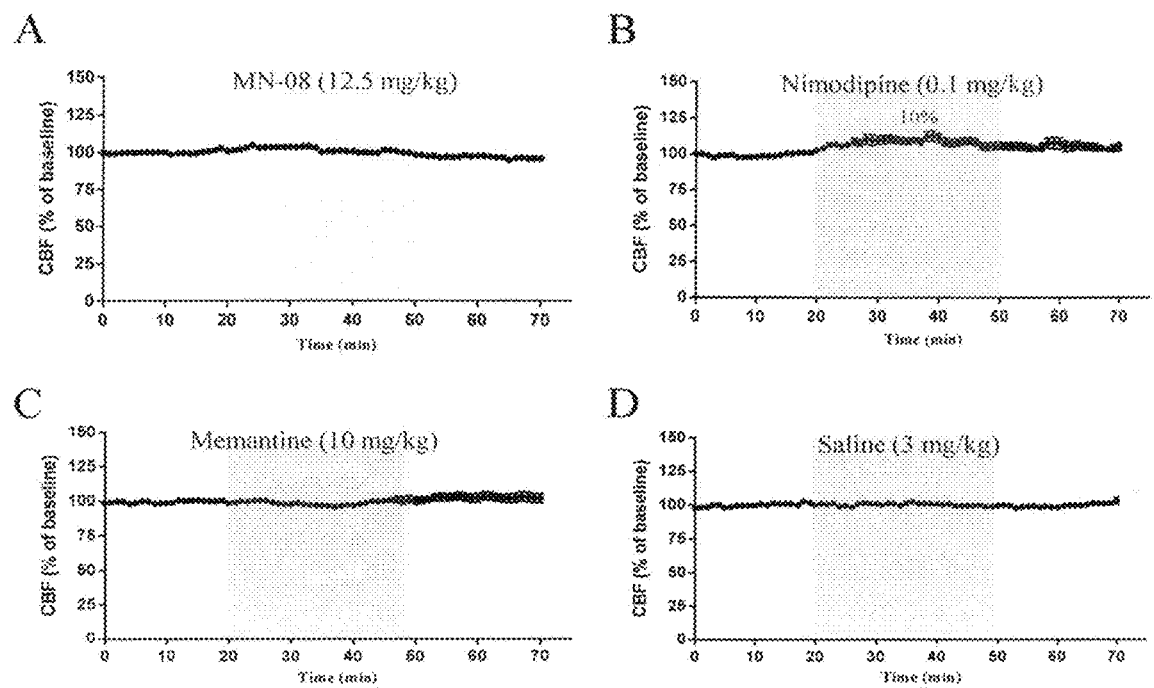
FIG. 26A-D
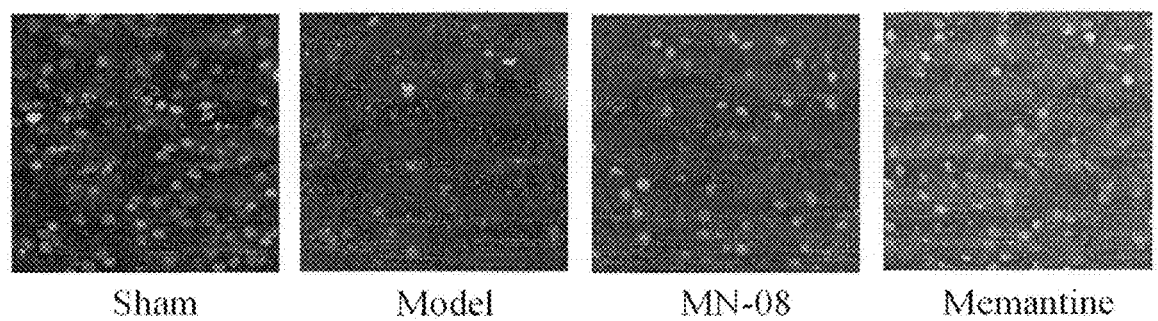
FIG. 27A
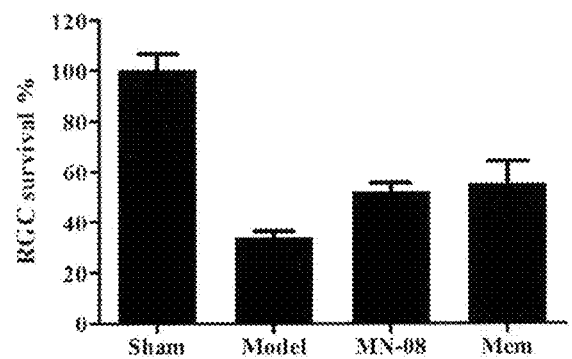
FIG. 27B

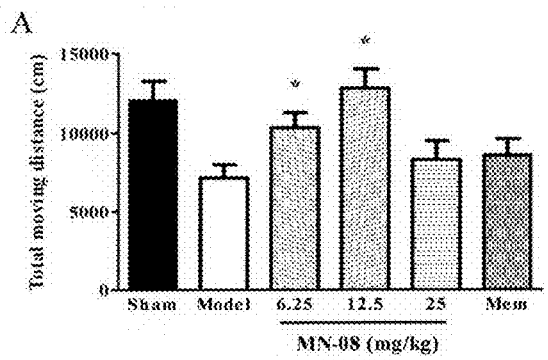 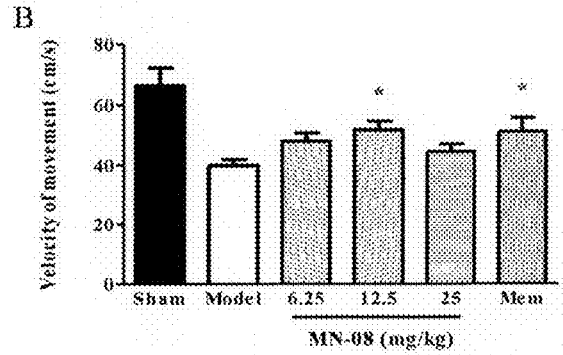
FIG. 30A          FIG. 30B
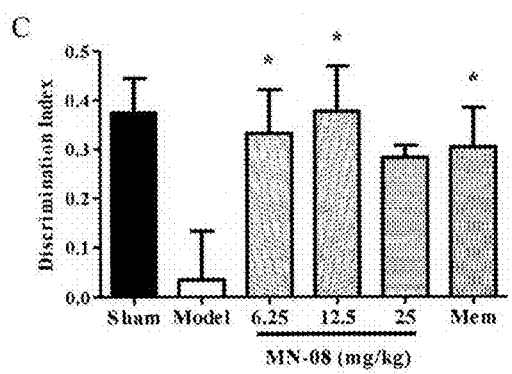
FIG. 30C
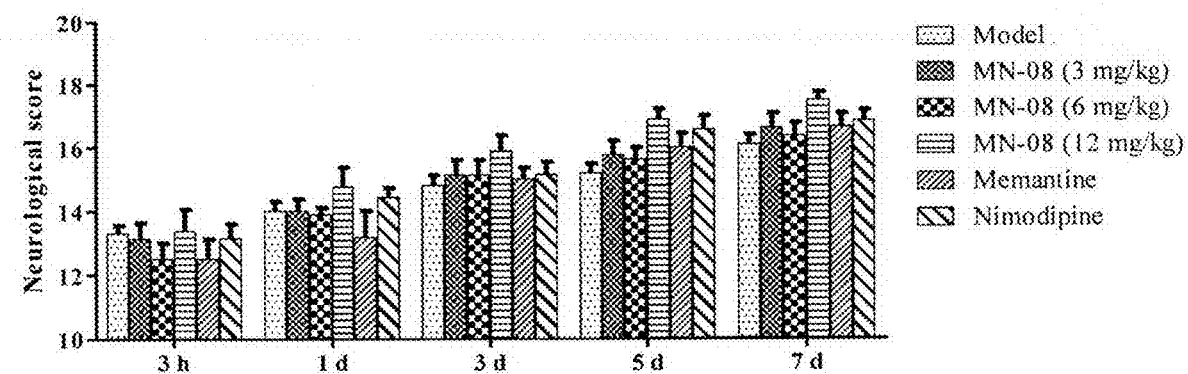
FIG. 31

AMANTADINE NITRATE COMPOUNDS FOR USE AS MEDICAMENTS FOR THE TREATMENT OF DISEASES

CROSS-REFERENCE TO RELATED APPLICATIONS

This is a Continuation-in-Part Application under 37 CFR 1.53(b) of prior U.S. patent application Ser. No. 15/530,054, filed Nov. 28, 2016, which claims the benefit of priority under 35 U.S.C. 120 to PCT Application No. PCT/CN2015/000314, filed May 8, 2015, published as WO 2015/180485 on Dec. 3, 2015, which claims the benefit of priority under 35 U.S.C. 119 of Chinese Patent Application No. 201410235747.5, filed May 29, 2014, the benefit of priority of each of which is claimed hereby, and each of which are incorporated by reference herein in their entirety.

FIELD OF THE INVENTION

The present invention relates to amantadine derivatives with neural protective effect, and more particularly to amantadine nitrate compounds for use as medicaments for the treatment of diseases.

BACKGROUND OF THE INVENTION

Amantadine and its derivatives with various biological activities have been widely used in the medical field. Rimantadine (1-aminoethyl adamantane) is currently used in medicaments for the prevention and treatment of influenza. Amantadine is widely used in the treatment of influenza and Parkinson's disease (PD) (Schwab et al., *J. Am. Med. Assoc.* 1969, 208: 1168). Memantine (1,3-dimethyl adamantane) currently is used as the only NMDA receptor antagonist proved by FDA to be used for the treatment of moderate to severe Alzheimer's Disease (AD). The NMDA receptor is an important subtype of excitatory amino acid ionic glutamate receptors in central nervous system, and is also an important receptor related to the learning and memory processes. When the NMDA receptor channel is opened, some cations, such as $Ca^{2+}$, $K^+$ and $Na^+$ maybe allowed unselectively to enter into the cells, and the entry of such ions, especially calcium ions, may cause a series of biochemical reactions, which may induce neurotoxicity and eventually cause neuronal apoptosis. Memantine is a noncompetitive antagonist of the NMDA receptor open-channel, and it can combine with the binding sites in the ion channel to block the ion flow and thus has neuro-protective effect. The combination of memantine to NMDA receptor is reversible with a moderate rate of dissociation, which may ensure the pharmacological effects and on the other hand may prevent the channel from being blocked for normal physiological functions (Lipton et al., *Journal of Neurochemistry* 2006, 97: 1611-1626). Meanwhile, memantine has a strong voltage dependence to the antagonism of the NMDA receptor and can bind to the receptor only under neuronal depolarization, and thus can block the activation of the NMDA receptor as neurons being continually polarized in pathological conditions, but does not block the activation of the NMDA receptor in normal physiological conditions (Wenk et al, *CNS Drug Reviews* 2003, 9 (3): 275-308; McKeage, *Drugs & Aging* 2010, 27 (2): 177-179). Such protection mechanism also has important significance for the treatment of other disorders of central nervous system, such as stroke, PD and ALS.

Nitric oxide (NO) also has a variety of biological activities in the body, and has a function of signaling molecules. Nitric oxide molecules can penetrate the cell wall into the smooth muscle cells to relax the cells, dilate blood vessels, and lower blood pressure. NO molecules can also enter into platelet cells and reduce their activities, and thus can inhibit the cells' aggregation and adhesion to the vascular endothelium, and further prevent thrombosis and atherosclerosis. Nitric oxide, as a free radical gas with an unpaired electron, is very unstable in the body and can easily react with free radicals, and thus can reduce the number of free radicals. The accumulation of free radicals can cause rupture of nucleic acids, inactivation of enzymes, depolymerization of polysaccharides, and peroxidation of lipids, and eventually may cause the neuronal death (Yan et al *Free Radic Biol Med* 2013, 62: 90-101). NO has very high activity towards various of radicals, and can effectively reduce the number of free radicals, however, it's synthesis in the body requires nitric oxide synthase (NOS). Under normal conditions, NOS has relatively low activity, and needs to be activated with nitro molecules or saponins. Introduction of a NO releasing group in a small molecule drug, such as in nitroglycerin, may increase NO content in the body, and thus may significantly enhance the therapeutic effect.

As the pathogenesis of AD is rather complex, currently available methods for clinical treatment of AD are very limited; there are only four kinds of acetylcholine esterase inhibitors and one NMDA receptor inhibitor. Such drug molecules with single target function may only relieve some clinical symptoms but cannot actually cure the disease of AD and thus cannot block the neurodegenerative process.

Glaucoma refers to an eye disease in which the intraocular pressure exceeds the limits of the intraocular tissues, especially the optic nerve, and causes optic disc depression, optic atrophy, and visual field defects. Elevated intraocular pressure is considered to be one of the important risk factors for the development of glaucoma disease, and it is also a factor that can be intervened. The treatment of glaucoma has so far been based on lowering intraocular pressure. In recent years, studies have found that in addition to elevated intraocular pressure, a variety of stimulating factors in glaucoma affect the stability of the intracellular environment, and the resistance of neurons to stimulating factors also determines their inherent susceptibility. There is evidence that when retinal ganglion cells are exposed to glaucomatous stress, they have a cascade of associated downstream cell activities, including mitochondrial dysfunction, proteolytic cascade reaction, endoplasmic reticulum stress, and oxidative stress. Therefore, in addition to reducing intraocular pressure, it is especially important to protect optic nerve cells. Glaucoma retinal ganglion cell apoptosis studies show that excitatory amino acid receptors (NMDA, AMPA and KA receptors) are present on retinal ganglion cells, which can cause hypoxia in ganglion cells when cells are in ischemia or high intraocular pressure, and further cause depolarization of the membrane, increased release of glutamate, and decreased uptake, which together lead to the accumulation of extracellular glutamate, which, under the action of its receptor, causes extracellular calcium influx, resulting in high load of intracellular calcium. The load leads to an increase in inducible NO synthase, lipid peroxidase, aggregation of oxygen free radicals, mitochondrial degeneration, and further leads to apoptosis of optic ganglion cells. Clinical studies have shown that the concentration of glutamate in the vitreous of patients with glaucoma is significantly elevated. In vitro studies have shown that blocking the excessive release of glutamate or interfering with the binding of NMDA receptors to glutamate protects retinal ganglion cells. The NMDA receptor antagonist memantine has been used as an optic neuroprotective drug in clinical phase III studies. Unfortunately, there was no significant difference between the memantine treatment group and the placebo group in the phase IIIb study. Recent studies have shown that low concentrations of NO (pmol or low level of nmol) have protective effects on glaucoma retina, with the indication of: relaxing diastolic intraocular smooth muscle, trabecular meshwork and Schlemm tube, thereby reducing aqueous circulation resistance, and reducing intraocular pressure; relaxing blood vessels, increasing blood flow, reducing vascular resistance; improving the retinal microcirculation through relaxation of capillaries. The NO donor drug currently in clinical research includes latanoprost, which is one of the most promising drugs for the treatment of glaucoma. Therefore, both the reduction of intraocular pressure and optic nerve protection drugs have undoubted advantages for glaucoma treatment, but there is no report on such drugs. At present, drug treatment is still the most commonly used intervention for reducing intraocular pressure. Traditional ocular hypotensive drugs include: beta-adrenergic antagonists, alpha-adrenergic receptor agonists, miotic agents and carbonic anhydrase inhibitors, and prostaglandin analogs. However, no neuroprotective drugs have been approved for marketing.

Vascular Dementia (VaD or VD) is a group of intelligent and cognitive dysfunction syndromes caused by cerebrovascular diseases and is one of the common causes of Alzheimer's disease. At present, the research suggests that the pathogenesis of VD is mainly related to the reduction of regional cerebral blood flow and nerve cell damage. In a variety of patients with neurological diseases and vascular dementia, local blood NO levels in brain tissue are significantly reduced (Corzo, et al., 2007), vascular tone is increased, and local cerebral perfusion is shown insufficient, causing damage to the blood-brain barrier, nerves pathophysiological changes such as cellular oxidative stress, calcium overload, and inflammatory response, ultimately leading to neural cell function disorder and cognitive impairment (Marshall, 2012; Malkki, 2015). Increasing NO is expected to improve blood supply to brain tissue and delay the pathological process of VD. NMDA receptors play an extremely important role in regulating neuronal survival, regulating the development of dendrites and axon structures, and participating in the formation of synaptic plasticity. They are a vital class of receptors in learning and memory (Lopez, et al., 2015; Zhang, et al., 2015). Studies have found that under pathological conditions such as ischemia and Alzheimer's disease, excessive activation of NMDA receptors can cause oxidative stress and calcium overload leading to neuronal cell damage or death, causing learning and memory and cognitive dysfunction in the body (Wroge, et Al., 2012); inhibition of NMDA receptor activity is effective in protecting neuronal cell damage. In fact, the NMDA receptor reversible inhibitor Mernantine has been shown to protect nerve cell damage, and clinical studies have demonstrated a significant improvement in cognitive function in some patients with small vascular VD. Although memantine has not met clinical needs due to its clinical efficacy (Orgogozo, et al., 2002; Wilcock, et al., 2002), it provides new ideas for VD treatment. In summary, local cerebral blood flow reduction and NMDA receptor activation caused by insufficient NO content play an extremely important role in the pathogenesis of VD. Therefore, increasing NO content in local brain tissue and inhibiting NMDA receptor activity are expected to be delayed or Reverse the pathological process of VD, thus providing an effective strategy for the prevention and treatment of VD.

Subarachnoid Hemorrhage (SAH) refers to a brain injury caused by blood flow into the subarachnoid space after the blood vessels in the bottom of the brain or the surface of the brain are ruptured. Cerebral vasospasm (CVS) is a dangerous pathophysiological condition after SAH. At this time, the cerebral blood vessels contract, and the blood flow in the brain blood supply area of the affected artery is reduced. NO is a potent endogenous vasodilator. Studies have shown that NO may decrease in blood vessels during SAH, while vasoconstrictor endothelin-1 (ET-1) increases, and imbalance between NO and ET-1 leads to CVS. However, multi-center clinical trials have shown that early brain injury after subarachnoid hemorrhage is the leading cause of death and disability. The molecular mechanisms of SAH brain injury include: calcium ion channel opening, free radical production, inflammatory reaction, apoptosis and necrosis. At present, the clinical treatment of SAH is very limited, only general treatment and symptomatic treatment, reduce intracranial pressure, prevent rebleeding. For early brain injury, there is still no effective treatment strategy. At present, the drug treatment of SAH and its CVS mainly includes: intracerebral thrombolysis such as rt-PA; drugs that inhibit vascular smooth muscle contraction such as calcium channel blockers, endothelin-1 (ET-1) antagonists, and the drug that improves NO bioavailability such as sodium nitroprusside.

Pulmonary Arterial Hypertension (PAH) is a condition in which blood pressure in the lungs is elevated. Any disease that blocks blood flow through the lungs can cause the disease. At present, the treatment of pulmonary hypertension mainly includes: drugs for directly expanding pulmonary vascular smooth muscle such as hydralazine, sodium nitroprusside, nitroglycerin and long-acting nitrate preparation; α-blockers such as phentolamine and tolazoline; β-receptor stimulants such as isoproterenol, terbutaline and dobutamine; calcium antagonists such as nifedipine (nifedipine), diltiazem (thiazepinone) and verapamil. angiotensin-converting enzyme inhibitors such as captopril and enalapril; prostaglandins such as alprostadil (prostaglandin E1), E2 (PGF2); nitric oxide inhalation therapy and endothelin receptor antagonists. Studies have shown that under pulmonary hypertension, elevated concentrations of glutamate in lung tissue lead to pulmonary vascular injury and vascular remodeling, so MNDA receptor antagonist memantine may also have a therapeutic effect on pulmonary hypertension.

Chronic obstructive pulmonary disease (COPD) is a disease characterized by incomplete reversibility of expiratory airflow limitation, accompanied by pulmonary inflammation and emphysema. The main feature is the progressive ventilatory obstruction of the bronchus leading to the lung tissue and/or the irreversible narrowing (occlusion), which ultimately leads to loss of elasticity of the lung tissue. Its pathogenesis involves several pathological processes caused by air pollutants (including cigarette smoke) and modified by genetic factors (polymorphisms) such as inflammation, cell growth, airway and/or substantial remodeling, proteases and anti-protease (Barnes P J. Chinics in Chest Medicine, 2014, 35(1): 71), cell apoptosis, abnormal cell repair, extracellular matrix destruction and oxidative stress (Wada H, Takizawa H. Recent Patents on Inflammation & Allergy Drug Discovery, 2013, volume 7:1-11(11)), aging and infection. At present, the commonly used therapeutic drugs for COPD include: bronchodilators such as β2 receptor agonists, anticholinergics, theophylline, and phosphodiesterase inhibitors; glucocorticoids; immunomodulators; and anti-inflammatory drugs and anti-oxidation agents.

Acute lung injury (ALI) refers to respiratory failure caused by non-cardiac severe internal and external pathogenic factors such as trauma, shock, ischemia-reperfusion, diffuse alveolar damage, and poisoning. Pathological manifestations include syndromes with the features of lung endothelial cell and epithelial cell damage, enhanced pulmonary capillary permeability, inflammatory cell infiltration, and progressive respiratory distress (Bakowitz M, Bruns B, McCunn M. *Scand J Trauma Resusc Emerg Med*, 2012, 20: 54). The severe stage of ALI is called acute respiratory distress syndrome (ARDS). The pathogenesis of ALI/ARDS is mainly involved in multiple interactions such as inflammation/anti-inflammatory, oxidation/antioxidation, coagulation/fibrinolysis system and apoptosis (Perl M, Lomas-Neira J, Venet F, et al. *Expert Rev Respir Med*, 2011, 5(1): 115-126). Literature shows that activation of NMDAR can induce acute high-permeability pulmonary edema in isolated rats, intraperitoneal injection of 0.5 g/kg glutamate can cause acute lung injury, and, as later confirmed, NMDA receptor antagonist MK-801 can significantly alleviated lung injury induced by oxygen free radicals in the perfused rat lung model. At present, there is still no effective drug treatment in clinical practice, the clinical course of ALI/ARDS is variable, and the pathophysiology of human ALI/ARDS is complicated. The treatment strategies for ALI/ARDS currently mainly include physical means and drug treatment. Among them, drug treatment mainly includes: glucocorticoids, anti-norepinephrine (NE) treatment, application of anisodamine, anti-cytokine drugs, surfactant replacement therapy, and antioxidant therapy.

Bronchial asthma, or simply referred to as asthma, is an airway chronic inflammatory disease involving a variety of cells, including adaptive and innate immune system inflammatory cells and airway autologous structural cells and their corresponding cellular components. It often leads to high airway response, high airway mucus secretion, and airway wall remodeling (Lambrecht B N, Hammad H. *Nature Immunology*, 2014, 16(1): 45-56). This chronic inflammation leads to airway hyperresponsiveness, often with variable reversible airflow limitation, and causes recurrent wheezing, shortness of breath, chest tightness or coughing. The pathogenesis of the disease is very complex, including: airway inflammation, airway hyperresponsiveness, immune and allergic mechanisms, airway remodeling, and airway neuro-receptor regulation mechanisms. At present, the most effective way to prevent and treat bronchial asthma in clinic is still drug treatment. Commonly used drug treatments include: glucocorticoids, β2 receptor agonists, leukotriene receptor antagonists, anticholinergic agents, theophylline drugs, antiallergic drugs, immunotherapy.

Studies have shown that pulmonary blood vessels have NMDA receptor expression, so amino adamantine nitrate compounds bind to pulmonary vascular NMDA receptor, release NO, and dilate pulmonary vessels. In addition, amino adamantane nitrate compounds are highly aggregated in lung tissue, up to 28-29%. These characteristics not only enable amino adamantane nitrate compounds to achieve effective therapeutic concentrations in lung tissue, but also prevent the release of NO in the whole body, which has less effect on systemic circulation and is safer than other conventional vasodilator drugs. In summary, the role of NMDA receptor overactivation in lung tissue damage is not negligible, and it may be involved in the occurrence and development of various lung diseases. Research in this field will clarify the physiological and pathological significance of peripheral receptors, and provide new ideas for the research and prevention of lung diseases such as ALI, asthma and COPD.

SUMMARY OF THE INVENTION

The present invention is directed to provide amantadine nitrate compounds of multifunctional targets and having neural protective effects. Of these compounds, multiple pharmacophores with specific targets were incorporated into the same molecule on the basis of drug design theories of pharmacophores, such that the compounds may have functions of inhibiting NMDA, releasing NO, inhibiting calcium influxes, removing radicals and neuro-protection. These compounds, which have multiple mechanisms, can be used to improve efficacy and reduce toxicity and side effects associated with combination therapy.

The present invention is also directed to provide a method of preparation of the amantadine nitrate compounds having neural protective effects.

The present invention is further directed to provide uses of the amantadine nitrate compounds with neural protective effects in the manufacture of medicaments.

The compounds of the invention have a structure of formula (I):

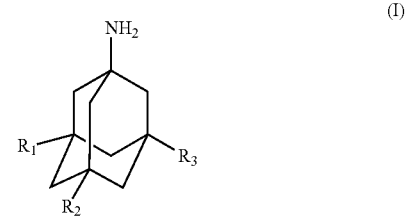

wherein, $R_1$, $R_2$ and $R_3$ are each independently hydrogen, straight-chain or branched-chain alkyl, optionally substituted or unsubstituted aryl, heteroaryl or nitrate ester group, and at least one of $R_1$, $R_2$ and $R_3$ contains a nitrate ester group.

The compounds of formula (I), in a preferred embodiment, have a structure of formula (II):

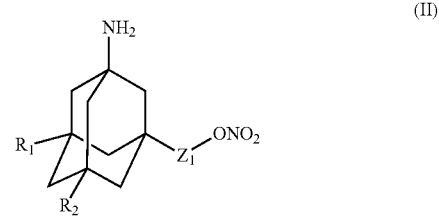

wherein:

$R_1$ and $R_2$ are each independently hydrogen, straight-chain or branched-chain alkyl, optionally substituted or unsubstituted aryl or heteroaryl;

$Z_1$ is a straight- or branched-carbon chain connecting to the nitrate ester group of $R_3$, wherein $Z_1$ can be substituted with heteroatom, alkyl, aryl and heteroaryl, and $Z_1$ can have one to six carbon atoms, for example, 1-6, 1-5, 2-6, 2-5, 2-4 or 3-6.

Of the compounds of formula (II), preferably, at least one of $R_1$ and $R_2$ is hydrogen.

Of the compounds of formula (II), preferably, $R_2$ is hydrogen, $R_1$ is a straight-chain or branched-chain alkyl, and the number of carbon atoms contained in $Z_1$ and $R_3$ together is no less than 3, preferably no less than 4, such as 4-6.

Of the compounds of formula (II), further preferably, $R_1$ and $R_3$ are each a nitrate ester group, and thus the compounds have a structure of formula (III):

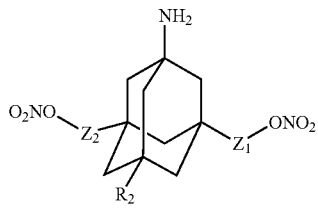

(III)

wherein:

$R_2$ is hydrogen, straight-chain or branched-chain alkyl, optionally substituted or unsubstituted aryl or heteroaryl;

$Z_1$ and $Z_2$ are each independently a straight- or branched-carbon chain connecting to a nitrate ester group, wherein $Z_1$ and $Z_2$ each independently can be substituted with heteroatom, alkyl, aryl and heteroaryl, and $Z_1$ and $Z_2$ each independently can have one to six carbon atoms, for example, 1-6, 1-5, 2-6, 2-5, 2-4 or 3-6.

The compounds of formula (III), preferably, are selected from the group consisting of:

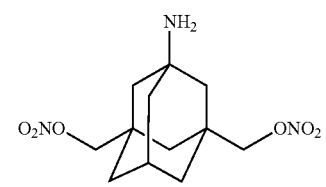

NM-008

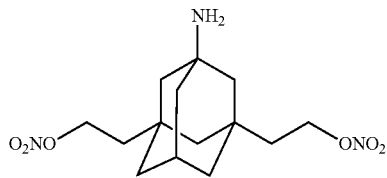

NM-009

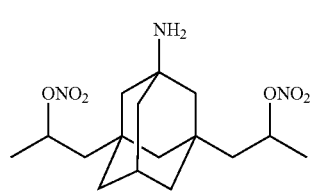

NM-010

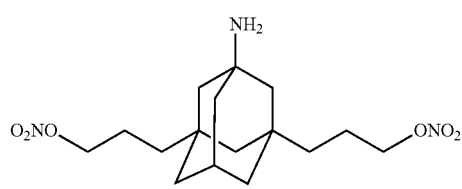

NM-011

-continued

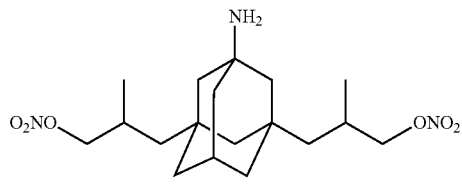

NM-012

Of the compounds of formula (I), further preferably, $R_1$, $R_2$ and $R_3$ are each a nitrate ester group, and thus the compounds have a structure of formula (III):

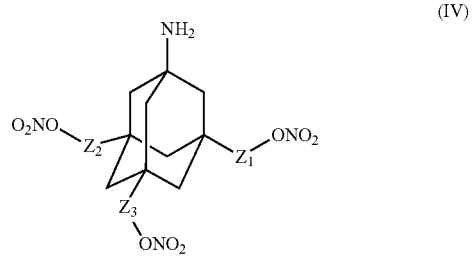

(IV)

wherein:

$Z_1$, $Z_2$ and $Z_3$ are each independently a straight- or branched-carbon chain connecting to the nitrate ester group of $R_1$, $R_2$ and $R_3$ respectively, wherein $Z_1$, $Z_2$ and $Z_3$ each independently can be substituted with heteroatom, alkyl, aryl and heteroaryl, and $Z_1$, $Z_2$ and $Z_3$ independently have have one to six carbon atoms, for example, 1-6, 1-5, 2-6, 2-5, 2-4 or 3-6.

In some preferred embodiments, the compounds of formula (I) include, but not limited, specific structures below:

NM-001

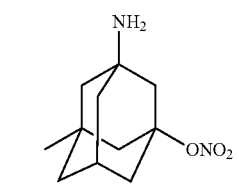

NM-002

NM-003

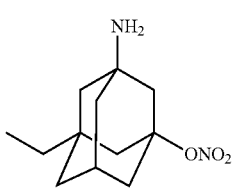

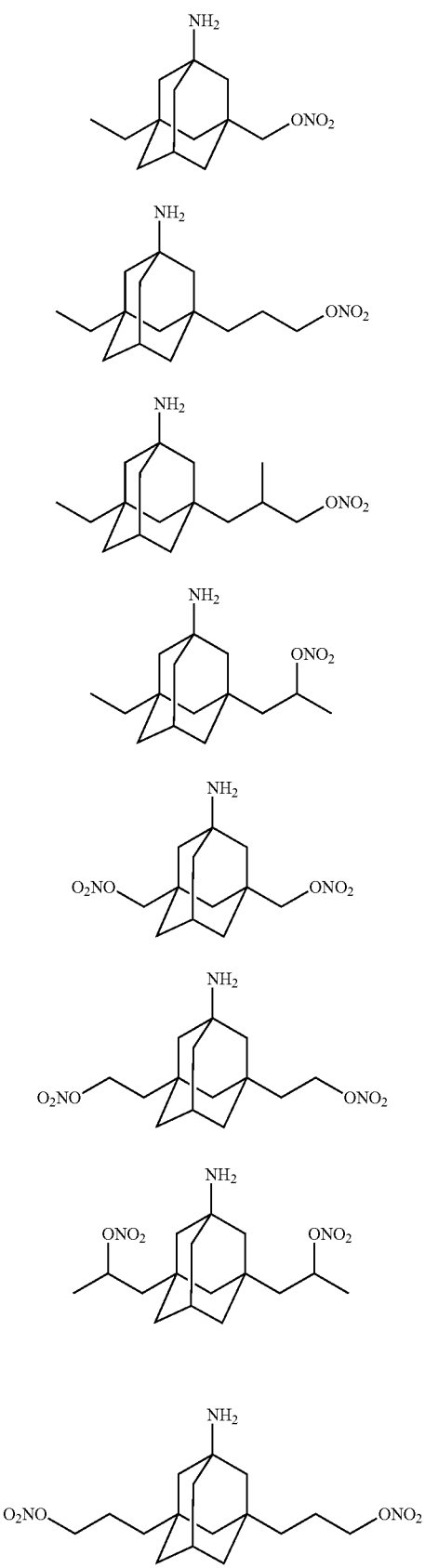

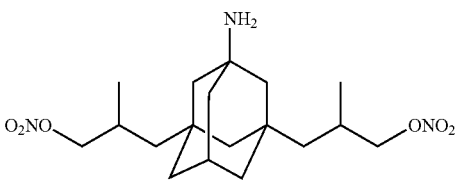

The present invention further provided a method for preparation of amantadine derivatives. The method comprises: using starting materials of adamantine optionally substituted or unsubstituted with bromo, alkyl or alkyl carboxylic group, introducing a amino group via Ritter reaction, and then forming a nitrate ester group on a substituted side chain of the amantadine via esterification of a hydroxy attached on adamantyl ring by using fuming nitric acid.

The compounds of the invention are effective for the protection of cells especially nerve cells, and can be used in manufacture of supplements or medicaments. The medicaments can include a therapeutically effective amount of the compound described herein with the structure of formula (I) or pharmaceutically acceptable salt thereof.

The compounds of the invention showed mechanisms of multiple functions, including the functions of inhibiting NMDA, releasing NO, inhibiting calcium influxes, removing radicals and protection of cells especially nerve cells. Thus, the compounds may be used for preparing cell protecting medicaments for prevention or treatment of diseases related to elevated calcium ions, excessive production of free radicals or excessive activation of NMDA receptors, such as Alzheimer's disease, Parkinson's disease, stroke, Huntington's disease, amyotrophic lateral sclerosis, myasthenia gravis, glaucoma, vascular dementia, subarachnoid hemorrhage, pulmonary arterial hypertension, chronic obstructive pulmonary disease, acute lung injury, bronchial asthma, and so on. The methods for prevention or treatment of such diseases comprise administering to a patient the medicaments prepared from the compounds containing an effective amount of the compounds of formula (I) to (V) described herein or pharmaceutically acceptable salt thereof, or a drug complex thereof.

The following definitions are used to describe and define the meaning and scope of the terms used herein.

As used herein, the term "alkyl" refers to unsubstituted or substituted straight, branched or cyclic alkyl chain having up to 10 carbon atoms. Straight-chain alkyl groups include, for example, saturated alkyl groups such as methyl, ethyl, n-propyl, n-butyl, n-pentyl, n-hexyl, n-heptyl and n-octyl, and unsaturated alkyl groups such as those containing ethylenic, acetylenic, carbonyl and cyano groups. Branched-chain alkyl groups include, for example, isopropyl, butyl, isobutyl, tert-butyl and neopentyl. Cyclic alkyl ("cycloalkyl") groups include, for example, cyclopropyl, cyclobutyl, cyclopentyl and cyclohexyl. Alkyl can have one or more hydrophobic substituents. The non-limiting examples of the substituents include $N(CH_3)_2$, F, Cl, Br, I, $OCH_3$, $CO_2CH_3$, CN, aryl and heteroaryl. The term "alkyl" also refers to unsubstituted or substituted straight, branched or cyclic alkyl having up to 10 carbon atoms and at least one heteroatom (e.g., nitrogen, oxygen or sulfur) therein. The straight alkyl includes, for example, $CH_2CH_2OCH_3$, $CH_2CH_2N(CH_3)_2$ and $CH_2CH_2SCH_3$. The branched alkyl includes, for example, $CH_2CH(OCH_3)CH_3$, $CH_2CH(N$ $(CH_3)_2)CH_3$ and $CH_2CH(OCH_3)CH_3$. The cyclic alkyl includes, for example, six-membered rings, such as $CH(CH_2CH_2)_2O$, $CH(CH_2CH_2)_2NCH_3$ and $CH(CH_2CH_2)_2S$, and the corresponding five-membered rings.

The term "aryl" refers to unsubstituted or substituted aromatic, carbocyclic group and heteroaryl. An aryl group can be either monocyclic or fused polycyclic. The aryl can be substituted with one or more substituents, including but not limited to $N(CH_3)_2$, F, Cl, Br, I, $OCH_3$, $CO_2CH_3$, CN, aryl and heteroaryl.

Heteroaryl can be a substituted or unsubstituted monocyclic or polycyclic group having at least one heteroatom, such as nitrogen, oxygen and sulfur. For example, a typical heteroaryl groups containing one or more nitrogen atoms may include, for example, tetrazolyl, pyrrolyl, pyridyl (such as pyrid-4-yl, pyrid-3-yl, pyrid-2-yl), pyridazinyl, indyl, quinolyl (such as quinol-2-yl, quinol-3-yl), imidazolyl, isoquinolyl, pyrazolyl, pyrazinyl, pyrimidinyl, pyridonyl or pyridazinyl; a typical hetroaryl having one oxygen atom includes fur-2-yl, fur-3-yl or benzofuryl; a typical hetroaryl containing one surfur atom may include, for example, thienyl, benzothienyl; a typical heteroaryl group containing an oxygen atom may include, for example, 2-furyl, 3-furyl or benzofuryl; a typical heteroaryl comprising more than one kind of heteroatoms includes furoazetidinyl, oxazolyl, isoxazolyl, thiazolyl and phenothioxinyl. The hetercycle group can be substituted by one or more substituents. Those substituents include O-alkyl, NH-alkyl, N (alkyl)$_2$, NHC(O)alkyl, F, Cl, Br, I, OH, $OCF_3$, $CO_2$-alkyl, CN, and aryl or polyaryl group.

The term "pharmaceutically acceptable" means that a compound has no unacceptable toxicity in a salt or excipient. The pharmaceutically acceptable salts include inorganic anions such as chlorine ion, bromine ion, iodine ion, sulfuric acid radical, sulfurous acid radical, nitric acid radical, nitrous acid radical, phosphoric acid radical, hydrogen phosphoric acid radical and the like. Organic anions include acetic acid radical, pyruvic acid radical, propionic acid radical, cinnamic acid radical, tosylic acid radical, citric acid radical, lactic acid radical, gluconic acid radical and the like. Pharmaceutically acceptable excipients are described below (see also, E. W. Martin, in Remington's Pharmaceutical Sciences Mack Publishing Company (1995), Philadelphia, Pa., 19$^{th}$ ed).

The novel compounds of the present invention comprise those of formulas (I) to (VIII) described above. The compounds also have at least one of the substituents selected from amido, aster and nitrate group on the amantadine structure, and thus those compounds have multifunctional mechanisms to inhibit the monoamine oxidase and cholinesterase, release NO, release H$_2$S and scavenge free radicals, and have a good protective effect to cells, especially the nerve cells. The compounds can be used in preparation of medicaments with protective effect of cells, and can be used for the prevention and treatment of the diseases related to monoamine oxidase, cholinesterase or free radicals, while such diseases are generally referred to those related to neurodegeneration and free radicals and the like. Such diseases include, but not limited to, the diseases related to monoamine oxidase, such as Parkinson's disease, Alzheimer's disease, dementia, hypertension, diarrhea, depression, asthma and allergies; the diseases related to cholinesterase, such as Alzheimer's disease, Parkinson's disease, Huntington's disease, amyotrophic lateral sclerosis, myasthenia gravis, glaucoma, hyperthyroidism, hypertension, bronchial asthma, IV hyperlipoproteinemia type renal and kidney failure; the diseases related to NO or oxidative stress damage or free radicals, such as stroke, brain trauma, epilepsy, Parkinson's disease, Huntington's disease, amyotrophic lateral sclerosis, Alzheimer's disease, hypoxic-ischemic brain damage, cerebral hemorrhage, dementia, ischemic heart disease, blood clots, atherosclerosis, hypercholesterolemia, emphysema, cataracts, diabetes, acute pancreatitis, alcohol-induced liver disease, kidney damage and cancer; the diseases related to H$_2$S, such as cardiovascular disease, inflammation, atherosclerosis, diabetes, Alzheimer's disease, Parkinson's disease, obesity, cancer, stroke, and traumatic brain damage; and also the diseases related to neurodegeneration such as cerebral ischemia, Parkinson's disease, Alzheimer's disease, amyotrophic lateral sclerosis, ataxia telangiectasia, bovine spongiform encephalopathy, Creutzfeldt-Jakob disease, spinocerebellar ataxia, multiple sclerosis, primary lateral sclerosis, and spinal muscular atrophy.

The present invention provided compounds having an ester group (includes an optionally substituted or unsubstituted carbamate group), amino and/or nitrate ester group, and derivatives thereof, and the compounds can be administered to patients in the form of a pharmaceutically acceptable salt or a pharmaceutical complex. Certain complex may need to form a pharmaceutical composition with a suitable carrier or excipient. The term "therapeutically effective amount" refers to an amount of the compounds that is necessary to achieve a desired effect.

A variety of preparations can be used to formulate pharmaceutical compositions containing the compounds with multiple functions of mechanisms, including solid, semi solid, liquid and gaseous forms (Remington's Pharmaceutical Sciences, Mack Publishing Company (1995), Philadelphia, Pa., 19$^{th}$ ed). Tablets, pills, granules, dragees, gels, slurries, ointments, solutions, suppositories, injections, inhalants and aerosols are examples of such formulations. The formulations can be administered in either a local or systemic manner or in a depot or sustained release fashion. Administration of the composition can be performed in a variety of ways. Among others, oral, buccal, rectal, parenteral, intraperitoneal, intradermal, transdermal and intratracheal means can be used.

When the compounds and derivatives described herein are given via injection, they can be formulated by dissolving, suspending or emulsifying it in an aqueous or nonaqueous solvent. Vegetable or similar oils, synthetic aliphatic acid glycerides, esters of higher aliphatic acids and proylene glycol are examples of nonaqueous solvents. The compound is preferably formulated in aqueous solutions such as Hank's solution, Ringer's solution or physiological saline buffer.

When the compounds and derivatives described herein are given orally, they can be formulated through combination with pharmaceutically acceptable carriers that are known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxyproylmethyl-cellulose, sodium carboxymethylcellulose and polyvinylpyrrolidone (PVP).

The compounds described herein are can also be delivered in an aerosol spray preparation from a pressurized pack and a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Pharmaceutical compositions according to the present invention contain a therapeutically effective amount of the compounds of multiple mechanisms. The amount of the compound will depend on the patient being treated. The patient's weight, severity of illness, manner of administration and judgment of the prescribing physician should be taken into account in deciding the proper amount. The determination of a therapeutically effective amount of the compounds described herein should be made by an experienced physician.

Although a therapeutically effective amount of the compound described herein or its derivative will vary according to the patient being treated, suitable doses will typically be in the range between about 10 mg and 10 g of the compound.

The present invention has the advantages over the prior art: the present invention provides substances with novel structures and multiple mechanisms or functions, and such substances can be used for inhibiting NMDA, releasing NO, inhibiting calcium influxes, removing radicals and protection of cells especially nerve cells. Thus, the compounds may be used for preparing cell protecting medicaments for prevention or treatment of diseases, which usually include: neuro-degeneration related diseases such as Alzheimer's disease and Parkinson's disease, and free radical related diseases such as stroke and heart disease.

BRIEF DESCRIPTION OF THE DRAWINGS

FIG. 3 is a scheme of exemplary Synthesis of compound NM-005.

FIG. 4 is a scheme of exemplary Synthesis of compound NM-008.

FIG. 5 is a scheme of exemplary Synthesis of compound NM-009.

FIG. 6 is a scheme of exemplary Synthesis of compound NM-011.

FIGS. 18A-1 to 18A-3 and 18B-1 to 18B-3 illustrate that compound MN-08 inhibits LPS-induced secretion of proinflammatory cytokines TNF-α and IL-1β from supernatants of RAW 264.7 cells.

FIGS. 19A-1 to 19A-2, 19B-1 to 19B-3, and 19C illustrate the regulation of MN-08 on LPS-induced NF-kB signaling pathway-related proteins and MAPK signaling pathway-related proteins in RAW 264.7 cells.

FIG. 20 is a graph showing the protective effect of amantadine mononitrate compounds on cerebellar granule cells.

FIG. 25A-H illustrates the effect of compound MN-08 on peripheral blood pressure and heart rate.

FIG. 26A-D illustrates the effect of compound MN-08 on regional cerebral blood flow.

FIGS. 27A and 27B illustrate the protective effect of compound MN-08 on retinal ganglion cells in a rat acute glaucoma model.

FIGS. 30A to 30C illustrate the effect of compound MN-08 on learning and memory cognition in autonomous exercise and new object recognition systems in vascular dementia model rats.

FIG. 31 illustrates the effect of compound MN-08 on behavioral behavior in rats with subarachnoid hemorrhage.

DETAILED DESCRIPTION OF THE EMBODIMENTS

Figure 1:
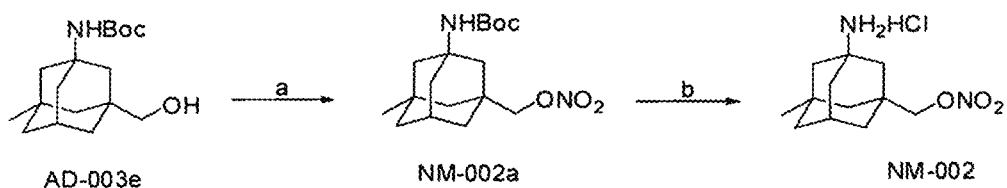
FIG. 1 is a scheme of exemplary Synthesis of compound NM-002.
Figure 2:
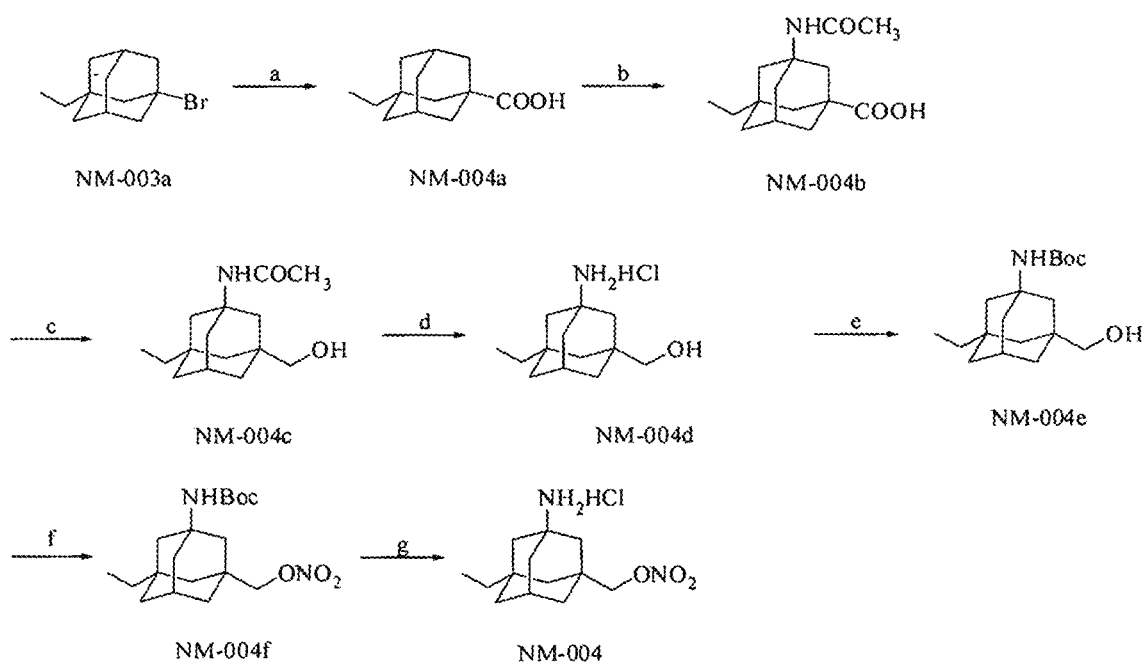
FIG. 2 is a scheme of exemplary Synthesis of compound NM-004.
Figure 7:
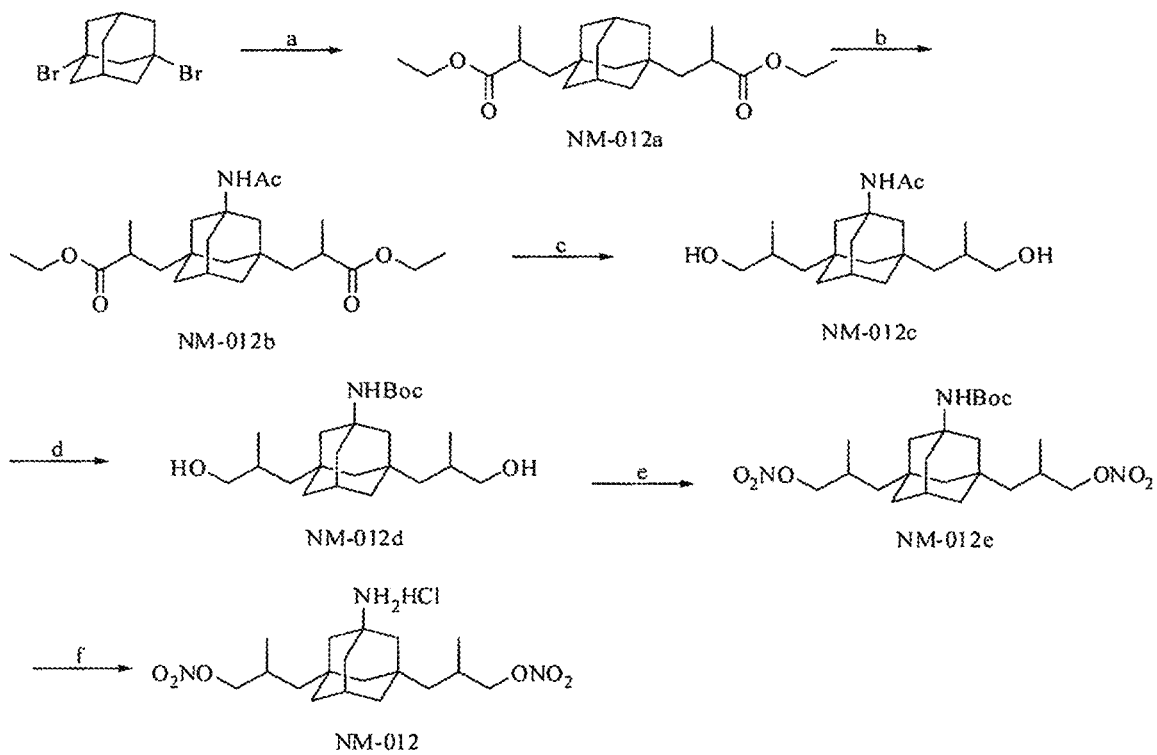
FIG. 7 is a scheme of exemplary Synthesis of compound NM-012.

The following examples are intended for illustration only and are not intended to restrict the scope of the present invention in any way.

EXAMPLE 1

Synthesis of Compound NM-002a

Compound AD-003e (1.48 g, 5 mmol) was dissolved in 30 mL of dry methylene chloride and cooled with an ice-water bath. A mixed solution (3 mL) of acetic anhydride and fuming nitric acid (3:2 by volume) was added. The reaction continued for 10-15 minutes with an ice-water bath. The reaction mixture was poured into 30 mL of 1N sodium bicarbonate solution, and then methylene chloride was separated, and the aqueous layer was extracted with dichloromethane (20 mL×3). The organic layers were combined, washed with water (30 mL), dried over anhydrous sodium sulfate, and the filtered. The dichloromethane layer was distilled under reduced pressure to obtain a crude product as colorless oil, which was separated by silica column chromatography (petroleum ether: dichloromethane=10:1) to give NM-002a as a colorless oil (1.07 g, 62.9%). ESI-MS: m/z 340.2 ([M]$^+$). $^1$H-NMR (DMSO-d6, ppm): 0.83 (s, 3 H), 1.15-1.24 (m, 2 H), 1.26-1.47 (m, 14 H), 1.56-1.80 (m, 5 H), 2.06-2.14 (m, 1 H), 4.22 (s, 2 H), 6.51 (s, 1 H).

EXAMPLE 2

Synthesis of Compound NM-002

To compound NM-002a (680 mg, 2 mmol) was added a saturated solution of hydrogen chloride in ether (5 mL). The reaction was run at room temperature, and monitored with TLC. When the reaction was completed, a white solid was precipitated. The resulting mixture was filtered, and a white solid was obtained and washed with dry ether to give pure NM-002 (390 mg, 70.7%). ESI-MS: m/z 341.0 ([M+H]$^+$). $^1$H-NMR (DMSO-d6, ppm): 0.88 (s, 3 H), 1.19-1.29 (m, 2 H), 1.30-1.38 (m, 2 H), 1.38-1.52 (m, 4 H), 1.54-1.64 (m, 2 H), 1.66-1.73 (m, 2 H), 2.18-2.24 (m, 1 H), 4.29 (s, 2 H), 8.11 (s, 3 H).

EXAMPLE 3

Synthesis of Compound NM-004a

In a 50 mL round-bottom flask placed in an ice water bath was added 20 mL of concentrated sulfuric acid, 2 mL of n-hexane and 970 mg of compound NM-003a (4 mmol). Being kept with the ice-water bath, formic acid (1.8 mL) was slowly added dropwise, and then the reaction was run for 3 hours with the ice-water bath. The reaction mixture was poured into 100 mL of ice water, and a solid was precipitated. The resulting mixture was allowed to stand and then was filtered under vacuum to give a pale yellow solid. The solid was dried, dissolved in ethyl acetate, and basified to about pH 9-10 with an aqueous solution of sodium hydroxide. Aqueous layer was separated, and the organic layer was extracted with aqueous solution of sodium hydroxide (30 mL×3). The aqueous layers were combined, and then acidified with a solution of dilute hydrochloric acid to about pH 3. The resulting materials were filtered under vacuum, and dried to give a pure compound NM-004a (640 mg, 77%). ESI-MS: m/z 207 ([M−H]$^−$). $^1$H-NMR (DMSO-d6, ppm): 0.76 (t, 3 H, J=7.5 Hz), 1.11 (q, 2 H, J=7.5 Hz), 1.31-1.44 (m, 4 H), 1.47 (s, 2 H), 1.51-1.64 (m, 2 H), 1.66-1.81 (m, 4 H), 2.01 (m, 2 H), 11.99 (s, 1 H).

EXAMPLE 4

Synthesis of Compound NM-004b

In a 50 mL round-bottom flask was placed 624 mg of compound NM-004a (3 mmol), which was cooled with an ice water bath. A concentrated nitric acid (0.55 mL) was added with stirring. To the mixture, a concentrated sulfuric acid (1.3.5 mL) was added dropwise, and the reaction was kept in an ice bath for 1 hour. Acetonitrile (2.5 mL, 4.8 mmol) was added dropwise, and the reaction was kept with an ice bath for 1 hour. The reaction mixture was poured into 20 mL of ice water, stirred vigorously for 30 minutes, and allowed to stand overnight. A white solid was precipitated. The resulting mixture was filtered under vacuum, and the solid was washed with suitable amount of water and dried to give the compound NM-004b (580 g, 73%) to be used directly in the next reaction step without further purification. ESI-MS: m/z 266 ([M+H]$^+$). $^1$H-NMR (DMSO-d6, ppm): 0.74 (t, 3 H, J=7.5 Hz), 1.15 (q, 2 H, J=7.5 Hz), 1.26-1.35 (m, 2 H), 1.36-1.47 (m, 2 H), 1.52-1.70 (m, 4 H), 1.72-1.86 (m, 5 H), 1.88-1.98 (m, 2 H), 2.13 (m, 1 H), 7.43 (s, 1 H).

EXAMPLE 5

Synthesis of Compound NM-004c

A compound NM-004b (878 mg, 3.3 mmol) was dissolved in 10 mL of dried tetrahydrofuran, being cooled with an ice water bath. To the mixture was added sequentially 0.5 mL of triethylamine and 0.5 mL of ethyl chloroformate. After 30 minutes, the ice bath was removed. The reaction was run for 4 hours at room temperature. The resulting materials were filtered, and the residue was washed with an appropriate amount of tetrahydrofuran. The filtrate was collected, to which was added 1.5 g of sodium borohydride. Then 1 mL of water was added dropwise with dropping funnel within 1 hour. Then, the reaction continued at room temperature for 1 hour and monitored with TLC. After the reaction being completed, 30 mL of water was added, and tetrahydrofuran was evaporated to dryness in a rotavap under reduced pressure. The aqueous layer was extracted with ethyl acetate (20 mL×4). The organic layers were combined, and washed with 0.5 N hydrochloric acid (25 mL), and saturated aqueous solution of sodium chloride and water, and dried over anhydrous sodium sulfate. The resulting solution was evaporated under reduced pressure to obtain a crude product as an oil, which was separated by silica column chromatography (petroleum ether: ethyl acetate=1:1) to give NM-004c as a white solid (348 mg, 42%). ESI-MS: m/z 252.2 ([M+H]$^+$). $^1$H-NMR (DMSO-d6, ppm): 0.76 (t, 3 H, J=7.5 Hz), 1.03-1.20 (m, 4H), 1.28 (m, 4 H), 1.58 (m, 4 H), 1.75 (m, 5 H), 2.09 (s, 1 H), 3.02 (d, 2 H, J=5.5 Hz), 4.38 (t, 1 H, J=5.5 Hz), 7.33 (s, 1 H).

EXAMPLE 6

Synthesis of Compound NM-004d

In a 250 mL round-bottom flask were added compound NM-004c (1.26 g, 5 mmol), solid of sodium hydroxide (3 g) and diethylene glycol (20 mL). The reaction mixture was refluxed at 170° C. for 15 hours, and then cooled to room temperature. The resulting materials were poured into 40 g of crushed ice. After stirring evenly, the mixture was extracted with ethyl acetate (20 mL×4). The organic layers were combined, and washed with 30 mL of water and 30 mL of saturated solution of sodium chloride, and dried with anhydrous sodium sulfate. The solvent was evaporated to give crude product as a pale yellow oil. The crude product was dissolved in 50 mL of dry ethyl acetate, introduced with dry HCl with stirring, and a large amount of white solid was precipitated. After filtered under vacuum, the solid was washed with appropriate amount of dry ethyl acetate to give NM-004d as a white solid (850 mg, 69.4%). ESI-MS: m/z 210.3 ([M+H]$^+$). $^1$H-NMR (DMSO-d6, ppm): 0.74 (t, 3 H, J=7.6 Hz), 1.15 (q, 2 H, J=7.6 Hz), 1.26-1.35 (m, 2 H), 1.36-1.47 (m, 2 H), 1.53-1.68 (m, 4 H), 1.74-1.85 (m, 3 H), 1.88-1.96 (m, 2 H), 2.13 (m, 1 H), 7.43 (s, 3 H).

EXAMPLE 7

Synthesis of Compound NM-004e

A compound NM-004d (2.45 g, 10 mmol) was dissolved in 20 mL of water, basified to about pH 10 with a solution of sodium hydroxide, and extracted with ethyl acetate (30 mL×4). The organic layers were combined, washed with 30 mL of water, and dried with anhydrous sodium sulfate. The solvent was removed under reduced pressure to give free amine as a colorless oil (1.57 g, 7.5 mmol). Without further purification, the oil was dissolved in 50 mL of dry tetrahydrofuran, and were added in order with 1.56 g of triethylamine (15.6 mmol), 2.55 g of Boc anhydride (11.7 mmol) and 10 mg of DMAP. The reaction was run for 5 hours at room temperature and monitored with TLC. After the reaction being completed, 30 mL of saturated ammonium chloride solution was added to quench the reaction. The solvent was evaporated to dryness under reduced pressure, and the residue was extracted with ethyl acetate (50 mL×4). The organic layers were combined and washed with 30 mL of 0.1 N hydrochloric acid and 30 mL of saturated aqueous sodium chloride solution, and dried with anhydrous sodium sulfate. The solvent was evaporated to dryness under reduced pressure to give a crude product as a colorless oil, which was separated by silica column chromatography (petroleum ether: ethyl acetate=1:1) to give NM-004e as a white solid (1.58 g, 68%). ESI-MS: m/z 310.3 ([M+H]$^+$). $^1$H-NMR (DMSO-d6, ppm): 0.75 (t, 3 H, J=7.5 Hz), 1.03-1.19 (m, 4 H), 1.24 (m, 4 H), 1.36 (s, 9 H), 1.44-1.58 (m, 4 H), 1.52-1.73 (m, 2 H), 2.08 (s, 1 H), 3.02 (d, 2 H, J=5.5 Hz), 4.38 (t, 1 H, J=5.5 Hz), 6.36 (s, 1 H).

EXAMPLE 8

Synthesis of Compound NM-004f

Compound NM-004e (620 mg, 2 mmol) was dissolved in 10 mL of dry methylene chloride, and cooled with an ice-water bath. A mixed solution (2 mL) of acetic anhydride and fuming nitric acid (in a ratio of 3:2 by volume) was added. The reaction was run with an ice-water bath for 10-15 minutes. The reaction solution was added to 10 mL of 1 N sodium bicarbonate solution, and the dichloromethane was separated, and the aqueous layer was extracted with dichloromethane (10 mL×3). The organic layers were combined, washed with 10 mL of water, dried with anhydrous sodium sulfate, and filtered. The solvent was distilled under reduced pressure to give crude product as a colorless oil, which was separated by silica column chromatography (petroleum ether: dichloromethane=10:1) to give NM-004f as a colorless (505 mg, 73.4%). ESI-MS: m/z 377.2 ([M+Na]$^+$). $^1$H-NMR (DMSO-d6, ppm): 0.76 (t, 3 H, J=7.5 Hz), 1.08- 1.23 (m, 4 H), 1.26-1.49 (m, 14 H), 1.56-1.82 (m, 5 H), 2.12 (m, 1 H), 4.23 (s, 2 H), 6.50 (s, 1 H).

EXAMPLE 9

Synthesis of Compound NM-004

To compound NM-004f (710 mg, 2 mmol) was added 5 mL of hydrogen chloride saturated ether solution, and the reaction was run at room temperature. When the reaction was completed, a white solid was precipitated. The resulting materials were filtered and a white solid was obtained and washed with anhydrous ether to give pure NM-004, which was then dried to give NM-004 (380 mg, 65.5%). ESI-MS: m/z 255.1 ([M+H]$^+$). $^1$H-NMR (DMSO-d6, ppm): 0.78 (t, 3 H, J=7.5 Hz), 1.15-1.28 (m, 4 H), 1.30-1.39 (m, 2 H), 1.40-1.55 (m, 4 H), 1.57-1.67 (m, 2 H), 1.71 (s, 2 H), 2.23 (m, 1 H), 4.30 (s, 2 H), 8.21 (s, 3 H).

EXAMPLE 10

Synthesis of Compound NM-005a

Compound NM-003a (3.66 g, 15.0 mmol) was dissolved in 45 mL of dry toluene, and 0.122 g of AIBN (0.74 mol), 4.95 g of n-Bu3SnH (16.7 mmol), and 3.10 g of ethyl acrylate (31.0 mmol) were added in order. The reaction was refluxed at 110° C. under nitrogen for 3 hours and monitored with TLC. After the reaction being completed, the reaction mixture was cooled and was poured into 105 mL of 0.2 M aqueous ammonia, stirred for 1 hour, and extracted with ethyl acetate (100 mL×4). The organic layers were combined and dried with anhydrous sodium sulfate. The resulting materials were filtered, and the solvent was removed under reduced pressure to give a colorless transparent liquid, which was separated by silica column chromatography (petroleum ether: ethyl acetate=6:1) to give NM-005a as a colorless transparent liquid (2.50 g, 62.8%). $^1$H-NMR (DMSO-d$_6$, ppm): 0.72 (t, 3 H, J=7.5 Hz), 1.10 (m, 4 H), 1.17 (t, 3 H, J=7.8 Hz), 1.32 (m, 10 H), 1.53 (s, 2 H), 1.97 (s, 2 H), 2.21 (t, 2 H, J=8.1 Hz), 4.02 (q, 1 H, J=7.2 Hz).

EXAMPLE 11

Synthesis of Compound NM-005b

To the compound NM-005a (2.50 g, 9.5 mmol) were added 60 mL of methanol and 5 mL of water. The mixture was stirred to be dissolved, and 3.2 g of potassium hydroxide (57 mmol) was added. The reaction was run at room temperature for 12 hours and monitored with TLC. After the reaction being completed, the solvent was removed under reduced pressure. To the residue was added 30 mL of water, and was extracted with 20 mL of ethyl acetate to remove organic impurities. The aqueous layer was adjusted to pH 1-2 with concentrated hydrochloric acid, and then a large amount of white solid was precipitated. The resulting materials were filtered under vacuum, and the filter cake was washed with small amount of water, and dried to give NM-005b as a white solid (1.60 g, 71.6%). ESI-MS: m/z 237.1 ([M+H]$^+$). $^1$H-NMR (DMSO-d$_6$, ppm): 0.75 (t, 3 H, J=7.5 Hz), 1.10 (m, 4 H), 1.32 (m, 10 H), 1.54 (s, 2 H), 1.97 (s, 2 H), 2.14 (t, 2 H, J=8.1 Hz), 11.98 (s, 1 H).

EXAMPLE 12

Synthesis of Compound NM-005c

Compound NM-005b (1.6 g, 6.8 mmol) was placed in a 50 mL round-bottom flask, and cooled with an ice bath.

Concentrated nitric acid (1.1 mL) was added with stirring. To the mixture was added dropwise 6.8 mL of concentrated sulfuric acid, then reacted for 1 hour with an ice bath. To the reaction was slowly added dropwise 5 mL of acetonitrile, and run in an ice bath for 1 hour. The reaction solution was poured into 30 mL of ice water, and stirred vigorously for 30 minutes. The resulting materials were extracted with ethyl acetate (50 mL×5), and the organic layers were combined, dried with anhydrous sodium sulfate, and filtered. The solvent was removed under reduced pressure to give a colorless viscous liquid, which was separated by silica column chromatography (ethyl acetate as eluent) to give NM-005c as a colorless transparent viscous semi-solid (1.60 g, 80.6%). $^1$H-NMR (DMSO-$d_6$, ppm): 0.75 (t, 3 H, J=7.5 Hz), 1.11 (m, 4 H), 1.28 (m, 6 H), 1.54 (m, 4 H), 1.73 (m, 5 H), 2.08 (s, 1 H), 2.16 (m, 2 H), 3.16 (s, 1 H), 1.77 (m, 1 H), 4.38 (m, 2 H), 4.40 (s, 1 H).

EXAMPLE 13

Synthesis of Compound NM-005d

Compound NM-005c (2.8 g, 9.5 mmol) was dissolved in 10 mL of dry tetrahydrofuran with cooling in an ice bath. Then 1.5 mL of triethylamine and 1.5 mL of ethyl chloroformate (15.8 mmol) were added in order, and, after 30 minutes the ice bath was removed. The reaction was run at room temperature for 4 hours and filtered, and the filter cake was washed with tetrahydrofuran. The filtrate was collected, and 2.7 g of sodium borohydride (0.07 mol) was added and then 1.8 mL of water was added dropwise. The reaction was run at room temperature for 2 hours, and then 50 mL of water was added. The solvent was removed under reduced pressure. The aqueous layer was extracted with ethyl acetate (50 mL×5), and the organic layers were combined, washed with a saturated aqueous solution of sodium chloride, and dried with anhydrous sodium sulfate. The resulting mixture was filtered, and the solvent was removed under reduced pressure to give a crude product as an oil, which was then separated by silica column chromatography (methanol: ethyl acetate=1:6) to give NM-005d as a colorless transparent viscous semi-solid (1.7 g, 63.75%). ESI-MS: m/z 280.1 ([M+H]$^+$). $^1$H-NMR (DMSO-$d_6$, ppm): 0.75 (t, 3 H, J=7.5 Hz), 1.11 (m, 4H), 1.36 (m, 6 H), 1.54 (m, 4 H), 1.73 (m, 5 H), 2.08 (s, 1 H), 2.18 (m, 2 H), 3.57 (m, 2 H).

EXAMPLE 14

Synthesis of Compound NM-005e

To a 100 mL round-bottom flask were added in order the compound NM-005d (1.7 g, 6.1 mmol), sodium hydroxide (5.5 g, 0.14 mol) and diethylene glycol (35 mL). The mixture was refluxed at 175° C. for 16 h, and then cooled to room temperature. The resulting materials were poured into 50 g of crushed ice with stirring, and extracted with ethyl acetate and methyl tert-butyl ether (4:1 by volume, 50 mL×6). The organic phases were combined, and washed with saturated sodium chloride solution, and dried with anhydrous sodium sulfate. The resulting materials were filtered, and the solvent was removed under reduced pressure to give 1.1 g of brown liquid, to which, without further purification, a redistilled dry dichloromethane (50 mL) was added directly, and then 2.5 mL of triethylamine and 1.1 g of Boc anhydride (5 mmol) were added in order. The reaction was stirred at room temperature for 5 hours, and monitored with TLC. After the reaction being completed, the reaction solution was washed several times with a saturated sodium chloride solution. The organic phase was dried with anhydrous sodium sulfate. The resulting materials were filtered, and the solvent was removed under reduced pressure to give a brown oil, which was separated by silica column chromatography (petroleum ether: ethyl acetate=1:5) to give NM-005e as a colorless liquid (0.48 g, 23.38%). $^1$H-NMR (CDCl$_3$-d, ppm): 0.80 (t, 3 H, J=7.5 Hz), 1.14 (m, 2 H), 1.20 (m, 4 H), 1.33 (m, 6 H), 1.43 (s, 9 H), 1.51 (m, 2 H), 1.61 (m, 2 H), 1.72 (m, 1 H), 1.78 (m, 2 H), 2.17 (m, 1 H), 3.61 (m, 2 H, J=6.3 Hz), 4.43 (s, 1 H).

EXAMPLE 15

Synthesis of Compound NM-005f

Compound NM-005e (380 mg, 1.1 mmol) was dissolved in 8 mL of dry methylene chloride, and cooled with an ice bath. Then 1.2 mL of a mixed solution of acetic anhydride and fuming nitric acid (in a ratio of 3:2 by volume) was added. The reaction was run for 10-15 minutes, and monitored with TLC. After the reaction being completed, the reaction solution was poured into 40 mL of 1 N sodium bicarbonate solution, and extracted with dichloromethane continued (20 mL×3). The organic layers were combined, and washed with a solution of saturated sodium chloride, and dried with anhydrous sodium sulfate. The resulting materials were filtered, the solvent removed under reduced pressure to give a colorless oil, which was separated by silica column chromatography (petroleum ether: ethyl acetate=20:1) to give NM-005f as a colorless oil (230 m, 53.41%). $^1$H-NMR (CDCl$_3$-d, ppm): 0.76 (t, 3 H, J=7.5 Hz), 1.10 (m, 2 H), 1.23 (m, 6 H), 1.33 (m, 2 H), 1.40 (s, 9 H), 1.51 (m, 2 H), 1.68 (m, 4 H), 1.68 (m, 4 H), 1.77 (m, 1 H), 4.38 (m, 2 H), 4.40 (s, 1 H).

EXAMPLE 16

Synthesis of Compound NM-005

Compound NM-005f (110 mg, 0.29 mmol) was placed in a 25 mL round-bottom flask, and 10 mL of saturated hydrogen chloride solution was added. The reaction was run at room temperature for 30-45 minutes, and monitored with TLC. After the reaction being completed, the solvent was removed under reduced pressure to give a colorless oil. Then 20 mL of anhydrous ether was added and the solvent was removed under reduced pressure, which was repeated several times, until a solid was precipitated. The resulting materials were filtered, and the filter cake was washed with a small amount of anhydrous diethyl ether, and dried to give NM-005 as a white solid (32 mg, 39.4%). ESI-MS: m/z 283.1 ([M+H]$^+$). $^1$H-NMR (DMSO-$d_6$, ppm): 0.77 (t, 3 H, J=7.5 Hz). 1.18 (m, 6 H), 1.30 (m, 4 H), 1.46 (m, 4 H), 1.60 (m, 2 H), 1.67 (m, 2 H), 2.18 (m, 1H), 4.49 (t, 2 H, J=6.6 Hz), 8.18 (s, 3 H).

EXAMPLE 17

Synthesis of Compound NM-008a

In a two-necked round-bottom flask with a condenser was added 1,3-adamantanediol (8.4 g, 50 mmol), which cooled with an ice bath. Then 56 mL of concentrated sulfuric acid was added with stirring, and 5 mL of anhydrous acid was slowly added dropwise. After the addition, the mixture was maintained with an ice bath for 2 hours. The reaction was run at room temperature for 10 hours. The pale yellow viscous transparent reaction solution was slowly poured into 200 g of ice water, and then a large amount of white solid was precipitated. The resulting materials were filtered, and the filter cake was washed with water, and then dried to give compound NM-008a (8.9 g, 79.5%). ESI-MS: m/z 223.2 ([M−H]$^-$). H-NMR (DMSO-d6, ppm): 1.56-1.88 (m, 12 H), 2.06 (s, 2 H), 12.12 (s, 2 H).

EXAMPLE 18

Synthesis of Compound NM-008b

Compound NM-008a (2.24 g, 10 mmol) was dissolved in 100 mL of dry tetrahydrofuran, and cooled with an ice bath. Then 3.0 mL of triethylamine and 3.0 mL of ethyl chloroformate were added in order. The ice bath was removed 30 minutes later, and the reaction was run at room temperature for 4 hours. The resulting materials were filtered, and the filter cake was washed with tetrahydrofuran. The filtrate was collected, and to which 6 g of sodium borohydride was added, and 3 mL of water was slowly added with dropping funnel within 1 hour. After the water being added completely, the reaction was reacted at room temperature for 1 hour and monitored with TLC. When the reaction was completed, 50 mL of water was added, and organic phase was removed to dryness under reduced pressure. The aqueous layers were extracted with ethyl acetate (40 mL×4). The organic layers were combined, and were washed with 50 mL of 0.5 N hydrochloric acid and saturated sodium chloride aqueous solution and water, respectively, and then dried with anhydrous sodium sulfate. The solvent was evaporated under reduced pressure, to give a crude product as a white solid, which was washed with ethyl acetate to give NM-008b as a white solid (1.08 g, 55%). ESI-MS: m/z 274.2 ([M+2K]$^{2+}$). $^1$H-NMR (DMSO-d6, ppm): 1.14 (s, 2 H), 1.26-1.47 (m, 8 H), 1.54 (s, 2 H), 1.99 (m, 2 H), 2.99 (d, 4 H, J=5.5 Hz), 4.30 (t, 1 H, J=5.5 Hz).

EXAMPLE 19

Synthesis of Compound NM-008c

In a 25 mL round-bottom flask was placed with a white solid of compound NM-008b (784 mg, 4 mmol), then 5 mL of acetic anhydride was added with stirring. To the suspension was added 2-3 drops (catalytic amount) of perchloric acid. The reaction was run at room temperature for 3 hours. The reaction solution was poured into 20 g of ice water, and extracted with ethyl acetate (20 mL×3). The organic layers were combined and washed with 30 mL of 1 N sodium bicarbonate solution and 30 mL of water, and was dried with anhydrous sodium sulfate. The solvent was evaporated under reduced pressure to obtain a rude product as colorless oil. The crude product was separated by silica column chromatography (petroleum ether: ethyl acetate=10:1) to obtain NM-008c as a colorless oil (1.0 g, 90%). ESI-MS: m/z 298.3 ([M+H$_2$O]$^+$). $^1$H-NMR (DMSO-d6, ppm): 1.284 (s, 2 H), 1.36-1.52 (m, 8 H), 1.59 (s, 2 H), 2.02 (s, 8 H), 3.66 (s, 4 H).

EXAMPLE 20

Synthesis of Compound NM-008d

Compound NM-008c (840 mg, 3 mmol) was placed in a 25 mL round-bottom flask, and was cooled with an ice bath. Then 0.55 mL of concentrated nitric acid was added with stirring. To the mixture was slowly added 3.5 mL of concentrated sulfuric acid. The reaction was then run with an ice bath for 1 hour. Acetonitrile (2.5 mL, 4.8 mmol) was slowly added dropwise, the reaction was continued with an ice bath reaction for 1 hour. The reaction mixture was poured into 20 mL of ice water, and the aqueous layer was extracted with ethyl acetate. (20 mL×4). The organic layers were combined, and washed with 30 mL of 1 N sodium bicarbonate solution and 30 mL of water, and was dried with anhydrous sodium sulfate. The solvent was evaporated under reduced pressure to dryness to give a crude product as a colorless oil. The crudeproduct was separated by silica column chromatography (petroleum ether: ethyl acetate=1:3) to obtain compound NM-008d as an oil (425 mg, 42%). ESI-MS: m/z 360.3 ([M+Na]$^+$). $^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 21

Synthesis of Compound NM-008e

Compound NM-008d (670 mg, 2 mmol) was placed in a 25 mL round-bottom flask, and 10 mL of 18% HCl was added. The reaction was refluxed for 48 hours. Water was evaporated to dryness under reduced pressure to give a white solid, which was wished with ethyl acetate to obtain NM-008e (296 mg, 60%). ESI-MS: m/z 21.3 ([M+H]$^+$). $^1$H-NMR (DMSO-d6, ppm).

EXAMPLE 22

Synthesis of Compound NM-008f

Compound NM-008e (500 mg, 2 mmol) was placed in a 25 mL round-bottom flask, and 5 mL of DMF was added. Then triethylamine (800 mg, 8 mmol), Boc anhydride (650 mg, 3 mmol) and DMAP (2 mg) were added in order. The reaction was run at room temperature with stirring for 5 hours and monitored with TLC. After the reaction being completed, 20 mL of saturated ammonium chloride solution was added to quench the reaction. The solvent was evaporated to dryness under reduced pressure, and the aqueous layer was extracted with ethyl acetate (10 mL×4). Organic layers were combined, washed with 10 mL of 0.1 N hydrochloric acid and 10 mL of saturated aqueous sodium chloride solution, and dried with anhydrous sodium sulfate. The solvent was evaporated under reduced pressure to give a crude product as a colorless oil. The crude product was separated by silica column chromatography (petroleum ether: ethyl acetate=1:1) to obtain NM-008f as a white solid (404 mg, 65%). ESI-MS: m/z 312.3 ([M+H]$^+$). $^1$H-NMR (DMSO-d6, ppm): 1.07 (m, 2 H), 1.20-1.29 (m, 4 H), 1.39 (s, 9 H), 1.43-1.59 (m, 4 H), 1.62-1.72 (m, 2 H), 2.08 (m, 1 H), 3.02 (d, 4 H, J=5.5 Hz), 4.38 (t, 2 H, J=5.5 Hz), 6.39 (s, 1 H).

EXAMPLE 23

Synthesis of Compound NM-008g

Compound NM-008f (624 mg, 2 mmol) was dissolved in 10 mL of anhydrous dichloromethane, and cooled with an ice bath. Then, 2 mL of mixture solution of acetic anhydride and fuming nitric acid in a ratio 3:2 by volume was added. The reaction was run for 10-15 minutes with an ice bath. The reaction solution was poured into 10 mL of 1 N sodium bicarbonate solution. The solvent phase was separated, and the aqueous phase was extracted with dichloromethane (10 mL×3). Organic layers were combined and washed with 10 mL of water and dried with anhydrous sodium sulfate. After filtration, the filtrate was distilled under reduced pressure to obtain a crude product as a colorless oil, which was separated by silica column chromatography (petroleum ether: dichloromethane=10:1) to give NM-008g as a colorless oil (600 mg, 75%). ESI-MS: m/z 419.3 ([M+H]$^+$). $^1$H-NMR (DMSO-d6, ppm): 1.37 (s, 9 H), 1.40 (m, 6 H), 1.60 (m, 2 H), 1.72-1.82 (m, 4 H), 2.17 (m, 1 H), 4.23 (s, 4 H), 6.66 (s, 1 H).

EXAMPLE 24

Synthesis of Compound NM-008

To the compound NM-008g (401 mg, 1 mmol) was added 5 mL solution of saturated hydrogen chloride in ether. The reaction was at room temperature and monitored with TLC. After the reaction being completed, a white solid was precipitated. After being filtered, the white solid was washed with anhydrous ether to give a pure product, which was dried to give NM-008 (380 mg, 65.5%). ESI-MS: m/z 255.1 ([M+H]$^+$). $^1$H-NMR (DMSO-d6, ppm): 1.38-1.54 (m, 6 H), 1.60-1.77 (m, 6 H), 2.27 (m, 1 H), 4.32 (s, 4 H), 8.27 (s, 3 H).

EXAMPLE 25

Synthesis of Compound NM-009a

To 100 mL of tetrahydrofuran was added anhydrous 1,3-adamantane diacetic acid (2.52 g, 10 mmol) cooled with an ice bath. To the suspension were added triethylamine (3.0 mL) and ethyl chloroformate (3.0 mL) in order with an ice bath which was maintained for 30 minutes. Then the ice bath was removed, and the reaction was reacted for 4 hours at room temperature. The resulting materials were filtered, and the filter cake was washed with an appropriate amount of tetrahydrofuran. The filtrate was collected. To the filtrate was added 6 g of sodium borohydride, and then 3 mL of water was slowly added dropwise with dropping funnel within 1 hour. The reaction was run and monitored with TLC. After the reaction was completed, 50 mL of water was added to the reaction system. The solvent was evaporated under reduced pressure. The aqueous layer was extracted with ethyl acetate (40 mL×4). The organic layers were combined, and washed with 50 mL of 0.5 N hydrochloric acid, saturated sodium chloride aqueous solution and water, respectively. The mixture was dried with anhydrous sodium sulfate. The solvent was evaporated under reduced pressure to give a white solid crude product, to which was washed with ethyl acetate to give NM-009a as a white solid (1.43 g, 63.8%). ESI-MS: m/z 247.2 ([M+Na]$^+$). $^1$H-NMR (DMSO-d6, ppm): 1.21-1.26 (m, 6 H), 1.33-1.45 (m, 4 H), 1.54 (m, 2 H), 1.93 (m, 2 H), 3.40-3.47 (m, 4 H), 4.20 (t, 2 H, J=5.5 Hz).

EXAMPLE 26

Synthesis of Compound NM-009b

In a 25 mL round-bottomed flask were added a white solid of compounds NM-009a (1.12 g, 5 mmol) and 5 mL of acetic anhydride with stirring. Then 2-3 drops (catalytic amount) perchloric acid was added into the suspension. The reaction was run at room temperature for 3 hours. The reaction solution was poured into 20 g of ice water, and extracted with ethyl acetate (20 mL×3). The organic layers were combined, and washed with 30 mL of 1 N sodium bicarbonate solution and 30 mL of water, and dried with anhydrous sodium sulfate. The solvent was evaporated under reduced pressure to give a crude product as a colorless oil, which was separated by silica column chromatography (petroleum ether: ethyl acetate=10:1) to obtain NM-009b as a colorless oil (1.43 g, 92.9%). ESI-MS: m/z 309.3 ([M+H$_2$O]$^+$). $^1$H-NMR (DMSO-d6, ppm): 1.25 (s, 2 H), 1.35-1.47 (m, 12 H), 1.55 (s, 2 H), 1.98 (s, 8 H), 4.04 (t, 4 H).

EXAMPLE 27

Synthesis of Compound NM-009c

Compound NM-009b (616 mg, 2 mmol) was placed in a 25 mL round-bottom flask, and cooled with an ice bath. Then 0.4 mL of concentrated nitric acid was added with stirring, and 2.5 mL of concentrated sulfuric acid was slowly added dropwise to the mixture. The reaction was run with an ice bath for 1 hour. Then 2 mL of acetonitrile (4.8 mmol) was slowly added dropwise, and cooled with an ice bath for 1 hour. The reaction mixture was poured into 20 mL of ice water, and the aqueous layers were extracted with ethyl acetate (20 mL×4). The organic layers were combined, and washed with 30 mL of 1 N sodium bicarbonate solution and 30 mL of water, and dried with anhydrous sodium sulfate. The solvent was evaporated under reduced pressure to give a crude product as colorless oil, which was was separated by silica column chromatography (petroleum ether: ethyl acetate=1:3) to obtain compound NM-009c as an oil (423 mg, 57.9%). ESI-MS: m/z 366.3 ([M+H]$^+$). $^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 28

Synthesis of Compound NM-009d

To a 100 mL round-bottom flask were added in order the compound NM-009c (1 g, 2.7 mmol), 1.5 g of solid sodium hydroxide and 30 mL of diethylene glycol. The reaction was run for 15 hours under 170° C. The mixture was cooled to room temperature. Then 20 mL of water and ethyl acetate (20 mL×3) were added in order to extract to remove impurities. Water was distilled off under reduced pressure. To the remaining solution were added 30 mL of tetrahydrofuran, 1.18 g of Boc anhydride (5.4 mmol), 540 mg of triethylamine (5.4 mmol) and 10 mg of DMAP. The reaction was run under room temperature for 5 hours, and monitored with TLC. After the reaction being completed, 20 mL of saturated ammonium chloride solution was added into the reaction solution, and the mixture was extracted with ethyl acetate (30 mL×4). The ethyl acetate layers were combined, and washed with 30 mL of water and saturated sodium chloride solution in order, and dried with anhydrous sulfate sodium sulfate. The solvent was evaporated under reduced pressure to give crude product as a pale yellow oil, which was separated by silica column chromatography (petroleum ether: ethyl acetate=2:1) to obtain compound NM-009d as an oil (700 mg, 75.4%). ESI-MS: m/z 340.4 ([M+H]$^+$).

$^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 29

Synthesis of Compound NM-009e vb

Compound NM-009d (680 mg, 2 mmol) was dissolved in 10 mL of anhydrous dichloromethane with an ice water. Then a 2 mL mixture of acetic anhydride and fuming nitric acid in a ratio of 3:2 by volume was added. The ice bath was maintained and the reaction was run for 10-15 minutes. The reacted solution was poured into 10 mL of 1 N sodium bicarbonate solution. The dichloromethane was separated, and the aqueous layer was extracted with dichloromethane (10 mL×3). Organic layers were combined, washed with 10 mL of water, and dried with anhydrous sodium sulfate. The resulting materials were filtered, and the filtrate was to distilled under reduced pressure to obtain a crude product as a colorless oil, which was separated by silica column chromatography (petroleum ether: dichloromethane=10:1) to give a product NM-009e as a colorless oil (620 mg, 72.3%). ESI-MS: m/z 452.1 [M+Na]$^+$. $^1$H NMR (300 MHz, DMSO-d$_6$) δ1.17-1.29 (q, J=12 Hz, 2H), 1.36 (s, 13H), 1.49-1.53 (t, J=6 Hz, 4H), 1.52-1.66 (dd, J=33 Hz, 12 Hz, 4H), 1.68 (m, 2H), 2.09 (m, 1H, CH), 4.53-4.58 (t, J=7.5 Hz, 4H, 2×CH$_2$O), 6.46 (s, 1H, NH).

EXAMPLE 30

Synthesis of Compound NM-009

To the compound NM-008g (401 mg, 1 mmol) was added 5 mL of ether solution saturated with hydrogen chloride. The reaction was run at room temperature and monitored with TCL. When the reaction was completed, a white solid was precipitated. After filtration, the white solid was washed by anhydrous ether to give a pure product which was dried to give NM-008 (380 mg, 65.5%). ESI-MS: m/z 255.1 ([M+H]$^+$). $^1$H-NMR (DMSO-d6, ppm): 1.38-1.54 (m, 6 H), 1.60-1.77 (m, 6 H), 2.27 (m; 1 H), 4.32 (s, 4 H), 8.27 (s, 3 H).

EXAMPLE 31

Synthesis of Compound NM-011a

Compound 1,3-dibromo-adamantane (3 g, 10 mmol) was dissolved in 30 mL of toluene, and then 250 mg of AIBN (1.5 mmol), 7 g of tri-n-butyl tin (24 mmol), 3 g of ethyl acrylate (30 mmol) were added in order. The reaction was refluxed with at 110° C. under nitrogen for 3 hours. The reaction solution was cooled to room temperature and was poured into 30 mL of 0.2M aqueous ammonia. After being stirred fully, the organic layer was separated. The aqueous layers were extracted with ethyl acetate (20 mL×4). The organic layers were combined and washed with 30 mL of water and 30 mL of saturated sodium chloride solution. The resulting materials were dried with anhydrous sodium sulfate, and solvent was evaporated under the reduced pressure to give a crude product as a colorless oil, which was separated by silica column chromatography (petroleum ether: ethyl acetate=10:1) to give compound NM-011a as a colorless oil (2 g, 46.6%). ESI-MS: m/z 337.4 ([M+H]$^+$). $^1$H-NMR (DMSO-d6, ppm): 1.11 (s, 2 H), 1.15-1.19 (m, 6 H), 1.28-1.39 (m, 12 H), 1.53 (s, 2 H), 1.97 (s, 2 H), 2.19-2.24 (m, 2 H), 4.03 (q, 4 H, J=7.1 Hz).

EXAMPLE 32

Synthesis of Compound NM-011b

Compound NM-Olla (2.2 g, 6 mmol) was placed in a 50 mL round-bottom flask and cooled with an ice bath. Then 1.2 mL of concentrated nitric acid was added with stirring. To the mixture was slowly added dropwise 8.5 mL of concentrated sulfuric acid. The reaction was run for 1 hour cooled with an ice bath. To the reaction solution was slowly added 5.6 mL of acetonitrile (13.4 mmol). The reaction was continued with an ice bath for 1 hour. The reaction solution was poured to 20 mL of ice water, and the aqueous layer was extracted with ethyl acetate (20 mL×4). The organic layers were combined, and washed with 30 mL of 1 N sodium bicarbonate solution and 30 mL of water, and dried with anhydrous sodium sulfate. The solvent was evaporated under the reduced pressure to give a crude product as a colorless oil, which was separated by silica column chromatography (petroleum ether: ethyl acetate=1:3) to obtain compound NM-011b as an oil (2 g, 57.9%). ESI-MS: m/z 394.2 ([M+H]$^+$). $^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 33

Synthesis of Compound NM-011c

Compound NM-011b (1 g, 2.5 mmol) was dissolved in 20 mL of dehydrate tetrahydrofuran, and 450 mg of sodium borohydride was added. Then, 1.33 g of aluminum chloride was dissolved in 10 mL of tetrahydrofuran, and the solution was slowly added dropwise into the reaction mixture. Then the reaction was stirred at room temperature overnight. The reaction solution was poured into 50 mL of ice-water, stirred fully, and extracted with ethyl acetate (30 mL×4). The organic layers were combined, washed with 30 mL of saturated sodium chloride, and dried with anhydrous sodium sulfate. The solvent was evaporated to dryness under reduced pressure to give a crude product as a colorless oil, which was separated by silica column chromatography (ethyl acetate: methanol=10:1) to obtain NM-011c as a colorless oil (470 mg, 60.8%). ESI-MS: m/z 310.1 ([M+H]$^+$). $^1$H-NMR (DMSO-d6, ppm): 1.05-1.09 (m, 6 H), 1.22-1.39 (m, 8 H), 1.51-1.60 (m, 4 H), 1.73 (s, 3 H), 1.76 (s, 2 H), 2.07 (m, 1 H), 3.30-3.36 (m, 4 H), 4.39 (t, 2 H, J=5.2 Hz), 7.36 (s, 1 H).

EXAMPLE 34

Synthesis of Compound NM-011d

In 50 mL round-bottom flask were added in order a compound NM-011c (440 mg, 1.4 mmol), 750 mg of solid sodium hydroxide, and 10 mL of diethylene glycol. The reaction was run at 170° C. for 15 hours. The mixture was cooled to room temperature, and 20 mL of water was added. After being extracted with ethyl acetate (20 mL×3) to remove impurities, the water was removed by rotavap under reduced pressure. To the remaining solution were added 30 mL of tetrahydrofuran 560 mg of Boc anhydride (2.8 mmol), 280 mg of triethylamine (2.8 mmol), and 10 mg of DMAP. The reaction was run at room temperature for 5 hours, and monitored with TLC. After the reaction being completed, 20 mL of saturated ammonium chloride solution was added to the reaction solution, extracted with ethyl acetate (30 mL×4). The organic layers were combined, washed with 30 mL of water and saturated sodium chloride solution, and dried with anhydrous sulfate sodium sulfate. The solvent was evaporated under reduced pressure to give crude product as a pale yellow oil, which was separated by silica column chromatography (petroleum ether: ethyl acetate=2:1) to obtain compound NM-011d as an oil (320 mg, 55.9%). ESI-MS: m/z 340.4 ([M+H]$^+$). $^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 35

Synthesis of Compound NM-011e

Compound NM-011d (680 mg, 2 mmol) was dissolved in 10 mL of anhydrate dichloromethane, and cooled with an ice bath. Then, 2 mL a solution of acetic anhydride and fuming nitric acid in a ratio of 3:2 by volume was added. With the ice bath, the reaction was run for 10-15 minutes. The reaction solution was poured into 10 mL of 1 N sodium bicarbonate solution. After the organic layer being separated, the aqueous layer was extracted with dichloromethane (10 mL×3). The organic layers were combined, and washed with 10 mL of water and dried with anhydrous over sodium sulfate. After being filtrated, the solvent was distilled under reduced pressure to give a crude product as a colorless oil, which was separated by silica column chromatography (petroleum ether: dichloromethane=10:1) to obtain NM-011e as a colorless oil (620 mg, 72.3%). ESI-MS: m/z 452.1 ([M+Na]$^+$). $^1$H-NMR (DMSO-d6, ppm): 1.37 (s, 9 H), 1.40 (m, 6 H), 1.60 (m, 2 H), 1.72-1.82 (m, 4 H), 2.17 (m, 1 H), 4.23 (s, 4 H), 6.66 (s, 1 H).

EXAMPLE 36

Synthesis of Compound NM-011

To compound NM-011e (401 mg, 1 mmol) was added 5 mL of saturated solution of hydrogen chloride in ether. The reaction was run at room temperature, and monitored with TLC. After the reaction being completed, a white solid was precipitated. After filtration, the white solid was washed with anhydrous ether to give pure NM-011, which was dried to give NM-011 (380 mg, 65.5%). ESI-MS: m/z 255.1 ([M+H]$^+$). $^1$H-NMR (DMSO-d6, ppm): 1.38-1.54 (m, 6 H), 1.60-1.77 (m, 6 H), 2.27 (m, 1 H), 4.32 (s, 4 H), 8.27 (s, 3 H).

EXAMPLE 37

Synthesis of Compound NM-012a

A compound of 1,3-dibromo-adamantane (3 g, 10 mmol) was dissolved in 30 mL of toluene, and then 250 mg of AIBN (1.5 mmol), 7 g of tri-n-butyl tin (24 mmol), 3 g of 2-ethyl methacrylate were added in order. The reaction was refluxed at 110° C. under nitrogen for 3 hours. The reaction solution was cooled to room temperature, and was poured into 30 mL of 0.2 M aqueous ammonia. After being stirred fully, the organic layer was separated, the aqueous layer was extracted with ethyl acetate (20 mL×4). The organic layers were combined, and washed with 30 mL of water and 30 mL of saturated sodium chloride solution, dried with anhydrous sodium sulfate. The solvent was evaporated under reduced pressure to give a crude product as a colorless oil, which was separated by silica column chromatography (petroleum ether: ethyl acetate=10:1) to obtain NM-012a as a colorless oil (1.6 g, 43.1%). ESI-MS: m/z 337.4 ([M+H]$^+$). $^1$H-NMR (DMSO-d6, ppm): 0.97 (s, 2 H), 1.02-1.08 (m, 8 H), 1.15-1.20 (m, 7 H), 1.22-1.40 (m, 7 H), 1.50 (s, 2 H), 1.57-1.65 (m, 2 H), 1.93 (s, 2 H), 2.39-2.47 (m, 2 H), 3.98-4.11 (m, 4 H).

EXAMPLE 38

Synthesis of Compound NM-012b

Compound NM-012a (2 g, 5.5 mmol) was dissolved in 50 mL round-bottom flask, and cooled with an ice bath. Then, 1.1 mL of concentrated nitric acid was added with stirring. To the reaction mixture was slowly added dropwise 7.7 mL of concentrated sulfuric acid. The reaction was run with an ice bath for 1 hour. Then 4.9 mL of acetonitrile (11.7 mmol) was slowly added dropwise and the reaction was continued with the ice bath for 1 hour. The reaction solution was poured into 20 mL into ice water. The aqueous layer was extracted with ethyl acetate (20 mL×4). The organic layers were combined, and washed with 30 mL of 1 N sodium bicarbonate solution and 30 mL of water, and dried with anhydrous sodium sulfate. The solvent was evaporated to dryness under reduced pressure to give a crude product as a colorless oil, which was separated by silica column chromatography (petroleum ether: ethyl acetate=1:3) to obtain compound NM-011b as an oil (1.6 g, 69.2%). ESI-MS: m/z 422.2 ([M+H]$^+$). $^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 39

Synthesis of Compound NM-012c

Compound NM-012b (2 g, 4.7 mmol) was dissolved in 30 mL of anhydrate tetrahydrofuran, and 900 mg of sodium borohydride was added. Then, 2.6 g of aluminum chloride was dissolved in 20 mL of tetrahydrofuran, which was slowly added dropwise into the reaction materials. Then the mixture was stirred at room temperature overnight. The reaction solution was poured into 50 mL of ice water, stirred fully, and extracted with ethyl acetate (30 mL×4). The extracts were combined, and washed with 30 mL of saturated sodium chloride, and dried with anhydrous sodium sulfate. The solvent was evaporated to dryness under reduced pressure to give a crude product as a colorless oil, which was separated by silica column chromatography (ethyl acetate: methanol=10:1) to obtain NM-012c as a colorless oil (880 mg, 55.6%). ESI-MS: m/z 338.1 ([M+H]$^+$). $^1$H-NMR (DMSO-d6, ppm): 1.05-1.09 (m, 6 H), 1.22-1.39 (m, 8 H), 1.51-1.60 (m, 4 H), 1.73 (s, 3 H), 1.76 (s, 2 H), 2.07 (m, 1 H), 3.30-3.36 (m, 4 H), 4.39 (t, 2 H, J=5.2 Hz), 7.36 (s, 1 H).

EXAMPLE 40

Synthesis of Compound NM-012d

In 50 mL round-bottom flask were added in order compound NM-012c (670 mg, 2 mmol), 1 g of solid sodium hydroxide and 10 mL of diethylene glycol. The reaction was run at 170° C. for 15 hours. The reaction was cooled to room temperature, and 20 mL of water was added. The resulting materials were extracted with ethyl acetate (20 mL×3), and evaporated to remove water under reduced pressure. Then, 30 mL of tetrahydrofuran, 900 mg of Boc anhydride (4 mmol), 400 mg of triethylamine (4 mmol) and 10 mg of DMAP were added to the remaining solution, and reacted for 5 hours and monitored with TLC. After the reaction being completed, 20 mL of saturated ammonium chloride solution was added to the reaction solution, and extracted with ethyl acetate (30 mL×4). The ethyl acetate layers were combined, and washed with 30 mL of water and saturated sodium chloride solution in order, and dried with anhydrous sulfate sodium sulfate. The solvent was evaporated under reduced pressure to give crude product as a pale yellow oil, which was separated by silica column chromatography (petroleum ether: ethyl acetate=2:1) to obtain compound NM-012d as an oil (500 mg, 63.3%). ESI-MS: m/z 340.4 ([M+H]$^+$). $^1$H-NMR (DMSO-d6, ppm): 1.22-1.43 (m, 6 H), 1.67 (s, 4 H), 1.74 (s, 3 H), 1.81 (s, 2 H), 2.02 (s, 6 H), 2.15 (m, 1 H), 3.70 (s, 4 H).

EXAMPLE 41

Synthesis of Compound NM-012e

Compound NM-012d (680 mg, 2 mmol) was dissolved in 10 mL of anhydrate dichloromethane, cooling with an ice bath, and 2 mL of solution of acetic anhydride and fuming nitric acid in a ratio of 3:2 by volume was added. The ice bath was maintained, and the reaction was run for 10-15 minutes. The reaction solution was poured into 10 mL of 1 N sodium bicarbonate solution. The organic phase was separated and the aqueous layer was extracted with dichloromethane (10 mL×3). The organic layers were combined and washed with 10 mL of water, and dried with anhydrous sodium sulfate. After filtration, the solvent was distilled under reduced pressure to obtain a crude product as a colorless oil, which was separated by silica column chromatography (petroleum ether: dichloromethane=10:1) to give NM-012e as a colorless oil (620 mg, 72.3%). ESI-MS: m/z 508.1 [M+Na]$^+$. $^1$H NMR (300 MHz, DMSO-d$_6$) δ0.93-0.96 (d, J=9 Hz, 2×CH$_3$), 0.95-1.01 (dd, J=15 Hz, 6 Hz, 2H), 1.13 (m, 2H), 1.18-1.20 (d, J=6 Hz, 1H), 1.22-1.24 (d, J=6 Hz, 1H), 1.30 (s, 4H), 1.36 (s, 9H, C(CH$_3$)$_3$), 1.48-1.56 (m, 4H), 1.70 (m, 2H), 1.93-1.99 (m, 2H), 2.07 (m, 1H), 4.21-4.36 (m, 4H, 2×CH$_2$O), 6.41 (s, 1H, NH).

EXAMPLE 42

Synthesis of Compound NM-012

A 5 mL solution of saturated hydrogen chloride in ether was added into compound NM-011e (401 mg, 1 mmol). The reaction was run at room temperature, and monitored with TLC. A white solid was precipitated after the reaction being completed. After filtration, the white solid was washed with anhydrous ether to give a pure NM-011, which was dried to give NM-011 (380 mg, 65.5%). ESI-MS: m/z 255.1 ([M+H]$^+$). $^1$H-NMR (DMSO-d6, ppm): 1.38-1.54 (m, 6 H), 1.60-1.77 (m, 6 H), 2.27 (m, 1 H), 4.32 (s, 4 H), 8.27 (s, 3 H).

EXAMPLE 43

Protective Effects of Compounds on Primary Cerebellum Granule Cells of Rats

Isolated primary cerebellum granule cells of infant rats were inoculated in 96-well plates with 1.2×10$^5$/well by using 10% FBS+25 mM KCl+2 mM Glutamine+1% of double-antibody BME medium. After 24 hours, cytarabine with a final concentration of 10 iM was added to inhibit the proliferation of neurogliocyte cells. After the day 4, glucose with the final concentration of 5 mM was added every four days to complement energy metabolism and water evaporation of cells. The materials were placed in a cell incubator (37° C., 5% CO$_2$) to be cultured for 10 days. A 200 iM of glutamate was used to induce the excitotoxic injury of the primary cerebellum granule cells, with test groups of normal control group, glutamate group, pretreatment groups with different memantine nitrate compounds, and pretreatment control group with memantine. In the testing groups, the compounds of NM-001, NM-002, NM-003, NM-004, NM-005, NM-008, NM-009, NM-011, NM-012 and memantine were respectively added. After pre-protection for 2 h, 200 iM of glutamate was added to induce cell damage for 24 h, and then MTT was added to culture for 4 h. The supernatant fraction was sucked, and 150 iL of DMSO was added to each well for dissolving. After blending with shaking, the light absorption values under 570 nm wavelength was measured with a microplate reader, and the viability of cells was calculated. Cell viability (%)=absorbance of different groups/absorbance of the normal control group×100%.

TABLE 1

Protective effects of the compounds on rat's nerve cells

| Compounds | EC$_{50}$ (μM) |
|---|---|
| NM-001 | 24.62 |
| NM-002 | 25.2 |
| NM-003 | 15.36 |
| NM-004 | 8.12 |
| NM-005 | 6.06 |
| NM-008 | 4.37 |
| NM-009 | 5.20 |
| NM-011 | 5.86 |
| NM-012 | 9.30 |
| YQW-036 | 31.4 |
| memantine | 2.72 |

EXAMPLE 44

Protective Effect of the Compound NM-008 in a Rat Cerebral Ischemia MCAo Model

Female SD rats weighted 280-295 g were anesthetized with isoflurane, the proximal end of cephalic artery and the external carotid artery were ligatured separately, and a line embolism was inserted from the cephalic artery into the internal carotid. After insertion of the line embolism, the changes of the local cerebral blood flow were measured with a blood flow-meter. Before the preparation of the model and 5 min after the embolization, the flow change of the right ischemic area was measured by using a laser Doppler flow-meter, the criteria of success being that, after the embolism, blood flow is reduced to lower than 60 percent of the normal value.

Figure 8:
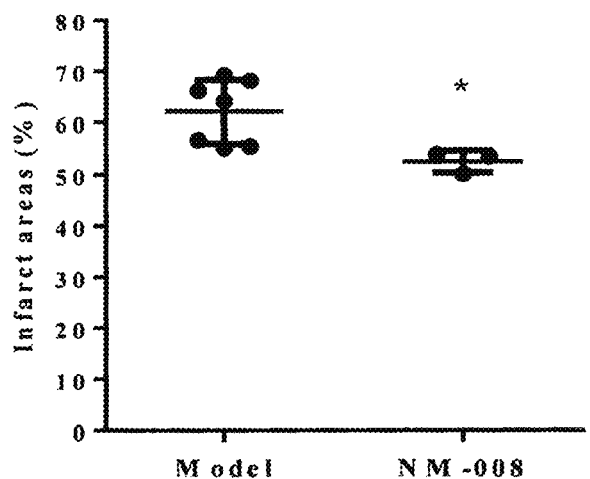
FIG. 8 illustrates the protective effect of the compound NM-008 to cerebral infarction of rats of a permanent cerebral ischemia model, while "*" indicates a significant difference compared with a control group.

At the time 3 h and 6 h after the model being prepared successfully, the rats was injected with the drug (60 mg/kg) intravenously once. Then, 24 h after the model being prepared, the animal was anesthetized with pentobarbital sodium, and was decapitated to give brain slices, which were stained with TTC to calculate the infarct area. It is shown that, as compared with the model group, NM-008 significantly reduced infarct area in the stoke model (P<0.05), and the protection ratio was 15.3% (FIG. 8).

In Examples 45 to 53 below, the animal model was molded and administered as follows unless otherwise specified:

Fifty six male BALB/c mice (18-22 g) were randomly divided into 7 groups. The mice were anesthetized with an isoflurane anesthesia machine. The mice were placed upside down on a wooden board, in the mice a longitudinal incision was made in the neck to expose the trachea. A venous indwelling needle with a 1 mL syringe attached to the end of the trachea was inserted into the trachea through the tracheal wall. The pre-absorbed 50 L LPS solution (1 mg/kg) with 0.8 mL of air (suitably in a speed of 0.4 mL/s or less) was instilled into the lungs of mice. After the tracheal instillation, the mice were erected, the mice were rotated vertically, the drug was evenly distributed in the lungs, and the wound was sutured to replicate and establish an endotoxin-type mouse ALI model. The tail vein was administered at a dose of 0.2 mL/mouse.

EXAMPLE 45

Effect of MN-08 on the Wet/Dry Weight Ratio of Lung Tissue

After 1 h and 6 h on the day of modeling, mice were given anesthesia with 4% chloral hydrate after 12 h of LPS administration. After taking blood from the eyelids, the supine position is fixed on the operating table. The skin is cut off from the perineum through the abdomen until the neck is fully exposed to the abdomen and chest. The large cross incision cuts the abdominal muscles and peritoneum to expose the abdominal cavity. Cut from the liver and the diaphragm to the chest, cut the diaphragm along the curvature of both sides of the chest, cut from the sides of the chest to the neck, remove the sternum and chest wall of the chest, fully expose the lungs, heart and neck trachea, and the left and right main bronchus, be careful not to damage the trachea and lungs. Take the lung tissue of the right upper lobe, weigh it, put it into the oven at 60° C. for 48 h, reach the constant weight, and calculate the ratio of wet weight/dry weight of the lung. The 1.5 mL centrifuge tube was placed in an oven at 60° C. in advance to a constant weight, which was recorded as W0. The lung tissue of the right upper lobe was taken, and the residual liquid was blotted with a clean filter paper, placed in a dried and weighed 1.5 mL centrifuge tube, and weighed as W1. Then, the tube was placed in an oven at 60° C. for 48 h to reach a constant weight, which was recorded as W2. The lung wet weight/dry weight ratio of the mouse was calculated, in a formula=(W1−W0)/(W2−W0).

Figure 9:
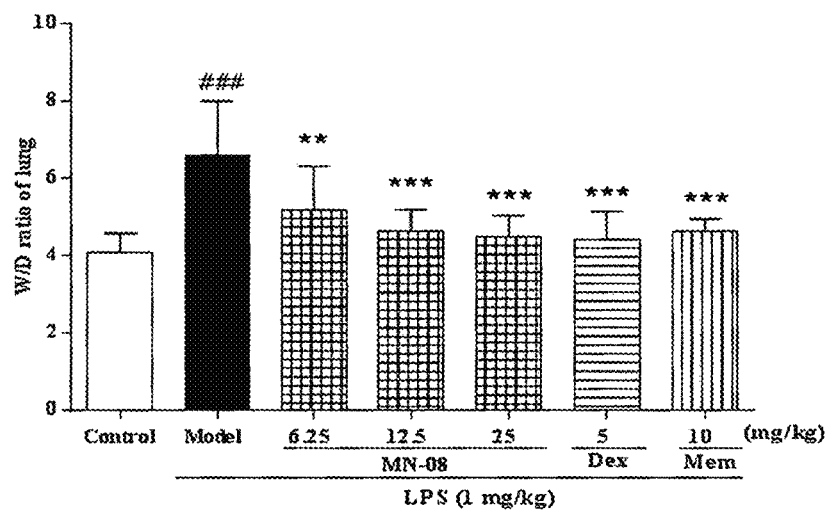
FIG. 9 illustrates the effect of compound MN-08 on the wet/dry weight ratio of lung tissue.

The results are shown in FIG. 9. MN-08 significantly reduced the increase in the wet weight to dry weight ratio of LPS-induced lung tissue in model mice. This indicates that MN-08 has improved lung tissue edema.

EXAMPLE 46

Effect of MN-08 on Total Protein in Bronchoalveolar Lavage Fluid Neutrophils and Bronchoalveolar Lavage Fluid After the mouse was molded and administered, the lung tissue was taken, and a trocar was inserted into the left lung tissue through the cervical trachea, and the trachea and trocar were tied with a wire through the tracheal esophageal space to fix and seal. The right main bronchus was clamped by a vascular clamp, and the trocar was inserted into a 0.3 mL PBS buffer to inject 0.3 mL of PBS buffer to reveal left lung swelling, and slowly withdrawn, three times, and the liquid was recovered. Centrifuge at 1500 rpm, 4° C. for 10 min. The supernatant was taken and stored at −80° C., and the protein and cytokines were measured for the lavage fluid. The cell pellet was used for cell counting. Resuspend the bronchoalveolar lavage fluid in pre-cooled PBS, pipet 20 mL of BALF sample into 0.38 mL white blood cell dilution, wait for the red blood cells to completely destroy, and absorb 10 mL of the mixed solution on the blood cell counting plate, and let stand for 2-3 min. Wait for the white blood cells to sink and count the cells.

The BALF supernatant protein concentration was quantified using BCA protein. Prepare BCA working solution with liquid A:B liquid=50:1. Take standard protein 20 mL for standard curve; add 2.5 mL sample and 7.5 mL water to each well of 96-well plate, add 80 mL working solution to each well, mix well on a shaker, and incubate in a 37° C. incubator for 30 min, and the OD value was detected at a wavelength of 570 nm of the multi-function microplate reader. The protein content can be calculated from the standard curve based on the sample OD value, divided by the total sample volume (10 mL), multiplied by the sample dilution factor (4 times), to have the actual sample concentration (mg/mL).

Figure 10A:
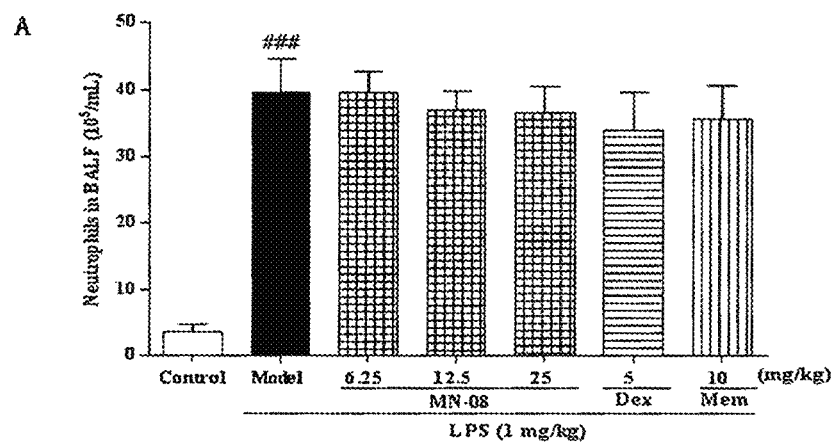
FIGS. 10A and 10B illustrate the effect of compound MN-08 on total protein in bronchoalveolar lavage fluid neutrophils and bronchoalveolar lavage fluid.
Figure 10B:
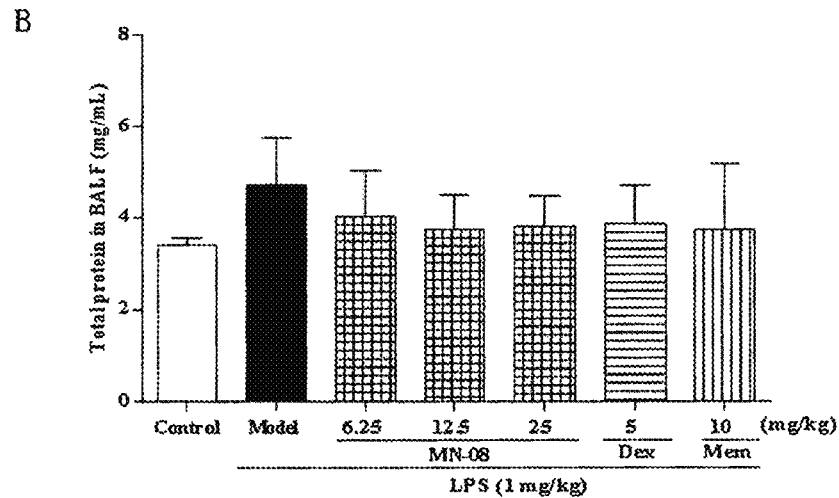

The results are shown in FIGS. 10A and 10B. The number of neutrophils in the bronchoalveolar lavage fluid of the model group induced by LPS (mean=39.67×105) was significantly higher than that of the normal control group (mean=3.5×105). After MN-08 treatment, the number of neutrophils in bronchoalveolar lavage fluid of mice decreased. MN-08 treatment reduced the increase in protein content of bronchoalveolar lavage fluid in the LPS-induced model mice.

EXAMPLE 47

Effect of MN-08 on Lung Tissue Permeability Index

At the end of mouse modeling and administration, the lung permeability index (LPI) was expressed as the ratio of protein content of BALF supernatant to plasma protein content, and protein content was determined by BCA, ie, LPI=BALF protein content/plasma protein content. An increase in the value indicates an increase in pulmonary capillary permeability. The experimental procedure is shown in Example 2. The BCA protein was quantitatively determined for the concentration of BALF protein and plasma protein.

Figure 11:
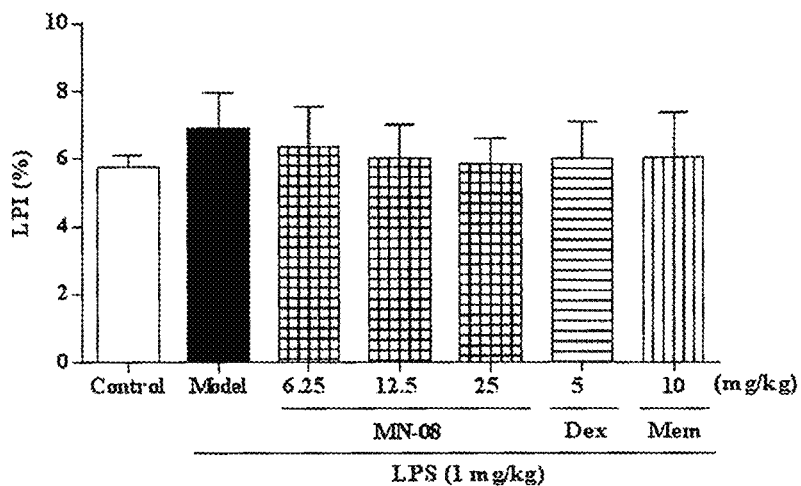
FIG. 11 illustrates the effect of compound MN-08 on lung tissue permeability index.

The results are shown in FIG. 11. MN-08 treatment reduced the increase in lung tissue permeability index (LPI) values in the LPS-induced model group.

EXAMPLE 48

Effect of MN-08 on Serum Inflammatory Factors in Mice

After the mouse was modeled and administered, the procedure was followed strictly according to the instructions of the mouse tumor necrosis factor TNF-α kit of Nanjing Jiancheng Biotechnology Co., Ltd. The blank control wells were not added with a sample, biotinylated anti-TNF-α antibody, and streptavidin HRP, but only the developer A&B was added and terminated, and the other steps were the same. Standard wells were added to the standard 50 mL, streptomycin HRP 50 mL. Add 40 mL of sample to the sample well, and then add 10 mL of anti-TNF-α antibody (or IL-1β) and 50 mL of streptavidin HRP, cover the membrane, gently shake and mix, and warm at 37° C. Foster for 60 minutes. The concentrated washing solution was diluted with distilled water to a 1× application solution, and was used. Carefully remove the sealing film, discard the liquid, dry it, fill each well with the washing solution, let stand for 30 seconds, then discard it, repeat 5 times, and pat dry. Add 50 ml of the developer A to each well, then add 50 ml of the developer B, gently shake and mix, and develop at 37° C. for 10 minutes in the dark. 50 mL of stop solution was added to each well to terminate the reaction. The blank holes were zeroed, and the absorbance (OD value) of each well was measured in sequence at 450 nm wavelength. The measurement should be carried out within 10 minutes after the addition of the stop solution. The regression equation of the standard curve is calculated according to the concentration of the standard product and the corresponding OD value, and the corresponding sample concentration is calculated on the regression equation according to the OD value of the sample.

Figure 12A:
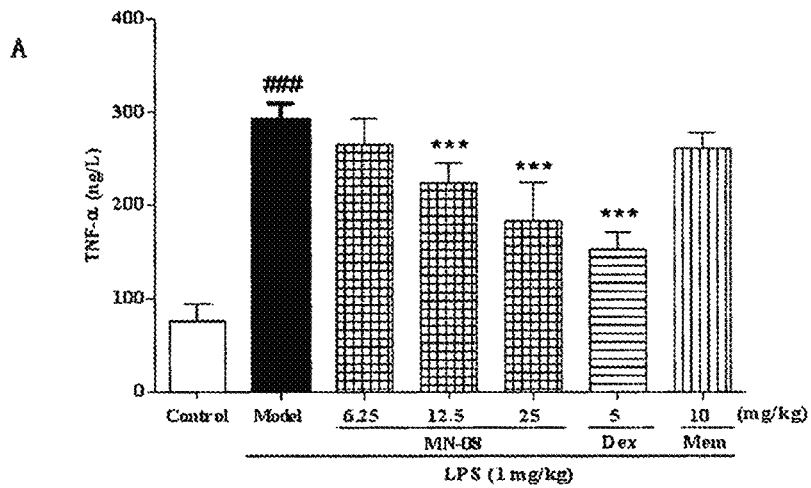
FIGS. 12A and 12B illustrate the effect of compound MN-08 on serum inflammatory factors in mice.
Figure 12B:
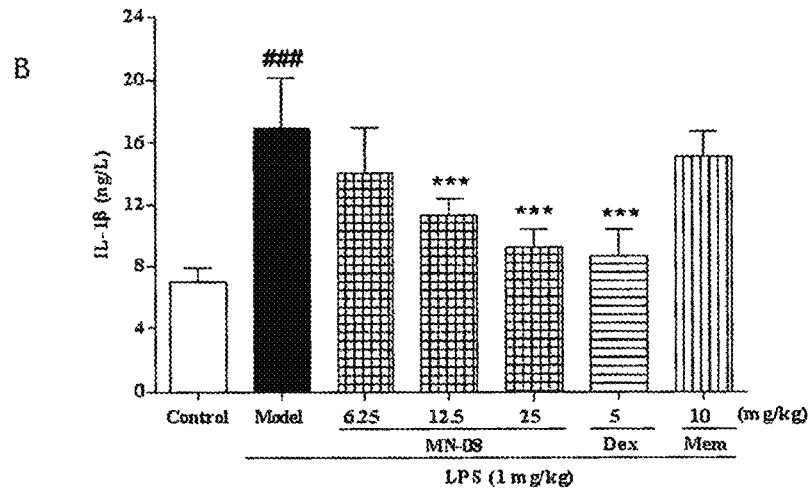

The results are shown in FIGS. 12A and 12B. MN-08 significantly reduced the levels of serum inflammatory factors TNF-α and IL-1 in LPS-induced model mice. It is indicated that MN-08 has the effect of inhibiting the secretion of serum inflammatory factors TNF-α and IL-1 in mice.

EXAMPLE 49

Effect of MN-08 on Myeloperoxidase Activity and Glutamate Content in Lung Tissue After the modeling and administration of the mouse, the myeloperoxidase activity was determined strictly according to the instructions of the assay kit of the Nanjing Perm Biotechnology Co., Ltd. myeloperoxidase (MPO). Myeloperoxidase (MPO) is present in neutrophils, and the amount of enzyme contained in each cell is constant, accounting for about 5% of the dry weight of the cells. This enzyme has the ability to reduce hydrogen peroxide. Features can analyze the activity of the enzyme and quantitatively determine the number of neutrophils. Enzyme activity unit is defined as: $H_2O_2$ is decomposed by 1 mmol into one enzyme activity unit per gram of tissue wet film in a reaction system of 37° C. MPO activity (U/g tissue wet weight)=(measured OD value−control OD value)/11.3×sample amount (g).

The detection of glutamic acid content was strictly carried out in accordance with the procedures of the glutamic acid determination kit of the Nanjing Jiancheng Biotechnology Co., Ltd. According to the instructions, the sample and each reagent were added and mixed. After 37 min in a water bath at 37° C., it is removed and placed at 340 nm, 1 cm light path, double distilled water was adjusted to zero, and the absorbance value $A_2$ of each tube was measured. The tissue homogenization is calculated as: GLU concentration (µmol/gprot)={(measure $A_2$ value−measure $A_1$ value)−(blank $A_2$ value−blank $A_1$ value)}/{(standard $A_2$ value−standard $A_1$ value)−(blank $A_2$ value−blank $A_1$ value)}×Standard concentration (200 µmol/L×sample pre-test dilution factor (4 times)/sample protein concentration (gprot/L).

Figure 13A:
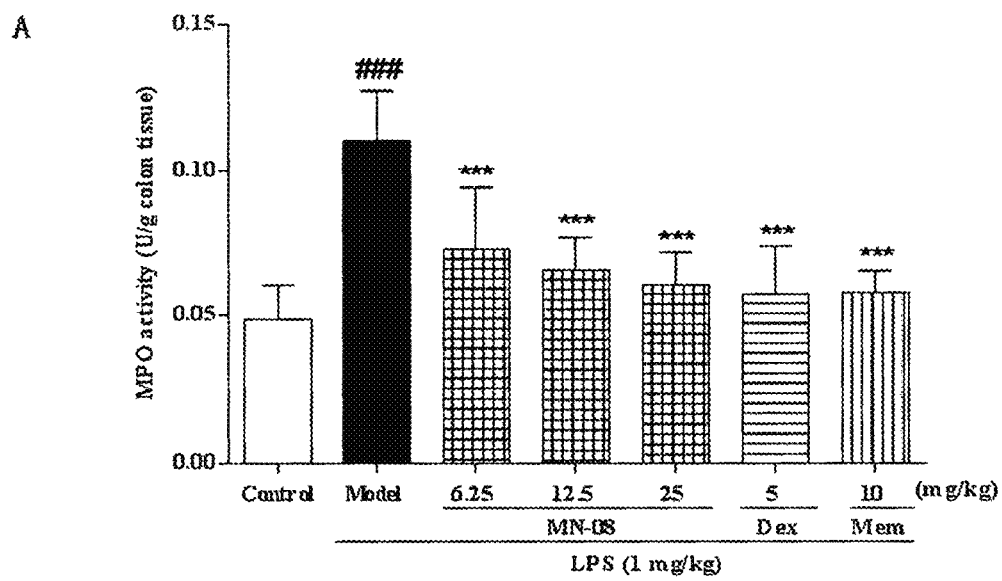
FIGS. 13A and 13B illustrate the effect of compound MN-08 on myeloperoxidase activity and glutamate content in lung tissue.
Figure 13B:
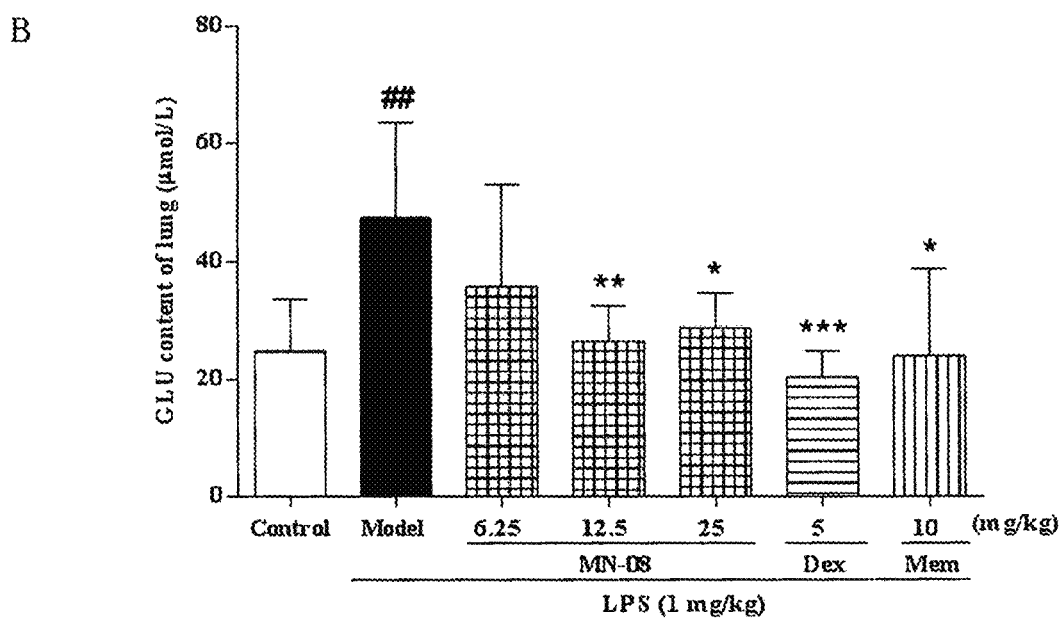

As a result, shown in FIGS. 13A and 13B, MN-08 has the effect of reducing the vitality of MPO, inhibiting the aggregation of neutrophils, reducing the secretion of inflammatory factors, and reducing the inflammatory response. MN-08 may inhibit the excessive production of glutamate by antagonizing the action of NMDA receptors, thereby reducing the damage to lung tissue.

EXAMPLE 50

Effect of MN-08 on the Contents of Superoxide Dismutase, Glutathione and Malondialdehyde in Lung Tissue After the mouse was molded and administered, the superoxide dismutase (SOD) was determined in accordance with the instructions of the Total Superoxide Dismutase (T-SOD) assay kit of Nanjing Jiancheng Biotechnology Co., Ltd. Superoxide anion radicals (O2-.) are produced by the xanthine and xanthine oxidase reaction system, the latter oxidizes hydroxylamine to form nitrite, which is purple-red under the action of a color developer, and its absorbance is measured by a visible spectrophotometer. When the measured sample contains SOD, it has a specific inhibitory effect on the superoxide anion radical, which reduces the formation of nitrite. The absorbance value of the tube in the colorimetric measurement is lower than the absorbance value of the control tube, and the formula is adopted. The calculation can determine the SOD activity in the sample to be tested. According to the instructions, mix the sample with each reagent and mix it. Leave it at room temperature for 10 minutes at a wavelength of 550 nm, 1 cm light-diameter color cup, double distilled water to zero, colorimetric. The total SOD activity was calculated according to the following formula: the amount of SOD corresponding to 50% of the SOD inhibition rate per milligram of tissue protein in 1 mL of the reaction solution was 1 SOD activity unit (U). Total SOD activity (U/mgprot)=(control OD value−measured OD value)/control OD value/50%×total reaction volume/sample volume (mL)/sample protein concentration to be tested (mgprot/mL).

The glutathione (GSH) was determined in accordance with the instructions of the glutathione (GSH) assay kit of Nanjing Jiancheng Biotechnology Co., Ltd. After the sample and the reagents were added according to the instructions, mix them, let stand for 5 min, 420 nm, 1 cm optical path, double distilled water to zero, and measure the absorbance of each tube. GSH content was calculated according to the following formula: GSH content (mgGSH/gprot)=(measured OD value−blank OD value)/(standard OD value−blank OD value)×standard concentration (20×10−3 mmol/L)×GSH molecular weight×Sample dilution before test/concentration of homogenized protein to be tested (gprot/L).

The malondialdehyde (MDA) was determined in accordance with the instructions of the Malondialdehyde (MDA) assay kit of the Yunnan Molded Biotechnology Co., Ltd. Malondialdehyde (MDA) in the lipid peroxide degradation product can be condensed with thiobarbituric acid (TBA)* to form a red product with a maximum absorption peak at 532 nm. The MDA content in the tissue was calculated in the following formula: MDA content (nmol/mgprot)=(measured OD value−blank OD value)/(standard OD value−blank OD value)×standard concentration (10 nmol/L)/sample protein concentration (mgprot/mL).

Figure 14A:
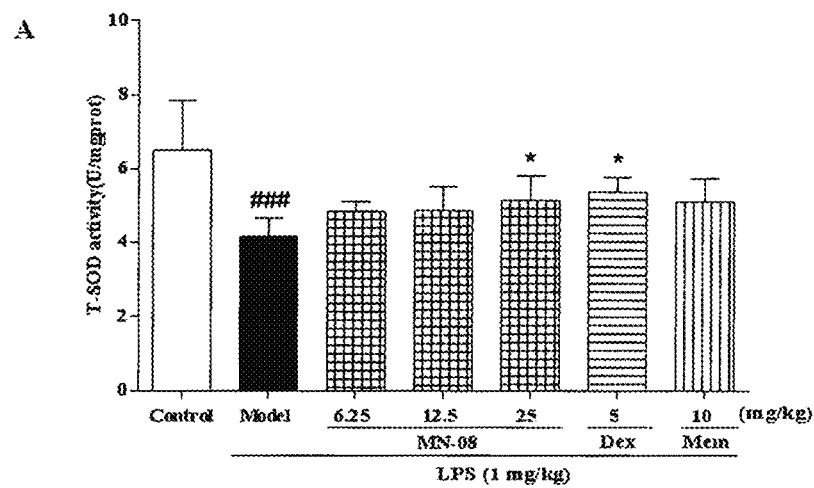
FIGS. 14A to 14C illustrate the effect of compound MN-08 on the levels of superoxide dismutase, glutathione, and malondialdehyde in lung tissue.
Figure 14B:
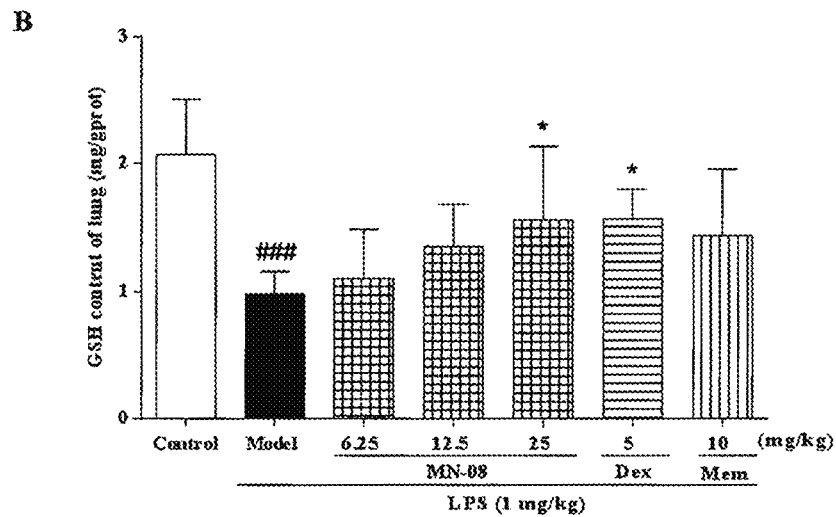
Figure 14C:
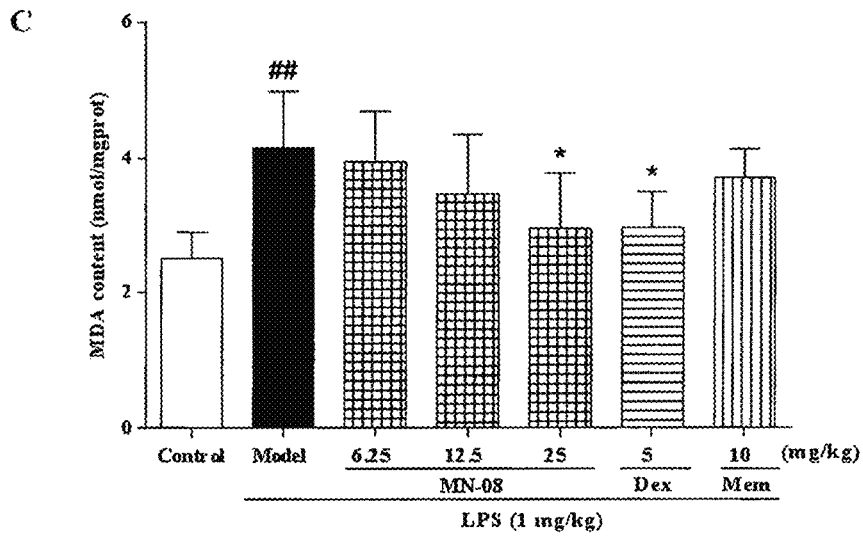

The results are shown in FIGS. 14A to 14C. MN-08 can significantly increase the SOD activity (mean=4.161) and GSH (mean=0.9836) in lung tissue of LPS-induced model mice, while MN-08 can significantly reduce LPS. The induced model group of mice with elevated MOD content in the lung tissue (mean=4.158) has the effect of protecting the lung tissue from oxidative attack.

EXAMPLE 51

Protective Effect of MN-08 on Lung Tissue

After modeling and administration of the mice, lung tissue of 1 cm×1 cm×1 cm was taken in the right lower lobe of the right lung, and washed with pre-cooled PBS and fixed with 4% paraformaldehyde solution. Dehydrated and paraffin embedded, sliced and stained with hematoxylin-eosin (H&E). The process is as follows: (1) Dewaxing: 1) The paraffin sections are placed in a 65° C. oven to melt the wax until the paraffin is completely melted and cooled at room temperature. 2) The slices were dewaxed in two bottles of xylene in turn, 10 minutes each time, and washed twice. 3) After thorough dewaxing, the sections were sequentially hydrated in gradient ethanol (100%, 100%, 90%, 90%, 80%, 80%, 70%), and for each concentration hydration was carried out for 5 minutes. (2) Dyeing: A. Transfer to hematoxylin and dip for 10 min. B. Placed into water, wash off the hematoxylin and the floating color for about 1 min. C. Placed into the differentiation solution (1% hydrochloric acid ethanol) for about 30 seconds, and the slices are faded to pale blue. D. Placed into running water and wash for 10-30 seconds to make the tissue fresh blue or sky blue. E. Placed into the eosin solution and dip for 2 min. If the dyeing is slow, add glacial acetic acid (100 mL of eosin solution plus 1-2 drops of glacial acetic acid) to help the dye. F. Placed into the water, wash off the eosin float, and wipe off the excess dye on the slide with gauze. (3) Dehydration and transparency: hydrated by gradient ethanol (concentration from low to high), and xylene is transparent. (4) Neutral gum seal.

Figure 15:
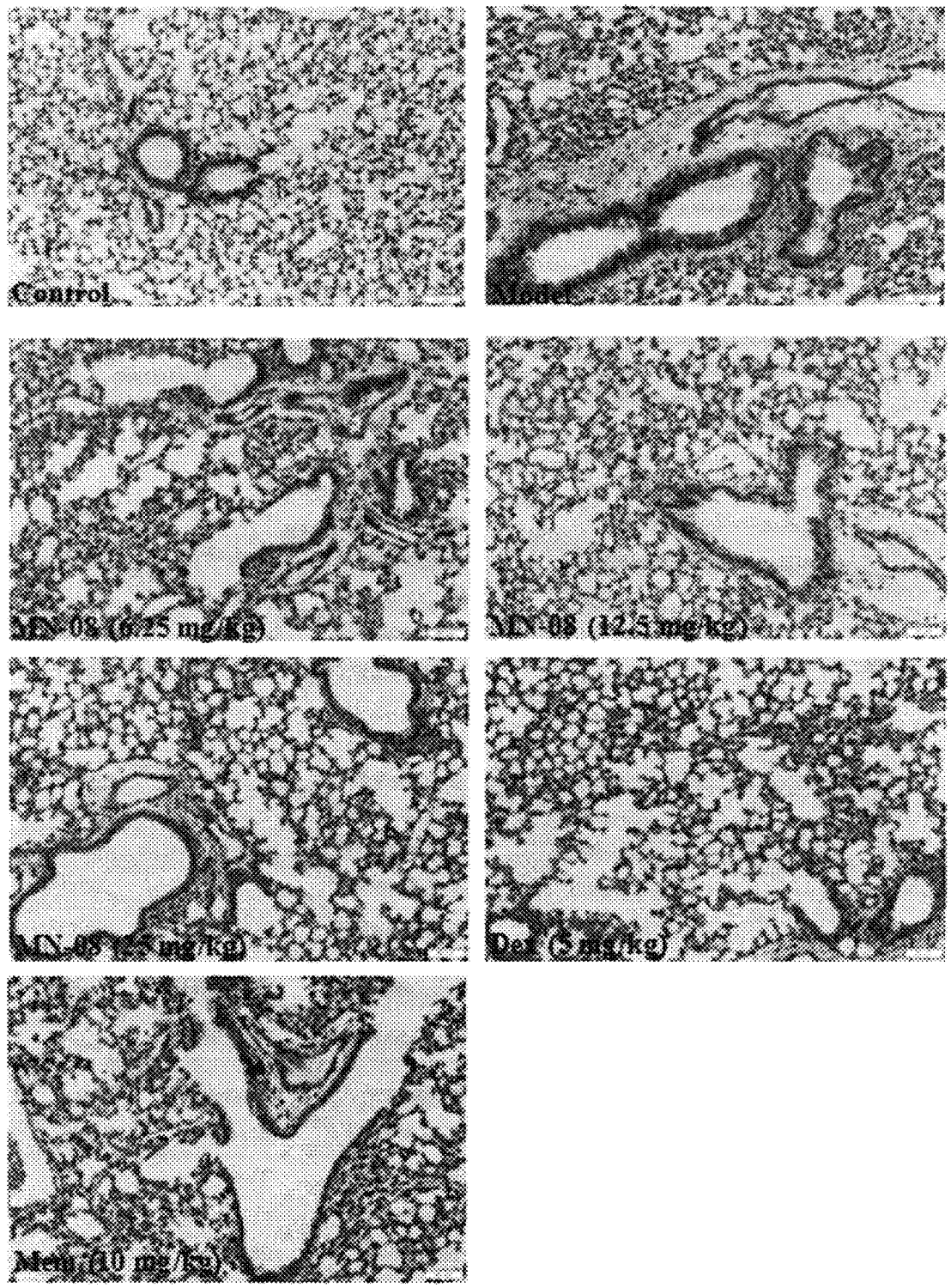
FIG. 15 illustrates the protective effect of compound MN-08 on lung tissue.

The results are shown in FIG. 15. MN-08 effective relieved and improved in various degree the conditions of LPS-induced lung tissue inflammatory cell infiltration, alveolar wall thickening, hemorrhage and edema.

EXAMPLE 52

Effect of MN-08 on Tight Junctional Structural Proteins in Lung Tissue

After modeling and administration of the mice, paraffin sections made from the right lower lobe were subjected to immune-histochemical staining for ZO-1, Claudin-1, and JAM-1. The process is as follows: (1) Dewaxing: 1) The paraffin sections are placed in a 65° C. oven to melt the wax until the paraffin is completely melted and cooled at room temperature; 2) the slices were dewaxed in two bottles of xylene in turn, 10 minutes each time, and washed twice; 3) after thorough dewaxing, the sections were sequentially hydrated in gradient ethanol (100%, 100%, 90%, 90%, 80%, 80%, 70%), and each concentration was hydrated for 5 minutes; 4) the sections were then immersed in citrate buffer for 50 minutes in a microwave method for 5 minutes, and the antigen was repaired by medium to low fire for 10 minutes; 5) after naturally cooling to room temperature, the sections were placed in a solution containing 3% H2O2 and incubated for 10 minutes in the dark; 6) the sections were washed 3 times in PBS solution for 5 minutes each time; 7) cover the tissue with horse serum (10%) supplemented with 0.3% Triton and incubate for 1 h; 8) aspirate serum, add ZO-1 (1:200), Claudin-1 (1:200), JAM-1 (1:200) primary antibody, and incubate overnight at 4° C.; 9) aspirate the primary antibody and gently slide the slices into the PBS solution for 3 times for 5 minutes each time; 10) add the horseradish peroxidase-labeled secondary antibody (provided in the DAB kit) to cover the tissue and incubate for 60 min at room temperature; 11) wash the tablets three times for 5 minutes each time, add the existing DAB coloring working solution to the tissue sections according to the kit procedure, and control the staining time under the microscope, the counterstaining was then performed with hematoxylin to enhance the background control; 12) hydrated by gradient ethanol (low to high concentration), transparent with xylene, and finally sealed with neutral gum.

Figure 16A:
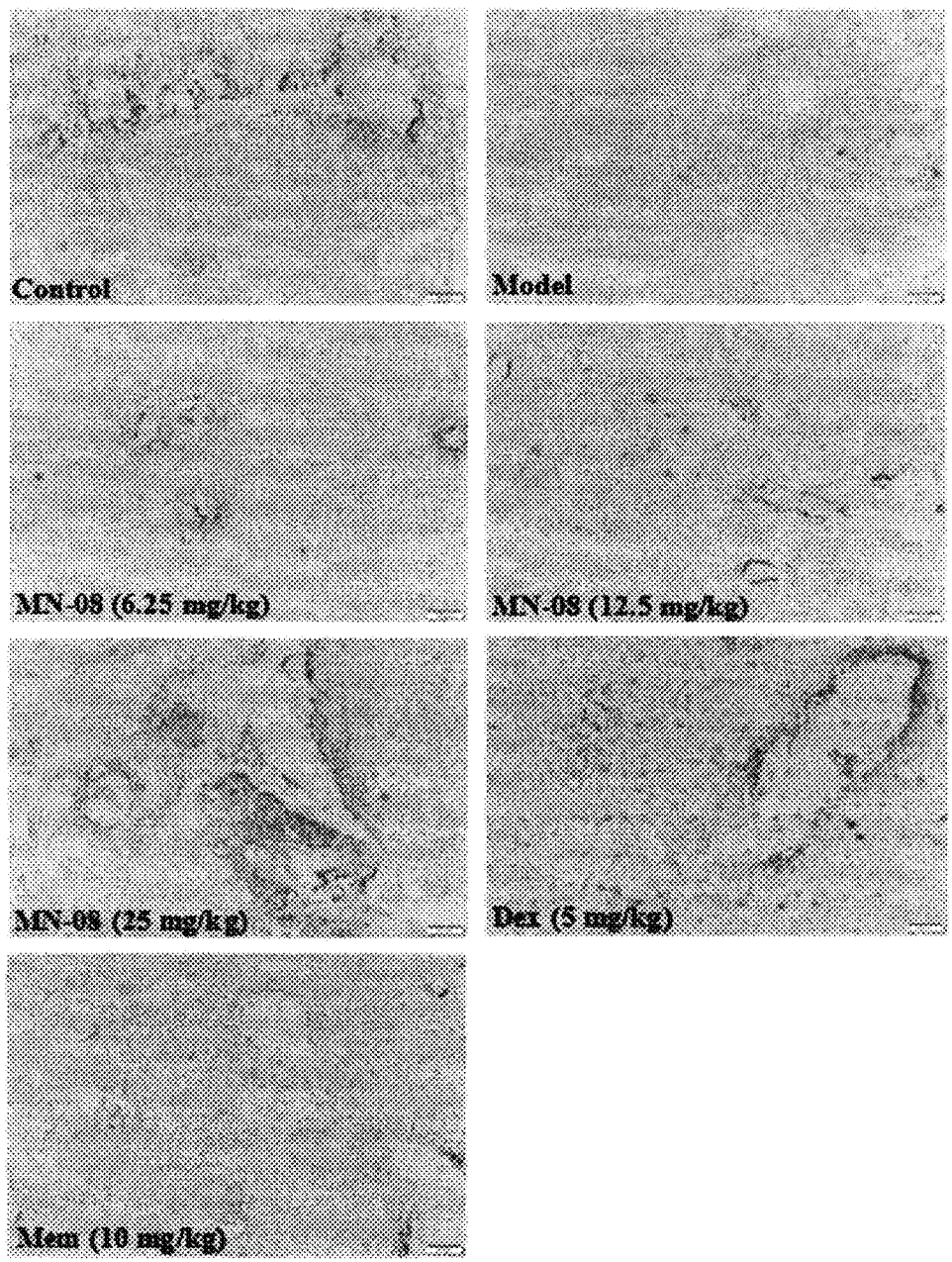
FIGS. 16A to 16C illustrate the effect of compound MN-08 on tight junctional structural proteins in lung tissue.
Figure 16:
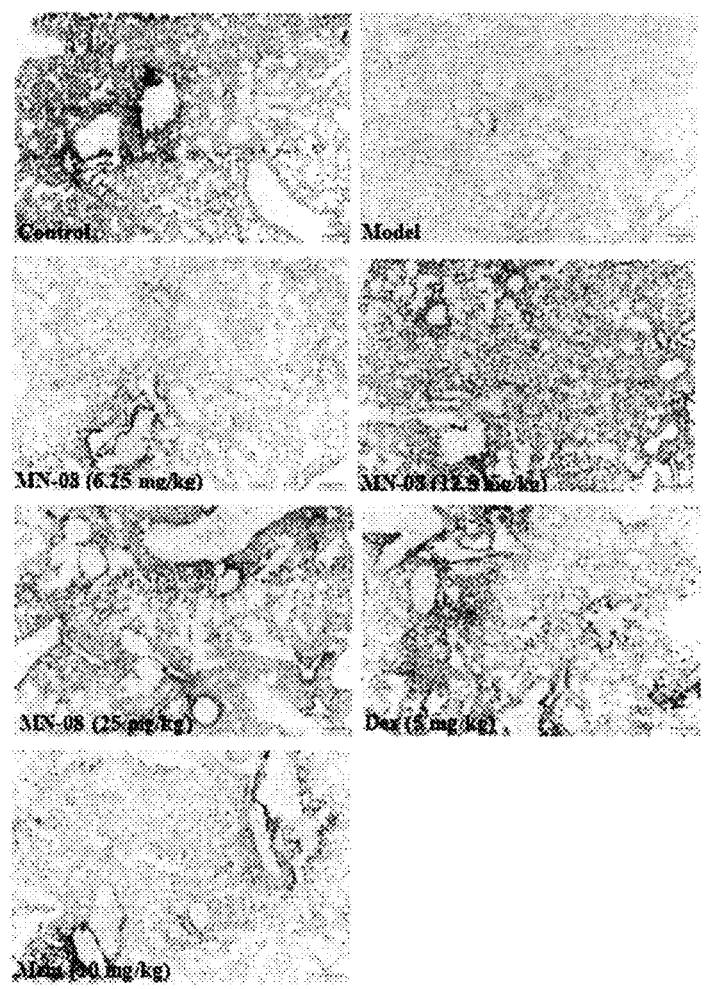
Figure 16:
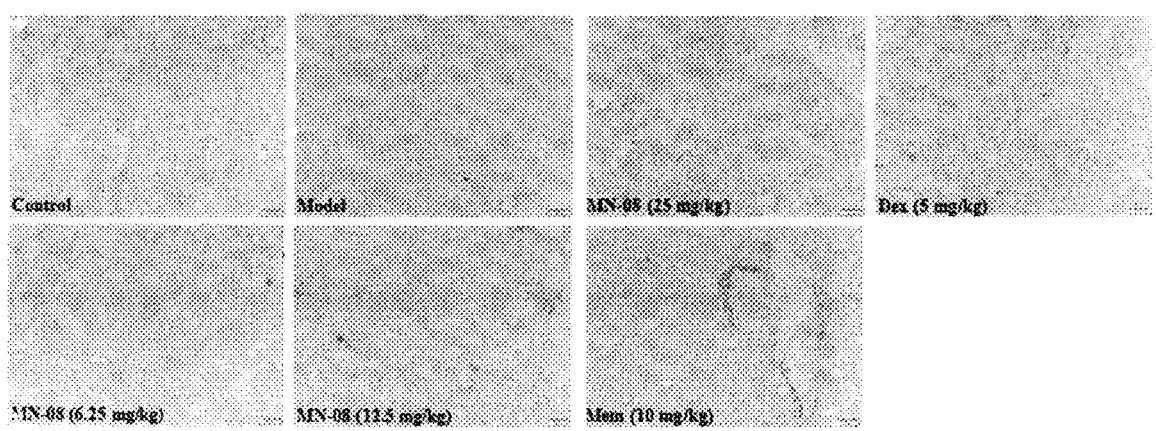

The results are shown in FIGS. 16A to 16C. MN-08 can significantly increase LPS-induced cytoplasmic adhesion protein ZO-1 in the tight junction of mouse lung tissue, and decrease the expression level of connective molecule JAM-1 and Cladin-1, and has the function of protecting the tight junction structure of lung tissue.

EXAMPLE 53

MN-08 Regulates NF-κB Signaling Pathway-Related Proteins and MAPK Signaling Pathway-Related Proteins in Lung Tissue After each model of 8 mice, after modeling and administration according to the above method, each mouse lung tissue of about 20 mg was weighed and transferred to a homogenate tube, and 200 μl of RIPA lysate (1% Protease Inhibitor Cocktail, 1% PMSF) was added, mechanically cracked on ice after homogenization. Centrifuge for 15 min at 12000 r/min and take the supernatant. Each group was given 40 μl of protein concentration, and the other was immediately dispensed and stored in a −80° C. refrigerator for 2 weeks. Western blotting was carried out according to the conventional experimental method, in which the primary antibody was diluted 1:1000 and the secondary antibody was diluted 1:2000.

Figure 17A:
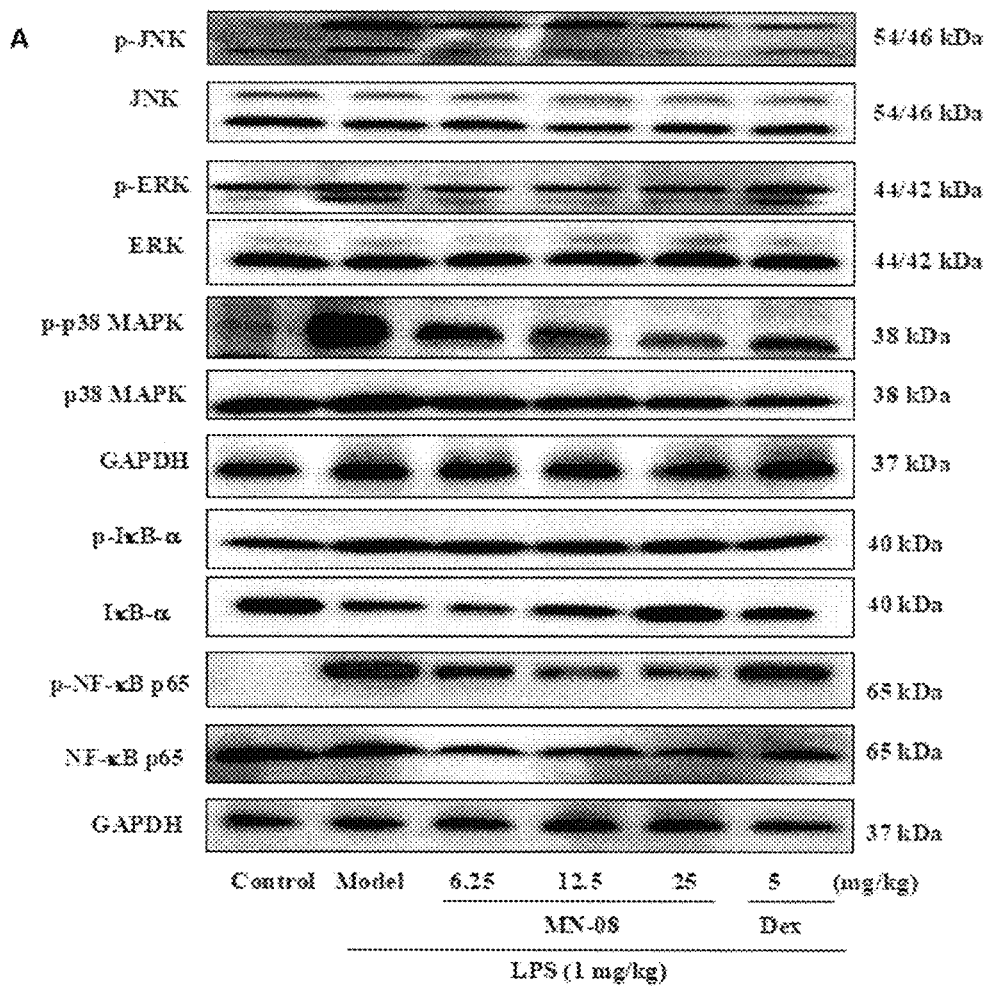
FIGS. 17A and 17B illustrate the regulation of MN-08 on NF-κB signaling pathway-related proteins and MAPK signaling pathway-related proteins in lung tissue.
Figure 17B:
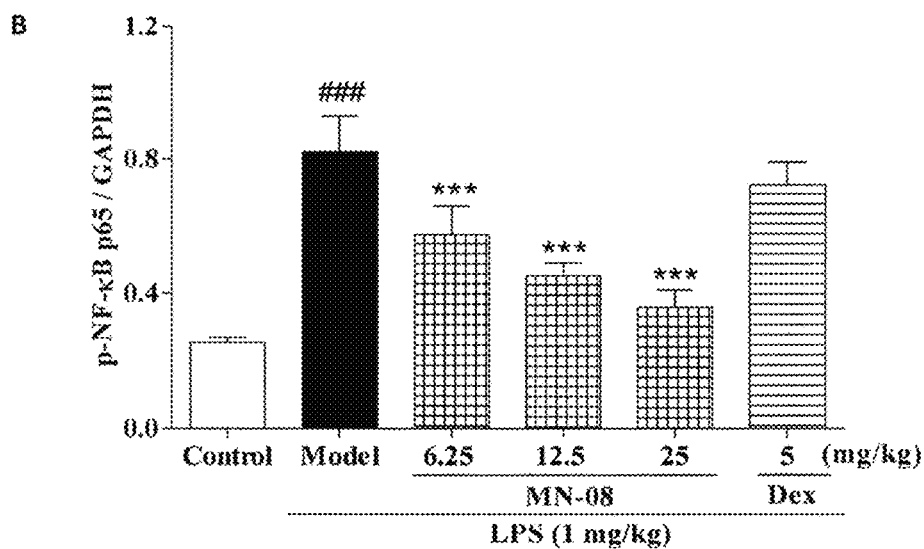
Figures 1, 18A:
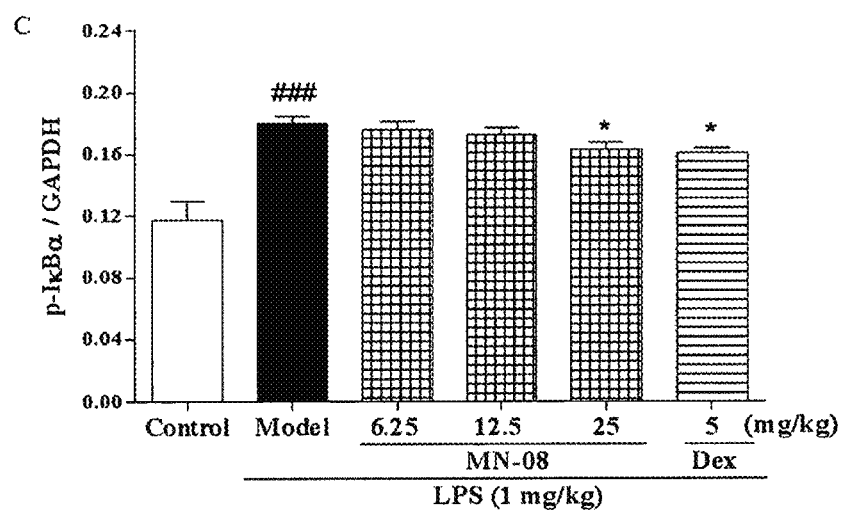
Figures 2, 18A:
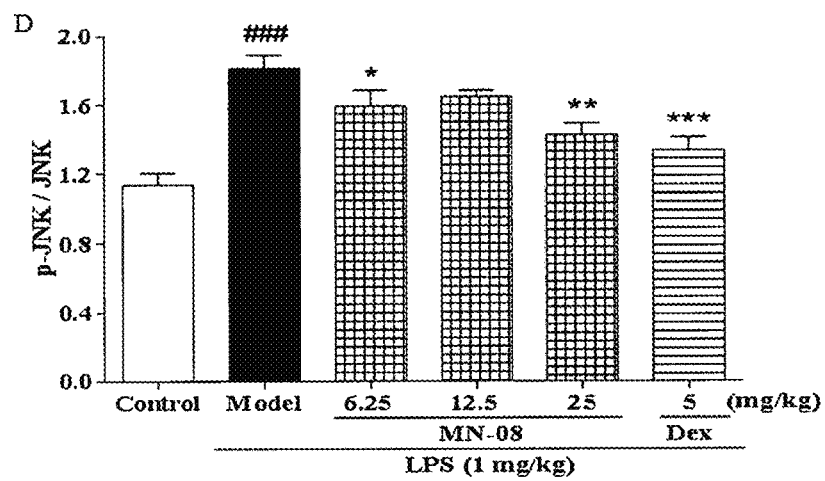
Figures 3, 18A:
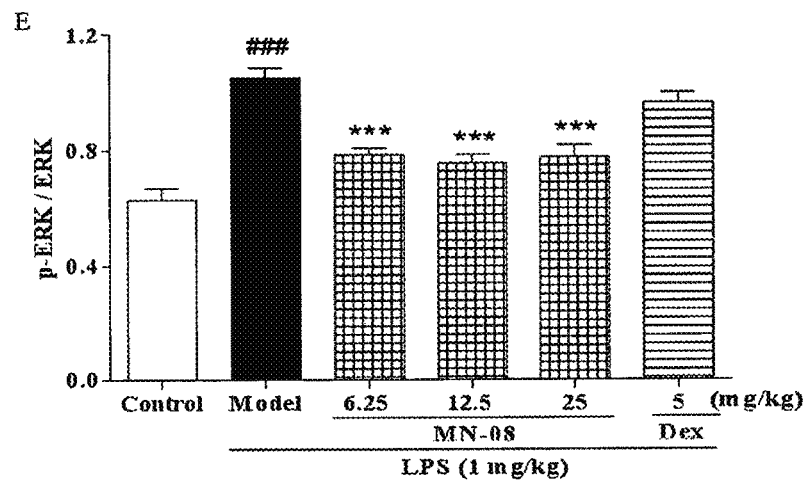
Figures 1, 18B:
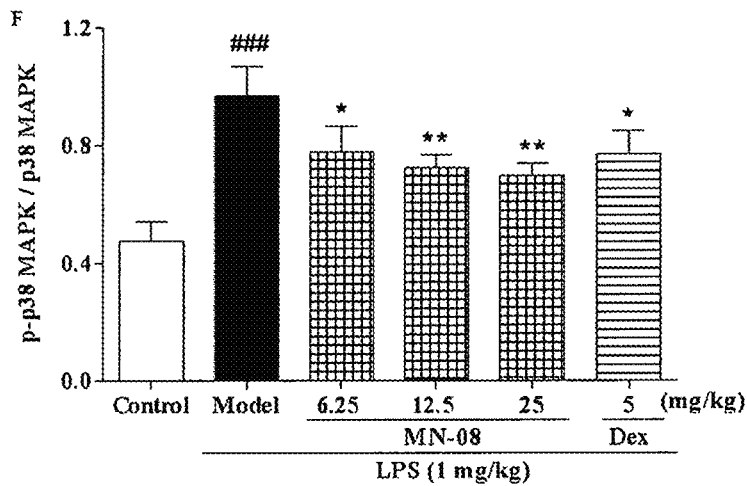
Figures 2, 18B:
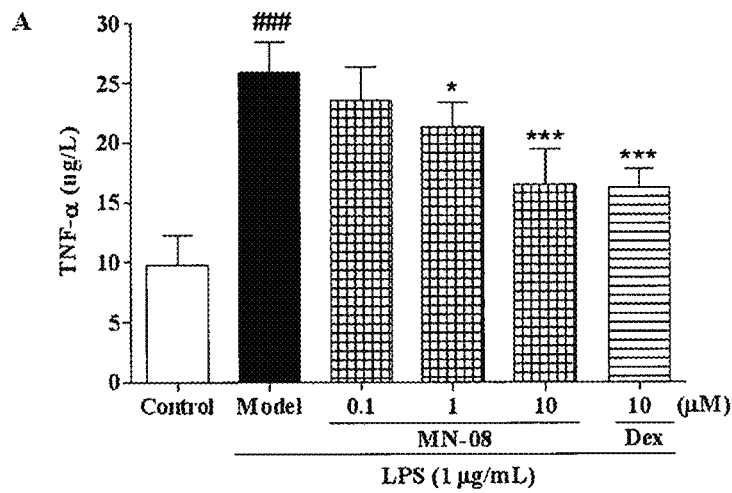
Figures 3, 18B:
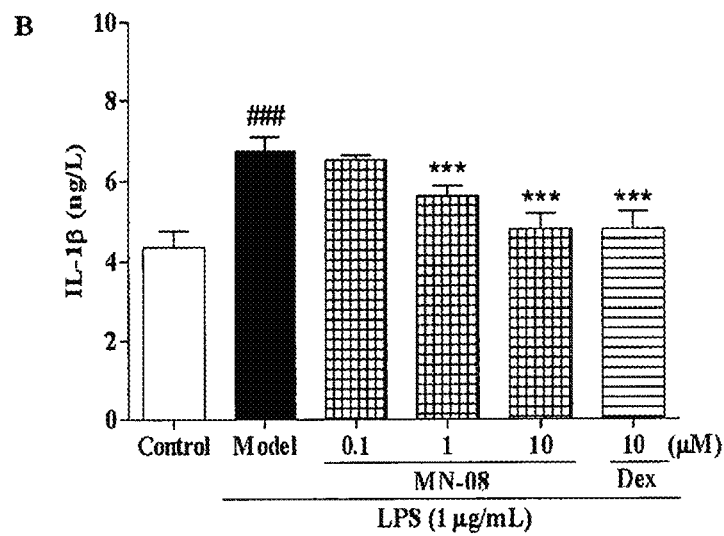

The results of Western Blot are shown in FIGS. 17A and 17B. The expression of pIκBα and p-NF-κB P65 in the lung tissue of the model group induced by LPS was significantly increased ($p<0.001$), while the treatment of MN-08 effectively inhibited the phosphorylation level of IκBα ($p<0.05$), effectively inhibited nuclear transfer of NF-κB P65 ($p<0.001$), and reduced pulmonary edema caused by acute inflammation. Treatment with MN-08 significantly reduced the expression of p-JNK, p-ERK ($p<0.001$) and p-p38 MAPK ($p<0.01$).

EXAMPLE 54

MN-08 Inhibits LPS-Induced Secretion of Proinflammatory Factors TNF-α and IL-1β in RAW 264.7 Cell Supernatants The ELISA kit uses a competition method to detect the levels of tumor necrosis factor-α (TNF-α) and interleukin-1β(IL-1β) in the sample. The sample was added to the enzyme-labeled wells pre-coated with the antibody, and then the horseradish peroxidase-labeled recognition antigen was added and incubated at 37° C. for 1 h. The two competed with the solid phase antigen to form an immune complex, which was washed with PBST. After that, the combined HRP catalyzes the blue color of TMB (tetramethylbenzidine), which is then converted to yellow by the action of acid, and has an absorption peak at 450 nm. The absorbance value is inversely related to the concentration of the antigen in the sample. Calculations were performed using ELISA-Calc.

As a result, shown in FIGS. 18 A-1 to 18A-3 and 18B-1 to 18B-3, MN-08 inhibited the secretion of proinflammatory factors TNF-α and IL-1β in the supernatant of RAW 264.7 cells induced by LPS.

EXAMPLE 55

MN-08 Regulates LPS-Induced NF-κB Signaling Pathway-Related Proteins and MAPK Signaling Pathway-Related Proteins in RAW 264.7 Cells RAW 264.7 cells were seeded in a 25 cm² flask for 24 h, and the original medium in the flask was aspirated. The cell protein is extracted using a kit. The protein was quantified by BCA method, and 5×loading buffer was added in a ratio of 1:4, and then boiled at 100° C. for 5 min, and then electrophoresed after cooling. Western blotting was carried out according to the conventional experimental method, in which the primary antibody was diluted 1:1000 and the secondary antibody was diluted 1:2000.

As shown in FIGS. 19A-1 to 19A-2, 19B-1 to 19B-3 and 19C, MN-08 inhibited LPS-induced nuclear transfer of NF-kB p65 in RAW 264.7 cells and down-regulated the phosphorylation levels of p38 MAPK, ERK and JNK proteins in the MAPK signaling pathway. MN-08 down-regulated the expression of inflammatory factors iNOS, COX-2 and TNF-α in LPS-induced RAW 264.7 cells. MN-08 up-regulated the expression of antioxidant protein in HO-1 and Nrf2 in LPS-induced RAW 264.7 cells.

EXAMPLE 56

Protective Effect of Amantadine Nitrate Compounds on Cerebellar Granule Cells

Primary isolated neonatal rat cerebellar granule cells were seeded at 1.2×105/well in 96-well plates and cultured in BME medium containing 10% FBS+25 mM KCl+2 mM Glutamine+1% double antibody. After 24 h, cytarabine was added at a final concentration of 10 μM to inhibit the proliferation of glial cells. From the 4th day, a final concentration of 5 mM glucose was added every 4 days to supplement the energy metabolism and evaporation of the cells, and cultured in a cell culture incubator (37° C., 5% $CO_2$) for 10 days. Excitotoxic damage of primary cerebellar granule cells was induced by 200 μM glutamate, which was divided into normal control group, glutamic acid group, different amantadine nitrate compound pretreatment group and memantine pretreatment control group. Different concentrations of compounds MN-04, MN-05, MN-06, MN-07, MN-08, MN-09 and memantine were pre-protected for 2 h according to the experimental group, and 200 μM glutamate was added. The cells were injured for 24 h, then added to MTT for 4 h. After the supernatant was aspirated, 150 μL of DMSO was added to each well to dissolve. After shaking and mixing, the absorbance was measured at 570 nm using a microplate reader to calculate the cell viability. Cell viability (%)=absorbance of different treatment groups/absorbance of normal control group×100%.

Figures 1, 19B:
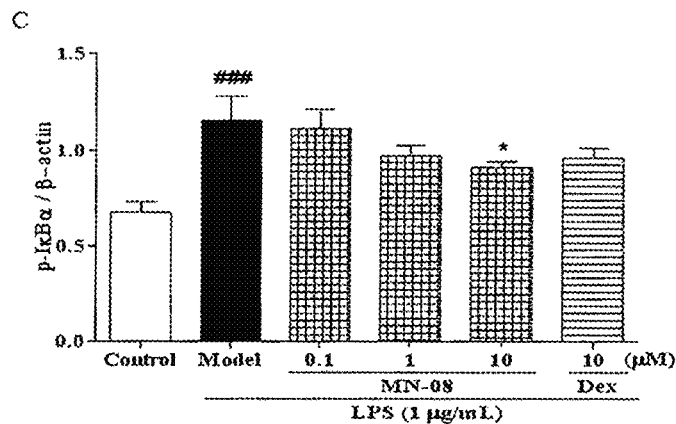
Figures 2, 19B:
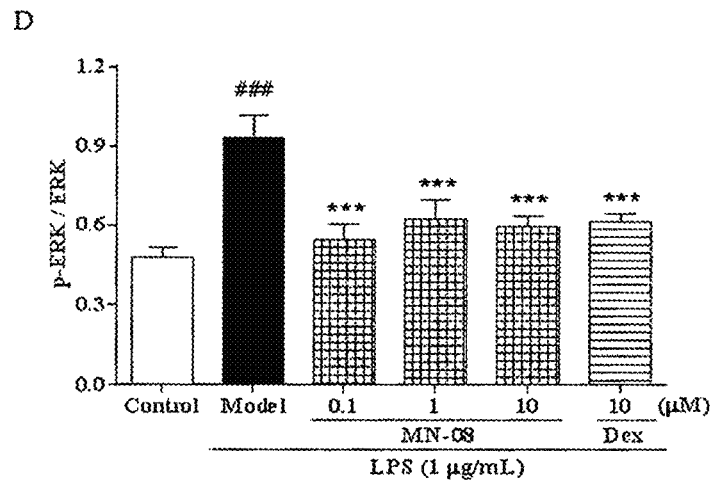
Figures 3, 19B:
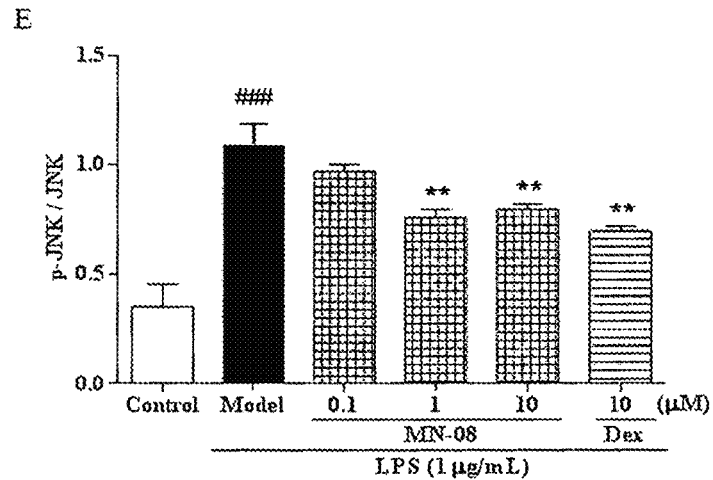
Figures 19C, 20:
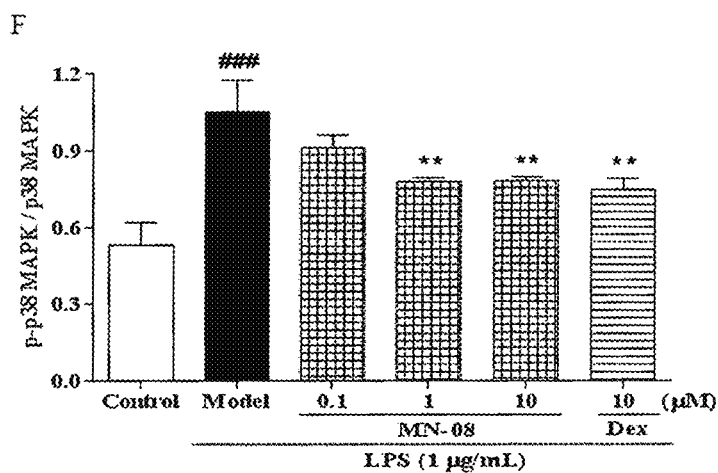

As a result, shown in FIG. 20, the amantadine nitrate compound has a significant protective effect on glutamate-induced cerebellar granule cells.

EXAMPLE 57

Inhibition of NMDA Receptor by Amantadine Nitrate Compounds

The patch-clamp technique was used to study the inhibitory activity of amantadine nitrate compounds on NMDA receptors in HEK293 cells stably transfected with human NR1 and NR2A. We used whole-cell patch clamp techniques to record changes in NMDA receptor channel currents. The clamping voltage of HEK293 cells was set at −70 mV, and various concentrations of the test compound and L-glutamate solution were added to stimulate the opening of the NMDA channel. The inhibitory effect of each compound on the L-glutamate-induced current increase was determined, and then the half maximal inhibitory concentration IC50 for NMDA channel of each of the compounds was calculated.

Figures 21, 22:
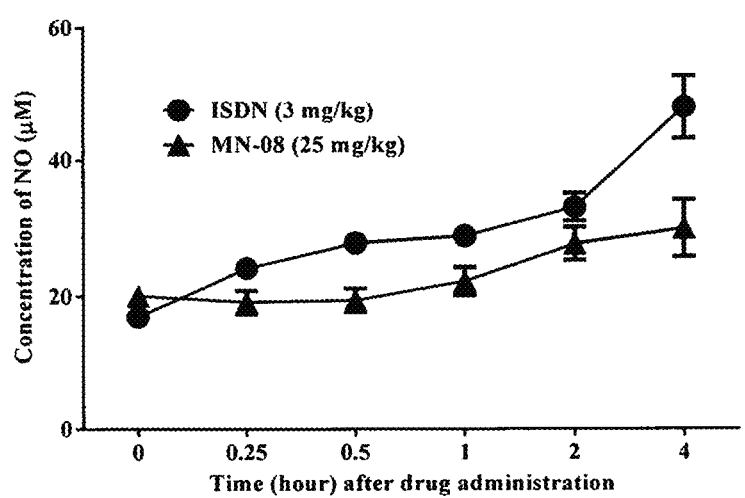
FIG. 21 illustrates the inhibition of NMDA receptor by amantadine nitrate compounds.
FIG. 22 illustrates the time concentration curve of NO in plasma after administration of MN-08 to rats.

As a result, shown in FIG. 21, the amantadine nitrate compound inhibited the increase of NMDA receptor channel current in HEK293 cells induced by L-glutamate, indicating that the amantadine nitrate compound has significant inhibitory activity against NMDA receptor.

EXAMPLE 58

Time-Concentration Curve of Plasma Nitric Oxide after Intravenous Administration of MN-08 to Rats Eight SD rats weighing 250±20 g were randomly divided into two groups, 4 in each group. Intravenous injection of MN-08 (25 mg/kg) or ISDN (3 mg/kg), respectively, and at 0 h, 0.25 h, 0.5 h, 1 h, 2 h, 4 h after bolus administration about 400 μL blood (anticoagulated with EDTA-K2) was taken and centrifuged at 3000 r/min for 10 min to get the supernatant, and the plasma sample was stored at −20° C. for testing. The amount of NO in the plasma was determined according to the instructions of the total nitric oxide detection kit of Biyuntian.

As a result, shown in FIG. 22, an amantadine nitrate compound such as MN-08 can release nitric oxide in the body.

EXAMPLE 59

Relaxation of MN-08 on the Middle Cerebral Artery of Rats

Adult rats were taken and treated with cervical vertebrae dislocation, decapitation, rapid removal of brain tissue, stripping of the middle cerebral artery, which was cut into a 2-3 mm vascular ring, standardized, checked for endothelial integrity, and the uncompleted part being removed. The the vascular ring was pre-contracted with 60 mM KC. After the plateau was reached, different concentrations of MN-08 and positive control drugs were added to monitor the vascular tension changes for 30 min. The vasodilation curve and the maximum diastolic percentage were observed and calculated within 30 min.

Figure 23A:
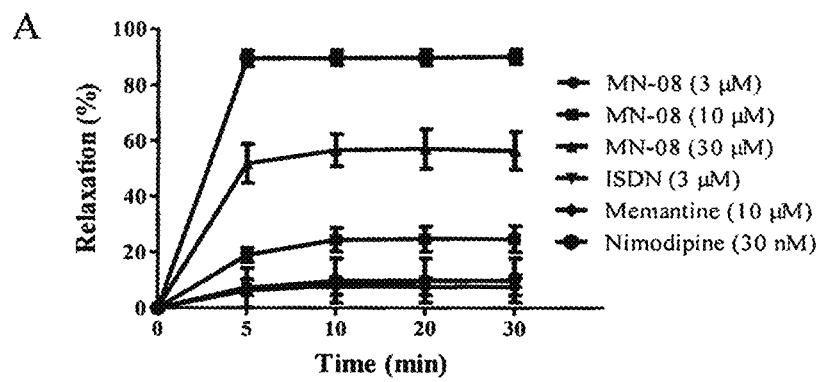
FIGS. 23A and 23B illustrate the relaxation effect of compound MN-08 on the middle cerebral artery of rats.
Figure 23B:
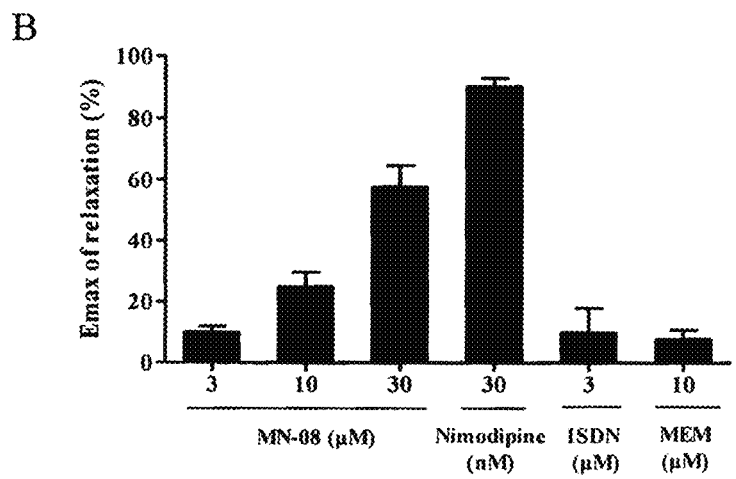

As a result, shown in FIGS. 23A and 23B, MN-08 has a significant expansion effect on the middle cerebral artery which is pre-contracted by potassium chloride.

EXAMPLE 60

The Relaxation Effect of MN-08 on Cerebral Blood Vessels is Related to its Binding to NMDA Receptors Adult rats were taken and treated with cervical vertebrae dislocation, decapitation, rapid removal of brain tissue, stripping of middle cerebral artery, which was cut into a 2-3 mm vascular ring, standardized, and checked for endothelial integrity, and on the intact vascular ring, MK-801 (10 μM) was incubated for 20 min, and ddH$_2$O of an equal volume was used as a blank control, and then the vascular ring was contracted with U46619 (1 μM). After the plateau of contraction was reached, MN-08 (30 μM) was added, and vascular tension changes were monitored for 20 min. The vasodilation curve was observed and calculated within 20 min. The effect of MN-08 vasodilation was compared for use of NMDA receptor blockers and no-use of the blockers, so that the relationship between MN-08 vasodilation and NMDA was analyzed.

Figure 24:
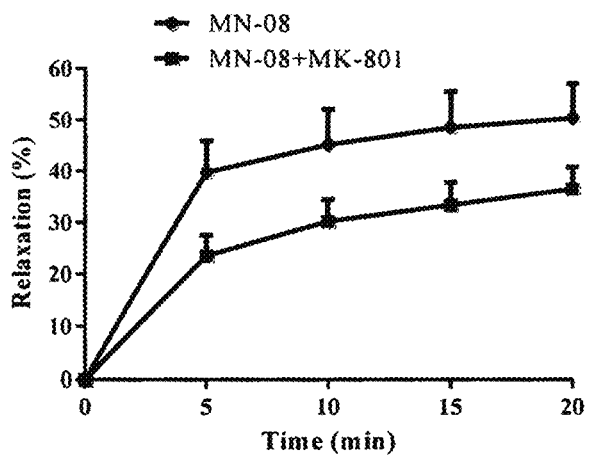
FIG. 24 illustrates the relationship between the relaxation effect of compound MN-08 on cerebral blood vessels and its binding to NMDA receptors.

The results are shown in FIG. 24. MN-08 was applied alone and had significant vasodilator activity. When the NMDA receptor antagonist MK-801 (MK-801 has no vasodilating activity) completely blocks the NMDA receptor, MN-08 no longer binds to the NMDA receptor, and the vasodilator capacity is significantly reduced.

EXAMPLE 61

Effect of MN-08 on Peripheral Blood Pressure, Heart Rate and Regional Cerebral Blood Flow in Normal Rats Twenty-one male SD rats, weighing in the range of 280-320 g, were purchased from the Guangdong Experimental Animal Center (SCXK (Yue) 2013-0002). The drug-administered group (MN-08, Nimodipine, Memantine) was 6 in each group, and 3 in the saline control group. Experimental method: The rats were intubated with femoral artery with PE50 tube under 2.5% isoflurane anesthesia for peripheral blood pressure and heart rate measurement. After the femoral artery cannulation was completed, the PE50 tube was connected to the transducer (MLT844, AD Instruments, Australia), anesthesia was maintained under 1% isoflurane, and blood pressure and heart rate data were collected after 30 minutes of equilibrium (PowerLab, AD Instruments, Australia), local hemorrhage (PF5001, PeriMed, Sweden) was monitored by laser Doppler flowmetry. After the basic value was collected for 20 min, MN-08 (12.5 mg/kg), Nimodipine (0.1 mg/kg), Memantine (10 mg/kg) and Saline (3 ml/kg) was continuously injected for 30 min through the tail vein using a micro-continuous drug delivery pump, and, after dosing, the condition was further monitored for 20 min.

Results are as shown in FIG. 25A-H and FIG. 26A-D, MN-08 had effects for slight increase in peripheral blood pressure, slight decrease in heart rate, and slight increase in cerebral blood flow; Memantine and Nimodinepine were more effective in lowering peripheral blood pressure and lowering heart rate; Nimodipine has a significant increase in cerebral blood flow; Memantine has a slight reduction in cerebral blood flow.

EXAMPLE 62

MN-08 has Effect on Protection of Retinal Ganglion Cells in Acute Glaucoma Rats

Male SD rats, weighing in the range of 250-300 g, were purchased from the Guangdong Medical Laboratory Animal Center (certificate: 44007200028940). The experiment was divided into 4 groups of Sham, Model, MN-08 and Memantine, with 5 rats in each group. The acute glaucoma model of rats was induced by anterior chamber perfusion of saline, to cause high intraocular pressure of 90-100 mmHg with pressurization for 60 min. Compounds and positive control drugs were injected twice daily into the tail vein 3 hours, 6 hours, and day 2-day 4 after surgery. Four days after the administration of the model, the rat was anesthetized with sodium pentobarbital anesthesia. The eyeballs were taken and fixed in 4% paraformaldehyde for 30 min, and the retina was removed to stain the optic ganglion cells. The retina was fixed with 4% paraformaldehyde for 30 min and washed three times with PBS for 10 min each time. Add 500 μL of blocking solution, and after 1 h, aspirate the blocking solution, add 300 j L of a 1:200 dilution of Brn3 antibody dilution, and place at 4° C. for 2 days. The antibody dilution was aspirated and washed three times with PBS for 10 min each time. Add 300 μL of 1:1000 dilution of scorpion anti-sheep 488 antibody dilution, and avoid light for 1 h at room temperature. The antibody dilution was aspirated and washed three times with PBS for 10 min each time, and the cells were photographed and the survival rate of the ganglion cells was calculated.

The results are shown in FIGS. 27A and 27B. MN-08 can reduce the apoptosis of retinal ganglion cells in glaucoma rats and increase the survival rate of ganglion cells.

EXAMPLE 63

MN-08 Significantly Reduced Intraocular Pressure in Transient Glaucoma New Zealand Rabbits Male New Zealand rabbits, weighing 1.5 to 2 kg, were purchased from the Guangdong Medical Laboratory Animal Center (certificate: 4441160002408). The experiment was divided into 3 groups of model group, MN-08 and Memantine, with 4 New Zealand rabbits in each group. A New Zealand rabbit vitreous injection of hypertonic saline (5%, 0.1 ml) was used to induce a transient glaucoma model in New Zealand rabbits. The intraocular pressure (0 min) of New Zealand rabbits was measured before injection of hypertonic saline, and the intraocular pressure (1 min) was measured immediately after injection of hypertonic saline, and the New Zealand rabbits with intraocular pressure below 70 mmHg were removed. Drug was administered immediately after the model being determined to be successful. Then, the intraocular pressure was measured at 10 min, 30 min, 60 min, 90 min, 120 min, 150 min, and 180 min, with 3 times at each time point, and the average value was taken as the intraocular pressure for respective time point.

Figure 28:
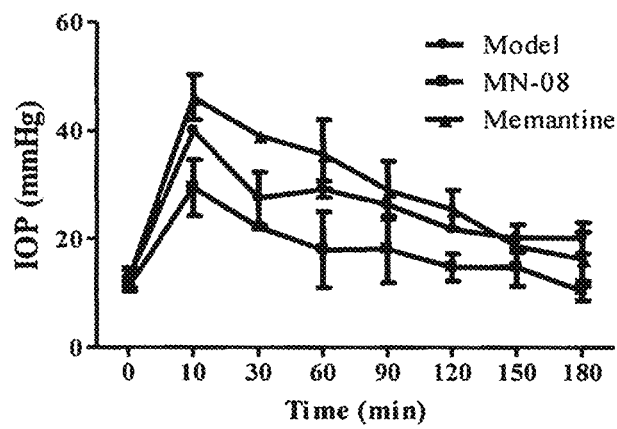
FIG. 28 illustrates the effect of compound MN-08 on reducing intraocular pressure in New Zealand rabbit acute glaucoma model.

As a result, shown in FIG. 28, MN-08 can significantly reduce the intraocular pressure of the New Zealand rabbits in an acute glaucoma model.

EXAMPLE 64

The Effects of MN-08 on Temporal Cortical Blood Flow in Vascular Dementia Model Rats Male SD rats was taken weighing 250-300 g. Breeding conditions: The animals were raised in the SPF laboratory animal center of the Experimental Animal Center of Jinan University, and were raised according to the requirements of SPF rat breeding. The animals were randomly divided into 7 groups: blank group (11), model group (12), MN-08 6.25 mg/kg dose group (8), MN-08 12.5 mg/kg dose group (9), MN-08 25 mg/kg dose group (5) and Memantine group (12). After SD rats were modeled bilateral bilateral common carotid artery ligation, MN-08 (6.25, 12.5, 25 mg/kg) was tail vein administered twice a day for 7 days. The blood flow of the temporal cortex was measured, 14, 28, 42 days after modeling, by laser Doppler flowmetry. The rats were anesthetized (with anesthetic isoflurane) using a small animal gas anesthesia system, and the right parietal bone was fully exposed along the midline incision of the rat head. At the point side 5 mm and back 2 mm from the anterior iliac crest of the rat, a small groove with a diameter of 1 mm was drilled, and the blood flow value of the temporal lobe was measured using a laser Doppler flowmeter. After the measurement, the cortex was sutured, the iodine was wiped at the wound, and the rats were returned to the cage.

Figure 29:
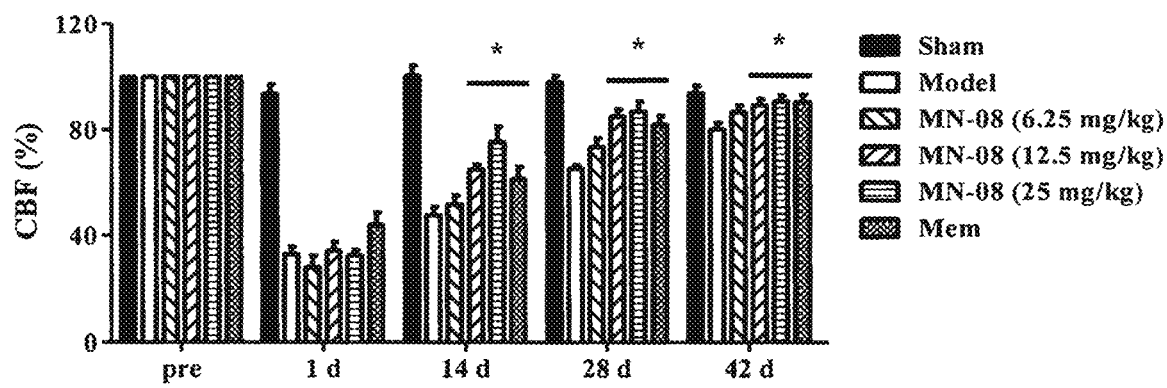
FIG. 29 illustrates the effect of compound MN-08 on temporal cortical blood flow in vascular dementia model rats.

The results are shown in FIG. 29. After the model rats were given MN-08, the blood flow of the temporal cortex of the rats was increased in various degrees.

EXAMPLE 22

Effect of MN-08 on the Total Distance of Motion, Speed of Motion and Recognition of New Objects in the Vascular Dementia Model Rats in Open Field Experiments Rats in each group were modeled and administered according to the above method. After 14, 28, and 42 days after modeling, the total field distance, the speed of movement and the recognition of new objects were detected in specified time periods with an open field experimental system. The open field experiment was carried out in a quiet environment, and the animals were placed in the center of the bottom of the box while recording and timing were performed, and the observation time per mouse was set to 5 minutes. When animals were replaced, the inner and bottom surfaces of the square box was cleaned to avoid the residual information (such as the animal's large, urinal, smell) of the last animal from affecting the next test results. According to the trajectory of rats recorded by the open field experiment software, the total distance and speed of movement of the rats were systematically analyzed. The new object recognition experiment was carried out in a square open field with a length, width and height of 50 cm. The two points from the upper left and upper right corners were used as the position for placing new and old objects. The point was the center of the circle and the radius of 5 cm was two. The areas are named Area 1 (the same object is placed during the familiarization period, new objects are placed during the test period) and Area 2. The experiment has three periods: the adaptation period, the familiarization period, and the test period. During the acclimation period, the rats were placed in an experimental device without any objects, allowing them to freely explore and adapt to the experimental environment to minimize the stress of the animals during the experiment. During the familiarization period, two identical objects were placed in the bottom plate of the experimental device, and the rats were placed in the experimental device in such a manner as to face the two objects. After 10 minutes, the animals were taken out and returned to the animal cage. At intervals of 1 h, a test period experiment was performed. One of the two identical objects was replaced with another different object. The camera captured the movement of the rat's head within 5 min and recorded the rats entering the range of Area 1 and Area 2. Time and the latency of identifying new objects were used as reference indicators for assessing the ability of rats to recognize memory. The preference of experimental animals for novel objects can be quantified by Discrimination Index". Discrimination Index is referred as D, which is calculated from the time of exploration of a novel object and the time of exploration of a familiar object by the animal during the test period. The specific calculation formula is: D=(Area 1-Area 2)/(Area 1+Area 2).

As a result, shown in FIGS. 30A-30C, MN-08 can significantly increase the total moving distance, the moving speed of the model rats in the open field, and significantly increase the new object recognition index of the model rats.

EXAMPLE 65

Effects of MN-08 on the Behavior of Rats with Subarachnoid Hemorrhage

Male SD rats, weighing 280 g-350 g, were purchased from the Guangdong Medical Laboratory Animal Center (certificate: 44007200025302). The experiment was divided into 5 groups of Sham, Model, MN-08 (3 mg/kg), MN-08 (6 mg/kg), MN-08 (12 mg/kg), and Memantine (10 mg/kg), with each group having 8 rats. The subarachnoid hemorrhage (SAH) model was induced by suture method. The compound and positive control drug were injected into the tail vein at 3 h, 6 h and day 2-day 7 after surgery, and neurobehavioral evaluation was performed at 3 h, 24 h, 72 h, 5 d and 7 d after surgery, respectively.

The results are shown in FIG. 31. MN-08 can significantly improve the behavior of rat models of subarachnoid hemorrhage.

EXAMPLE 67

Effect of MN-08 on Bleeding Severity Score in Rats with Subarachnoid Hemorrhage

After 7 days of model administration, the rats were euthanized with pentobarbital at the end of the experiment. The whole brain tissue (including cerebellum and brainstem) was taken out completely, photographed, and then the brain tissue picture was divided into 6 portions. For each portion, the SAH severity score was scored as follows, with a total score of 18 points; 0 point: no subarachnoid hemorrhage; 1 point: a small amount of bleeding; 2 points: moderate bleeding, but the blood vessels still being clearly identifiable; 3 points: severe bleeding, blood vessels not being distinguished. As scored, 0-7 is regarded as mild hemorrhage; 8-12 is regarded as moderate hemorrhage; 13-18 is regarded as severe hemorrhage.

Figure 32A:
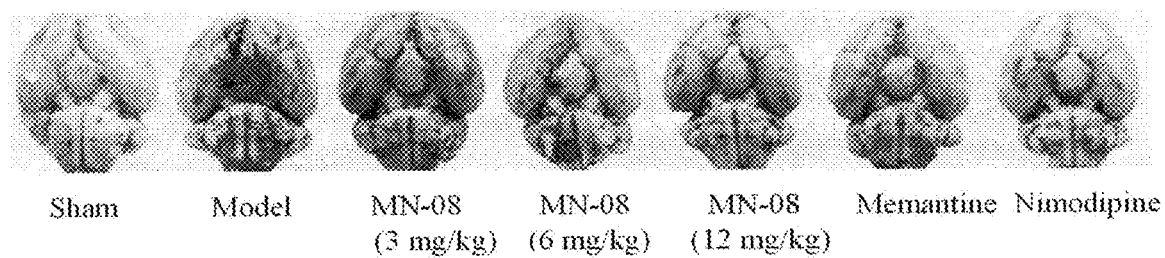
FIGS. 32A and 32B illustrate the effect of compound MN-08 on reducing the amount of subarachnoid hemorrhage in rats.
Figure 32B:
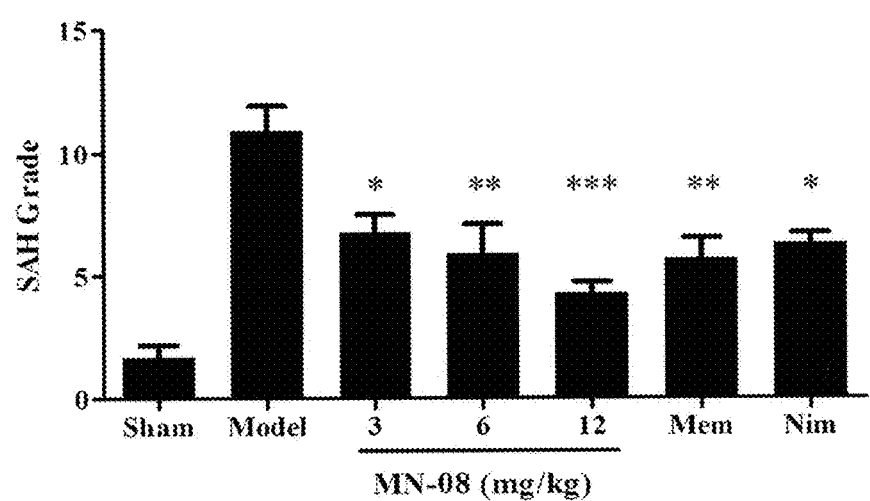

As a result, shown in FIGS. 32A and 32B, MN-08 can reduce the amount of subarachnoid hemorrhage in rats.

EXAMPLE 68

Improvement of MN-08 on the Vasospasm of SAH Rats

Seven days after model administration, rats were euthanized by pentobarbital sodium anesthesia, brain tissue photographed, fixed with 4% paraformaldehyde, dehydrated, paraffin-embedded for pathological section, HE staining of basilar artery, and calculated to get Basal artery circumference and thickness. The paraffin-HE staining process is as follows: 1) xylene dewaxing transparent: 5 min each, 2 times each; 2) alcohol gradient elution: 100% alcohol (5 min), 100% alcohol (2 min), 95% alcohol (2 min), 95% alcohol (2 min); 3) washed with water:deionized water, 1 min; 4) hematoxylin staining for 15 min, 37° C.; 5) Washing: washed slides for 30 s; 6) Differentiation: 1% hydrochloric acid alcohol differentiation for 3 s; 7) Washing: rinse with running water for 10-20 min (12 min), blue in this step; 8) Eosin staining: 0.5% eosin staining for 15 min, 37° C., difficult to color, and adding 1-2 drops of glacial acetic acid per 100 mL of dye solution, easy to color, not easy to decolorize; 9) alcohol hydration: 70%, 80%, 95%, 100%, 100%, 100% alcohol dehydration 30 s, 30 s, 30 s, 1 min, 3 min, 3 min; 10) transparency: xylene is transparent 2 times for 3 min each time; 11) cover: neutral resin seal, photographed. The basilar artery circumference and thickness were analyzed.

Figure 33A:
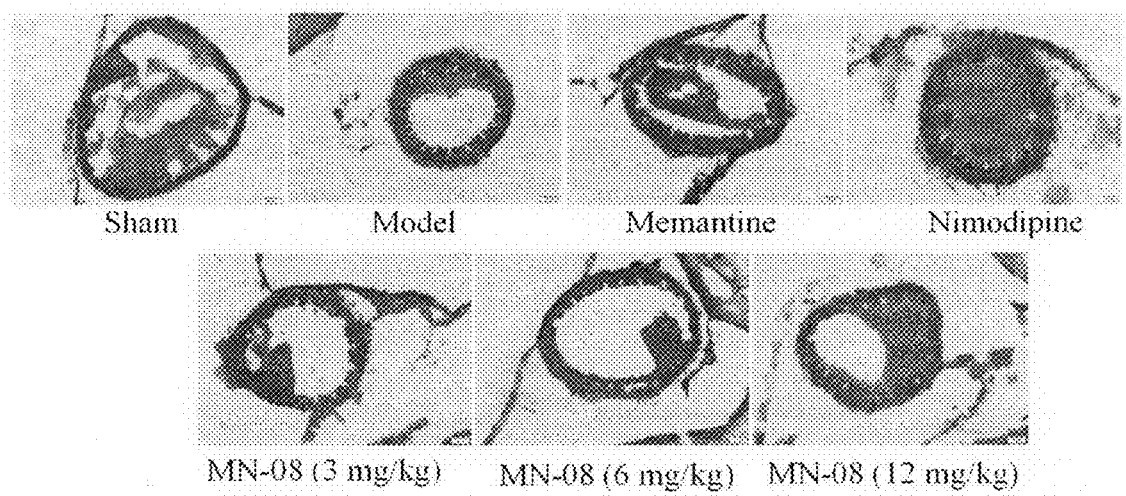
FIGS. 33A to 33C illustrate the effect of compound MN-08 on the cerebral vasculature (basal artery) spasm in rats with subarachnoid hemorrhage.
Figure 33B:
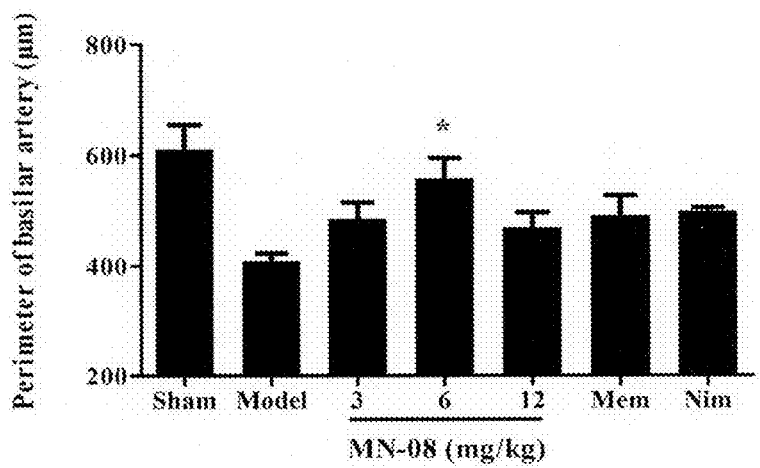
Figure 33C:
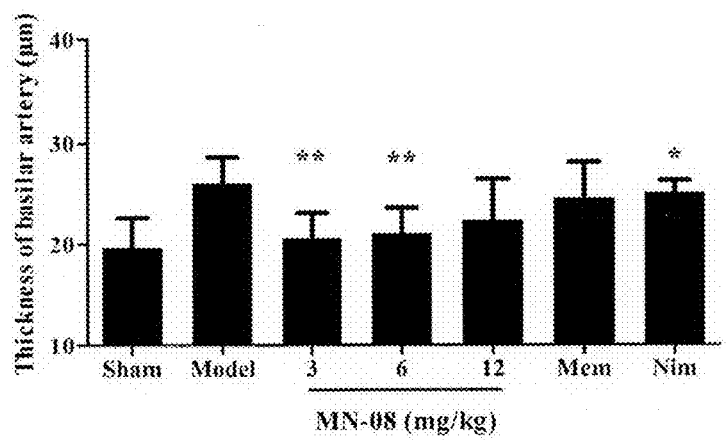

The results are shown in FIGS. 33A to 33C. In the subarachnoid hemorrhage, the circumference of the basilar artery was reduced and the vessel wall was thickened. MN-08 can significantly improve vasospasm in rats with subarachnoid hemorrhage.

EXAMPLE 69

Tissue Distribution in MN-08 Rats

Male SD rats, weighing in a range of 250-280 g, were purchased from the Guangdong Experimental Animal Center (SCXK (Yue) 2013-0002). The experiment was divided into 6 groups (5 min, 15 min, 30 min, 60 min, 90 min, 120 min) with 3 rats in each group. After fasting for 12 h, the rats were injected with MN-08 (27 mg/kg) through the tail vein, anesthetized at 5 min, 15 min, 30 min, 60 min, 90 min and 120 min, and the hearts, liver, spleen, lung, kidney, stomach, brain and blood were taken. Heparin sodium anticoagulation was added to the blood sample, and the sample was centrifuged at 4500 rpm for 10 min to obtain a plasma sample. Each tissue sample was subjected to HPLC analysis after passing through a biological sample processing method. The tissue samples were washed with physiological saline, blotted with filter paper and weighed (AL204, Mettler-Toledo, USA), and added to physiological saline at a weight-to-volume ratio of 1:2 (g/mL). After homogenization, 200 mL was taken. The homogenate was placed in a 1.5 mL centrifuge tube, 100 mL of methanol (containing internal standard MN-12), 200 mL of acetonitrile was added, mixed and vortexed for 2 min, centrifuged at 10,000 rpm for 10 min, and the supernatant liquid filtration membrane was taken, with 20 mL was analyzed by HPLC. Spectral conditions: chromatographic column: Agilent ZORBAX Eclipse C18 column (250×4 mm, 5 mm); guard column: Guangzhou Yinghe (10×4.6 mm, 5 mm); mobile phase: methanol–0.025 M dipotassium hydrogen phosphate solution (70:30); flow rate 1 mL/min; detection wavelength: 216 nm; column temperature: room temperature.

Figure 34:
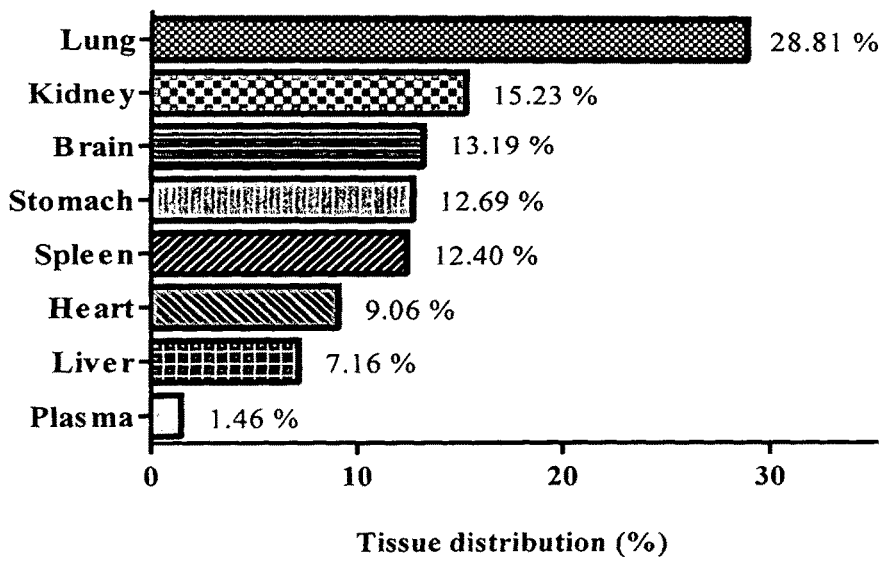
FIG. 34 illustrates the tissue distribution of compound MN-08 in rats.

As a result, shown in FIG. 34, MN-08 was widely distributed in tissues, especially in lung tissues.

EXAMPLE 70

Effect of MN-08 on Pulmonary Hypertension Model Rats

Fifty three male SD rats, weighing in a range of 180-230 g, were purchased from the Guangdong Experimental Animal Center (SCXK (Yue) 2013-0002). The rats were randomly divided into 6 groups: normal control group (8), model group (11), MN-08 group (9), MN-12 group (8), Memantine group (8) and Sildenafil group (9 rats). The pulmonary hypertension model of rats was modeled by subcutaneous injection of monocrotaline (50 mg/kg, sc) (day 1), and the rats were kept for 11 days, and the treatment was started on the 12th day for Normal Control group (Saling, 1 ml/animal, iv, bid), model group (Saling, 1 ml/animal, iv, bid), MN-08 group (12.5 mg/kg, iv, bid), MN-12 group (15 mg/kg, iv, bid), Memantine group (10 mg/kg, iv, bid) and Sildenafil group (10 mg/kg, iv, bid). Treatment period is 12-28 days, measured at right 29 ventricular pressure was removed and heart tissue was removed. Rats were anesthetized with urethane (1.2 g/kg) and connected to a transducer (MLT844, AD Instrument, Australia) with a heparin-filled PE50 tube. The rats were subjected to right ventricular intubation and measured (PowerLab, AD Instruments, Australia). After the rats were sacrificed by bleeding, the heart tissue was removed and the right ventricle and (RV) left ventricle were separated from the ventricular septum (LV+S) on filter paper. The weight of the right ventricle, left ventricle+ventricular septum was weighed separately after draining the water.

Figure 35A:
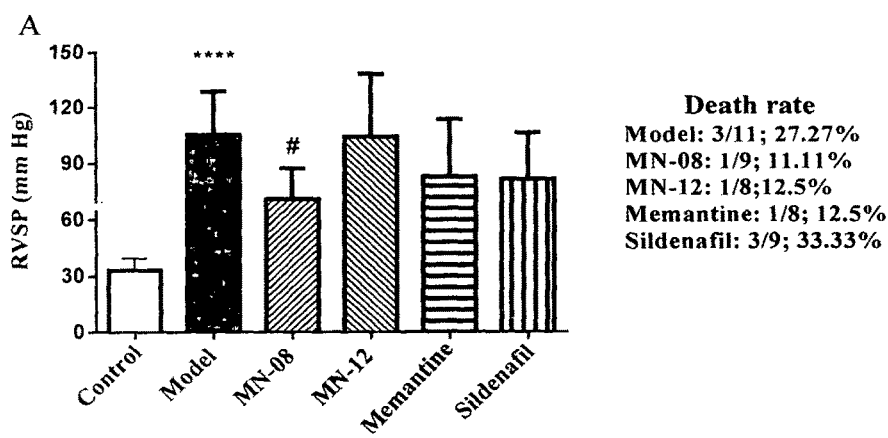
FIGS. 35A to 35C illustrate compound MN-08 significantly reduced right ventricular systolic pressure and reduced right ventricular hypertrophy in rats with pulmonary hypertension.
Figure 35B:
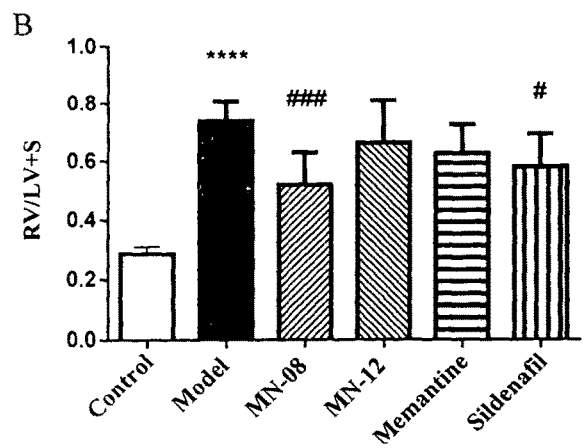
Figure 35C:
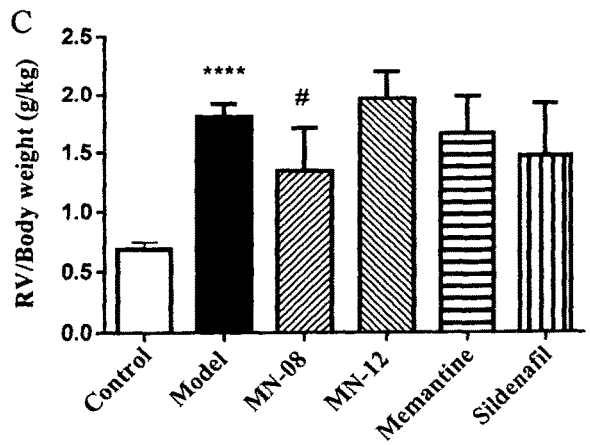

As results, shown in FIGS. 35A to 35C, MN-08 can significantly reduce right ventricular systolic pressure in rats with pulmonary hypertension and reduce mortality in rats with pulmonary hypertension; can significantly reduce the weight ratio of right ventricle (RV) to left ventricle and ventricular septal (LV+S) in rats with pulmonary hypertension; can significantly reduce the right ventricle and body weight ratio of pulmonary hypertension model rats.

The invention claimed is:

1. A method for the treatment of diseases, comprising administration of a therapeutically effectively amount of an amantadine nitrate compound, wherein the diseases are related to NMDA receptor, NO production or free radicals overload, or related to neurodegeneration;

wherein the diseases related to NMDA receptor are: cerebral ischemia, Parkinson's disease, Alzheimer's disease, amyotrophic lateral sclerosis, ataxia telangiectasia, bovine spongiform encephalopathy, Creutzfeldt-Jakob disease, Huntington's disease, cerebellum atrophy, multiple sclerosis, primary amyotrophic lateral sclerosis, spinal muscular atrophy, glaucoma, vascular dementia, subarachnoid hemorrhage, pulmonary arterial hypertension, chronic obstructive pulmonary disease, acute lung injury, bronchial asthma, or age-related macular degeneration;

wherein the diseases related to NO production are: stroke, brain trauma, epilepsy, Parkinson's disease, Huntington's disease, amyotrophic lateral sclerosis, Alzheimer's disease, hypoxic-ischemic brain damage, cerebral hemorrhage, dementia, ischemic heart disease, blood clots, atherosclerosis, hypercholesterolemia, emphysema, cataracts, diabetes, acute pancreatitis, alcohol-induced liver disease, kidney damage, glaucoma, vascular dementia, subarachnoid hemorrhage, pulmonary arterial hypertension, chronic obstructive pulmonary disease, acute lung injury, or bronchial asthma;

wherein the diseases related to neurodegeneration are: cerebral ischemia, Parkinson's disease, Alzheimer's disease, amyotrophic lateral sclerosis, ataxia telangiectasia, bovine spongiform encephalopathy, Creutzfeldt-Jakob disease, Huntington's disease, spinocerebellar ataxia, multiple sclerosis, primary lateral sclerosis, or spinal muscular atrophy;

wherein, the amantadine nitrate compound has a structure of:

(A) formula (II):

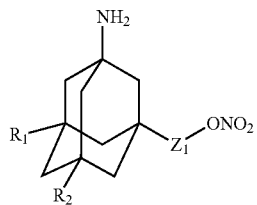

(II)

or a pharmaceutically acceptable salt thereof,
wherein $R_2$ is hydrogen, $R_1$ is a straight-chain or branched-chain alkyl, and number of carbon atoms contained in $Z_1$ and $R_1$ together is no less than 3; or (B) formula (III):

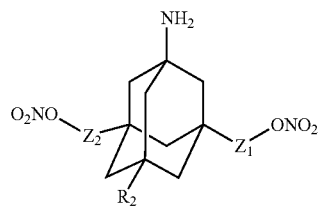

(III)

or a pharmaceutically acceptable salt thereof,
wherein $R_2$ is hydrogen, straight-chain or branched-chain or cyclic alkyl, optionally substituted-aryl or heteroaryl, or contains a nitrate ester group;
wherein $Z_1$ and $Z_2$ are each independently a straight- or branched-carbon chain connecting to a nitrate ester group, wherein $Z_1$ and $Z_2$ each independently can be substituted with heteroatom, alkyl, aryl and heteroaryl, and $Z_1$ and $Z_2$ each independently have 1-6 carbon atoms;
wherein, the alkyl has up to 10 carbon atoms, the cyclic alkyl is cyclopropyl, cyclobutyl, cyclopentyl or cyclohexyl; a substituent is $N(CH_3)_2$, F, Cl, Br, I, $OCH_3$, $CO_2CH_3$, CN, aryl or heteroaryl; the aryl is monocyclic aryl, and the heteroaryl is monocyclic heteroaryl.

2. The method of claim 1, wherein the amantadine nitrate compound of formula (II) is selected from the group consisting of:

NM-004

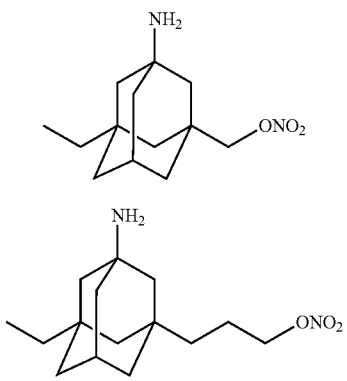

NM-005

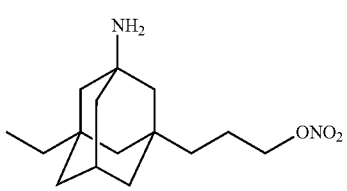

NM-006

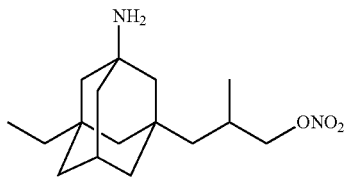

NM-007

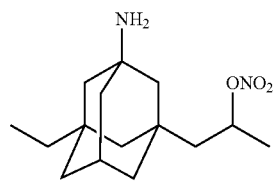

or a pharmaceutically acceptable salt thereof.

3. The method of claim 1, wherein the amantadine nitrate compound of formula (III) is selected from the group consisting of:

NM-008

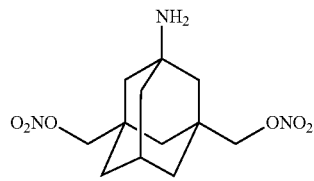

NM-009

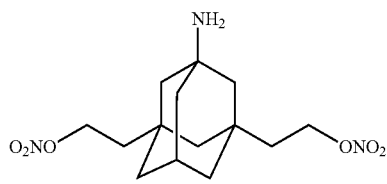

NM-010

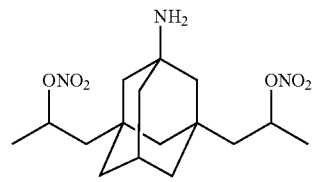

NM-011

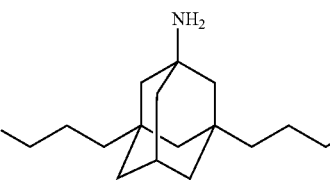

NM-012

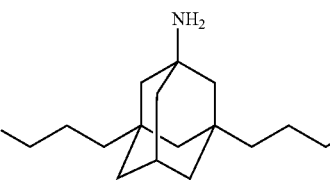

or a pharmaceutically acceptable salt thereof.

4. The method of claim 1, wherein $R_2$ in the formula (III) contains a nitrate ester group, and thus the amantadine nitrate compound has a structure of formula (IV):

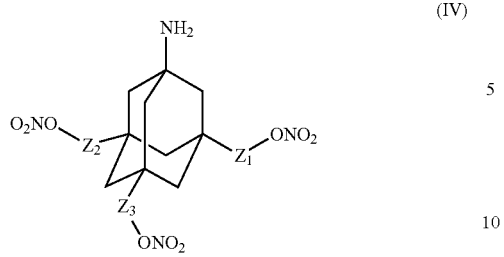

(IV)

or a pharmaceutically acceptable salt thereof,
wherein, $Z_1$, $Z_2$ and $Z_3$ are each independently a straight- or branched-carbon chain connecting to a nitrate ester group of $R_1$, $R_2$ and $R_3$ respectively, wherein $Z_1$, $Z_2$ and $Z_3$ each independently can be substituted with heteroatom, alkyl, aryl and heteroaryl, and $Z_1$, $Z_2$ and $Z_3$ independently have 1-6 carbon atoms;

wherein, the alkyl has up to 10 carbon atoms, the cyclic alkyl is cyclopropyl, cyclobutyl, cyclopentyl or cyclohexyl; a substituent is $N(CH_3)_2$, F, Cl, Br, I, $OCH_3$, $CO_2CH_3$, CN, aryl or heteroaryl; the aryl is monocyclic aryl, and the heteroaryl is monocyclic heteroaryl.

* * * * *